United States Patent
Caramelli et al.

(10) Patent No.: US 11,472,772 B2
(45) Date of Patent: *Oct. 18, 2022

(54) S1P3 ANTAGONISTS

(71) Applicant: Teva Pharmaceutical Industries, Ltd., Petach-Tikva (IL)

(72) Inventors: Chiara Caramelli, Sovicille (IT); Cesare Federico, Perugia (IT); Emanuele Gabellieri, Lausanne (CH); Matteo Magnani, Pratovecchio (IT); Iolanda Micco, Singapore (SG); Georg C. Terstappen, Battenberg (DE)

(73) Assignee: TEVA PHARMACEUTICAL INDUSTRIES LIMITED, Petach Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/751,472

(22) Filed: Jan. 24, 2020

(65) Prior Publication Data

US 2020/0157052 A1 May 21, 2020

Related U.S. Application Data

(60) Continuation of application No. 15/923,837, filed on Mar. 16, 2018, now abandoned, which is a division of application No. 15/100,326, filed as application No. PCT/EP2014/075986 on Nov. 28, 2014, now Pat. No. 9,951,017.

(30) Foreign Application Priority Data

Dec. 2, 2013 (EP) .................................. 13195372

(51) Int. Cl.
| | |
|---|---|
| *C07D 213/75* | (2006.01) |
| *C07D 403/12* | (2006.01) |
| *C07D 401/12* | (2006.01) |
| *C07D 413/12* | (2006.01) |
| *C07D 417/12* | (2006.01) |
| *C07D 241/16* | (2006.01) |
| *C07D 277/32* | (2006.01) |
| *C07D 401/14* | (2006.01) |
| *C07D 405/14* | (2006.01) |
| *C07D 417/14* | (2006.01) |

(52) U.S. Cl.
CPC ......... *C07D 213/75* (2013.01); *C07D 241/16* (2013.01); *C07D 277/32* (2013.01); *C07D 401/12* (2013.01); *C07D 401/14* (2013.01); *C07D 403/12* (2013.01); *C07D 405/14* (2013.01); *C07D 413/12* (2013.01); *C07D 417/12* (2013.01); *C07D 417/14* (2013.01)

(58) Field of Classification Search
CPC .. C07D 213/75; C07D 241/16; C07D 277/32; C07D 401/12; C07D 401/14; C07D 403/12; C07D 405/14; C07D 413/12; C07D 417/12; C07D 417/14
See application file for complete search history.

(56) References Cited

U.S. PATENT DOCUMENTS

| | | | |
|---|---|---|---|
| 6,610,846 B1 | 8/2003 | Bizzarro | |
| 9,951,017 B2* | 4/2018 | Caramelli | ............ C07D 241/16 |
| 2001/0039344 A1 | 11/2001 | Bizzarro | |
| 2003/0171411 A1* | 9/2003 | Kodra | ........................ A61P 1/00 |
| | | | 514/357 |
| 2004/0186290 A1* | 9/2004 | Fyfe | ..................... C07D 413/12 |
| | | | 544/238 |
| 2007/0281942 A1 | 12/2007 | Cao | |
| 2010/0063063 A1 | 3/2010 | Benbow | |
| 2018/0201582 A1 | 7/2018 | Caramelli | |

FOREIGN PATENT DOCUMENTS

| | | |
|---|---|---|
| EP | 81756 | 7/1983 |
| EP | 3689864 A1 | 8/2020 |
| JP | 2002155065 | 5/2002 |
| JP | 2020023512 A | 2/2020 |
| WO | WO 2000/026202 | 11/2000 |
| WO | WO 2001/036415 | 5/2001 |
| WO | WO 2001/083465 | 11/2001 |
| WO | WO 2002/046173 | 6/2002 |
| WO | WO 2003/063797 | 8/2003 |
| WO | WO 2003/095438 | 11/2003 |
| WO | WO 2004/052869 | 6/2004 |
| WO | WO 2005/075435 | 8/2005 |
| WO | WO 2006/058923 | 6/2006 |
| WO | WO 2007/026761 | 3/2007 |
| WO | WO 2007/041365 | 4/2007 |
| WO | WO 2007/087066 | 8/2007 |
| WO | WO 2008/005914 | 1/2008 |
| WO | WO 2008/078674 | 7/2008 |
| WO | WO 2008/119734 | 10/2008 |

(Continued)

OTHER PUBLICATIONS

Wang; Bioorg. Med. Chem. Lett. 2010, 20, 493-498. doi: 10.1016/j.bmcl.2009.11.112 (Year: 2010).*

Jun. 3, 2019 Restriction/Election Requirement issued by the United States Patent and Trademark Office in connection with U.S. Patent Application Publication No. US 2018/0201582 A1.

Response to May 29, 2019 Restriction/Election Requirement issued by the United States Patent and Trademark Office in connection with U.S. Patent Application Publication No. US 2018/0201582 A1.

(Continued)

*Primary Examiner* — Daniel R Carcanague
(74) *Attorney, Agent, or Firm* — Gary J. Gershik

(57) ABSTRACT

The present invention relates to antagonists of the S1P3 receptor formula (A) as herein described and pharmaceutical compositions thereof. The compounds of formula (A) are useful in the preparation of a medicament, in particular for the treatment of Alzheimer's disease.

20 Claims, 4 Drawing Sheets

(56) References Cited

FOREIGN PATENT DOCUMENTS

| WO | WO 2008/141013 | A1 | 11/2008 | | |
|---|---|---|---|---|---|
| WO | WO 2008/141119 | | 11/2008 | | |
| WO | WO 2008/147797 | | 12/2008 | | |
| WO | WO 2009/006315 | | 1/2009 | | |
| WO | WO 2009/091014 | | 7/2009 | | |
| WO | WO 2009/123896 | | 10/2009 | | |
| WO | WO 2009/140624 | | 11/2009 | | |
| WO | WO 2010/054138 | | 5/2010 | | |
| WO | WO 2011/008475 | A1 | 1/2011 | | |
| WO | WO 2011/019681 | A1 | 2/2011 | | |
| WO | WO-2012082817 | A1 | * 6/2012 | ................ | A61P 9/00 |

OTHER PUBLICATIONS

Sep. 25, 2019 Non-Final Rejection issued by the United States Patent and Trademark Office in connection with U.S. Patent Application Publication No. US 2018/0201582 A1.
Jan. 23, 2019 First Examination Report issued by the Australian Patent Office in connection with Australian Patent Application No. 2014359489.
Dec. 18, 2019 Response to First Examination Report issued by the Australian Patent Office in connection with Australian Patent Application No. 2014359489.
Jan. 3, 2020 Second Examination Report issued by the Australian Patent Office in connection with Australian Patent Application No. 2014359489.
Jan. 14, 2020 Response to Second Examination Report issued by the Australian Patent Office in connection with Australian Patent Application No. 2014359489.
Aug. 22, 2018 Response to First Office Action issued by the China National Intellectual Property Administration of China in connection with Chinese Patent Application No. 201480074769.6 (including English Language translation).
Nov. 2, 2018 Second Office Action issued by the China National Intellectual Property Administration of China in connection with Chinese Patent Application No. 201480074769.6 (including English Language translation).
Mar. 13, 2019 Response to Second Office Action issued by the China National Intellectual Property Administration of China in connection with Chinese Patent Application No. 201480074769.6 (including English Language translation).
Apr. 3, 2019 Response to Office Action issued by the Eurasian Patent Office in connection with Eurasian Patent Application No. 201691160 (including English Language translation).
Sep. 27, 2019 Reply to Rule 71(3) Communication issued by European Patent Office in connection with European Patent Application No. EP14811790.6.
Jan. 14, 2020 Invitation to Remedy Deficiencies issued by the European Patent Office in connection with European Patent Application No. 19210115.2.
Mar. 17, 2020 Response to Invitation to Remedy Deficiencies issued by the European Patent Office in connection with European Patent Application No. 19210115.2.
Jun. 7, 2019 First Examination Report issued by the Indian Patent Office in connection with Indian Patent Application No. 201627022648 (including English Language translation).
Mar. 5, 2020 Response to First Examination Report issued by the Indian Patent Office in connection with Indian Patent Application No. 201627022648 (including English Language translation).
Sep. 11, 2018 First Office Action issued by the Japanese Patent Office in connection with Japanese Patent Application No. 2016-536883 (including English Language translation).
Mar. 11, 2019 Response to First Office Action issued by the Japanese Patent Office in connection with Japanese Patent Application No. 2016-536883 (including English language translation).
May 21, 2019 Second Office Action issued by the Japanese Patent Office in connection with Japanese Patent Application No. 2016-536883 (including English language translation).

English Translation of Aug. 16, 2019 Response to Second Office Action issued by the Japanese Patent Office in connection with Japanese Patent Application No. 2016-536883.
Guerrero M, et al., "Discovery, design and synthesis of a selective S1P3 receptor allosteric agonist", Bioorganic & Medicinal Chemistry Letters, vol. 23, No. 23, Dec. 1, 2013, pp. 6346-6349.
International Search Report and Written Opinion of the International Searching Authority dated Feb. 20, 2015 in connection with PCT International Application No. PCT/EP2014/075986.
Wang et al. Bioorganic & Medicinal Chemistry Letters (2010), 20(2), 493-498.
Jeffrey A. Pfefferkorn et al., Discovery of (S)-6-(3-Cyclopentyl-2-(4-(trifluoromethyl)-1H-imidazol-1-yl)propanamido)nicotinic Acid as a Hepatoselective Glucokinase Activator Clinical Candidate for Treating Type 2 Diabetes Mellitus Journal of Medicinal Chemistry (2012), 55 (3), 1318-1333.
Ramakanth Sarabu et al. Discovery of Piragliatin-First Glucokinase Activator Studied in Type 2 Diabetic Patients Journal of Medicinal Chemistry (2012), 55(16), 7021-7036.
Yimin Qian et al., Identification of RO4597014, a Glucokinase Activator Studied in the Clinic for the Treatment of Type 2 Diabetes. Medicinal Chemistry Letters (2013), 4(4), 414-418.
Nancy-Ellen Haynes et al. Discovery, Structure-Activity Relationships, Pharmacokinetics, and Efficacy of Glucokinase Activator (2R)-3-Cyclopentyl-2-(4-methanesulfonylphenyl)-N-thiazol-2-yl-propionamide (RO0281675). Journal of Medicinal Chemistry (2010), 53(9), 3618-3625.
Zhongsheng Yu and Zuoheng Chen, Ingyong Huaxue (Chinese Journal of Medicinal Chemistry) (1990), 7 (6), 54-7.
Anelli, V., Bassi, R., Tettamanti, G., Viani, P. and Riboni, L. (2005) Extracellular release of newly synthesized sphingosine-1-phosphate by cerebellar granule cells and astrocytes. J. Neurochem., 92, 1204-1215.
Bajwa A, Huang L, Ye H, Dondeti K, Song S, Rosin DL, Lynch KR, Lobo PI, Li L, Okusa MD. (2012). Dendritic cell sphingosine 1-phosphate receptor-3 regulates Th1-Th2 polarity in kidney ischemia-reperfusion injury. J Immunol. 189(5):2584-96.
Balthasar S, Samulin J, Ahlgren H, Bergelin N, Lundqvist M, Toescu EC, Eggo MC, Tornquist K. (2006). Sphingosine 1-phosphate receptor expression profile and regulation of migration in human thyroid cancer cells. Biochem J. 398(3):547-56.
Brinkmann V. (2009). FTY720 (fingolimod) in Multiple Sclerosis: therapeutic effects in the immune and the central nervous system. Br J Pharmacol. 158(5):1173-82.
Brinkmann V. (2007). Sphingosine 1-phosphate receptors in health and disease: mechanistic insights from gene deletion studies and reverse pharmacology. Pharmacol Ther. 115(1):84-105.
Bradl M, Hohlfeld R. (2003). Molecular pathogenesis of neuroinflammation. J Neural Neurosurg Psychiatry. 74(10):1364-70.
Camprubi-Robles M, Mair N, Andratsch M, Benetti C, Beroukas D, Rukwied R, Langeslag M, Proia RL, Schmelz M, Ferrer Montiel AV, Haberberger RV, Kress M. (2013). Sphingosine-1-phosphate-induced nociceptor excitation and ongoing pain behavior in mice and humans is largely mediated by S1P3 receptor. J Neurosci. 33(6):2582-92.
Cencetti F, Bernacchioni C, Nincheri P, Donati C, Bruni P. (2010). Transforming growth factor-betaI induces transdifferentiation of myoblasts into myofibroblasts via up-regulation of sphingosine kinase-1/S1P3 axis. Mol Biol Cell. 21(6):1111-24.
Chen LY, Woszczek G, Nagineni S, Logun C, Shelhamer JH. (2008). Cytosolic phospholipase A2alpha activation induced by S1P is mediated by the S1P3 receptor in lung epithelial cells. Am J Physiol Lung Cell Mol Physiol. 295(2):L326-35.
Chun J, Goetzl EJ, Hla T, Igarashi Y, Lynch KR, Moolenaar W. (2002). International Union of Pharmacology. XXXIV. Lysophospholipid receptor nomenclature. Pharmacol Rev 54: 265-269.
Davies L, Fassbender K, Walter S. 2013. Sphingolipids in neuroinflammation. Handb Exp Pharmacol. (216):421-30.
Forrest M, Sun SY, Hajdu R, Bergstrom J, Card D, Doherty G, Hale J, Keohane C, Meyers C, Milligan J, Mills S, Nomura N, Rosen H, Rosenbach M, Shei GJ, Singer II, Tian M, West S, White V, Xie J, Proia RL, Mandala S. (2004). Immune cell regulation and cardio-

(56) References Cited

OTHER PUBLICATIONS vascular effects of sphingosine 1-phosphate receptor agonists in rodents are mediated via distinct receptor subtypes. J Pharmacol Exp Ther. 309(2):758-68.

Fischer I, Alliod C, Martinier N, Newcombe J, Brana C, Pouly S. (2011). Sphingosine kinase 1 and sphingosine 1-phosphate receptor 3 are functionally upregulated on astrocytes under pro-inflammatory conditions. PLoS One. 6(8):e23905.

Foster CA, Howard LM, Schweitzer A, Persohn E, Hiestand PC, Balatoni B, Reuschel R, Beerli C, Schwartz M, Billich A. (2007). Brain penetration of the oral immunomodulatory drug FTY720 and its phosphorylation in the central nervous system during experimental autoimmune encephalomyelitis: consequences for mode of action in multiple sclerosis. J Pharmacol Exp Ther. 323(2):469-75.

Gude DR, Alvarez SE, Paugh SW, Mitra P, Yu J, Griffiths R, Barbour SE, Milstien S, Spiegel S. (2008). Apoptosis induces expression of sphingosine kinase 1 to release sphingosine-1-phosphate as a "come-and-get-me" signal. Faseb J. 22(8):2629-38.

Harris GL, Creason MB, Brulte GB, Herr DR. (2012). In vitro and in vivo antagonism of a G protein-coupled receptor (S1P3) with a novel blocking monoclonal antibody. PLoS One. 7(4):e35129.

Ishii I, Friedman B, Ye X, Kawamura S, Mcgiffert C, Contos JJ, Kingsbury MA, Zhang G, Brown JH, Chun J. (2001). Selective Loss of Sphingosine 1-Phosphate Signaling with No Obvious Phenotypic Abnormality in Mice Lacking Its G Protein coupled Receptor, LPB3/EDG-3. J Biol Chem. 276(36):33697-704.

Ishii I, Fukushima N, Ye X, Chun J. (2004). Lysophospholipid Receptors: Signaling and Biology. Annu Rev Biochem. 73:321-54.

Kanno T, Nishizaki T. (2011). Endogenous sphingosine 1-phosphate regulates spontaneous glutamate release from mossy fiber terminals via S1P(3) receptors. Life Sci. 18;89(3-4) :137-40.

Keul P, Lucke S, Von Wnuck Lipinski K, Bode C, Graler M, Heusch G, Levkau B. (2011). Sphingosine-1-phosphate receptors promotes recruitment of monocyte/macrophages in inflammation and atherosclerosis. Circ Res. 108(3):314-23.

Kim ES, Kim JS, Kim SG, Hwang S, Lee CH, Moon A. (2011). Sphingosine 1-phosphate regulates matrix metalloproteinase-9 expression and breast cell invasion through S1P3-Gαq coupling. J Cell Sci. 1; 124(Pt 13):2220-30.

Kono M, Ml Y, Liu Y, Sasaki T, Allende ML, Wu YP, Yamashita T, Proia RL. (2004). The sphingosine-1-phosphate receptors S1P1, S1P2, and S1P3 function coordinately during embryonic angiogenesis. J Biol Chem. 279(28):29361-73.

Kono Y, Nishiuma T, Nishimura Y, Kotani Y, Okada T, Nakamura S, Yokoyama M. (2007). Sphingosine kinase 1 regulates differentiation of human and mouse lung fibroblasts mediated by TGF-betaI. Am J Respir Cell Mol Biol. 37(4):395-404.

Lai WQ, Melendez AJ, Leung BP. (2010). Role of sphingosine kinase and sphingosine-1-phosphate in inflammatory arthritis. World J Biol Chem. 1(11):321-326.

Li C, Jiang X, Yang L, Liu X, Yue S, Li L. 2009. Involvement of sphingosine 1-phosphate (SIP)/S1P3 signaling in cholestasis induced liver fibrosis. Am J Pathol; 175(4):1464-72.

Liliom K, Guan Z, Tseng JL, Desiderio DM, Tigyi G, Watsky MA. Growth factor-like phospholipids generated after corneal injury. (1998). Am J Physiol. 274:C1065-C1074.

Maceyka M, Harikumar KB, Milstien S, Spiegel S. (2012). Sphingosine-1-phosphate signaling and its role in disease. Trends Cell Biol. 22(1):50-60.

Maragakis NJ, Rothstein JD. (2006). Mechanisms of Disease: astrocytes in neurodegenerative disease. Nat Clin Pract Neurol. 2(12):679-89.

Marsolais D, Rosen H. (2009). Chemical modulators of sphingosine-1-phosphate receptors as barrier-oriented therapeutic molecules. Nat Rev Drug Discov. 8(4):297-307.

Means KL, Brown JH. (2009). Cardiov Res_Sphingosine-1-phosphate receptor-signalling in the heart. 82, 193-200.

Mehta D, Konstantoulaki M, Ahmmed GU, Malik AB. (2005). Sphingosine 1-phosphate-induced mobilization of intracellular Ca2+ mediates Rac activation and adherents junction assembly in endothelial cells. J Biol Chem. 280:17320-17328.

Meraz-Rios MA. Toral-Rios D, Franco-Bocanegra D, Villeda-Hernandez J, Campos-Pena V. (2013). Inflammatory process in Alzheimer's Disease. Front Integr Neurosci. 7(59): 1-15.

Mettu P, Deng P, Misra U, Gawdi G, Epstein D, Rao P. (2004). Role of lysophopholipid growth factors in the modulation of aqueous humor outflow facility. Invest. Ophthalmol. Vis. Sci.45:2263-2271.

Murakami A, Takasugi H, Ohnuma S, Koide Y, Sakurai A, Takeda S, Hasegawa T, Sasamori J, Konno T, Hayashi K, Watanabe Y, Mori K, Sato Y, Takahashi A, Mochizuki N, Takakura N. (2010). Sphingosine 1-phosphate (S1P) regulates vascular contraction via S1P3 receptor: investigation based on a new S1P3 receptor antagonist. Mal Pharmacol. 77(4):704-13.

Niessen F, Schaffner F, Furlan-Freguia C, Pawlinski R, Bhattacharjee G, Chun J, Derian CK, Andrade-Gordon P, Rosen H, Ruf W. 2008. Dendritic cell PAR1-S1P3 signalling couples coagulation and inflammation. Nature. 452(7187):654-8.

Pyne S and Pyne JN. (2000). Sphingosine 1-phosphate signalling in mammalian cells. Biochem J. 349, 385-402.

Rosen H, Gonzalez-Cabrera PJ, Sanna MG, Brown S. (2009). Sphingosine 1-phosphate receptor signaling. Annu Rev Biochem. 78:743-68.

Rouach N, Pebay A, Meme W, Cordier J, Ezan P, Etienne E, Giaume C, Tence M. (2006). S1P inhibits gap junctions in astrocytes: involvement of G and Rho GTPase/ROCK. Eur J Neurosci. 23(6):1453-1464.

Sanna MG, Liao J, Jo E, Alfonso C, Ahn MY, Peterson MS, Webb B, Lefebvre S, Chun J, Gray N, Rosen H. (2004). Sphingosine 1-Phosphate (S1P) Receptor Subtypes S1P1 and S1P3, Respectively, Regulate Lymphocyte Recirculation and Heart Rate. J Biol Chem. 279(14):13839-48.

Shea BS, Tager AM. (2012). Sphingolipid Regulation of Tissue Fibrosis. Open Rheumat J. 6(Suppl 1: M8) 123-129.

Singleton PA, Dudek SM, Ma SF, Garcia JG. (2006). Transactivation of sphingosine 1-phosphate receptors is essential for vascular barrier regulation. Novel role for hyaluronan and CD44 receptor family. J Biol Chem. 281(45):34381-93.

Spiegel S, Milstien S. (2003). Exogenous and intracellularly generated sphingosine 1-phosphate can regulate cellular processes by divergent pathways. Biochem Soc Trans. 31(Pt 6):1216-9.

Stamer WD, Read AT, Sumida GM, Ethier CR. (2009). Sphingosine-1-phosphate effects on the inner wall of Schlemm's canal and outflow facility in perfused human eyes. Exp Eye Res. 89(6):980-8.

Sun X, Shikata Y, Wang L, Ohmori K, Watanabe N, Wada J, Shikata K, Birukov KG, Makino H, Jacobson JR, Dudek SM, Garcia JG. (2009). Enhanced interaction between focal adhesion and adherens junction proteins: involvement in sphingosine 1-phosphate-induced endothelial barrier enhancement. Microvasc Res.77:304-313.

Takasugi N, Sasaki T, Suzuki K, Osawa S, Isshiki H, Hori Y, Shimada N, Higo T, Yokoshima S, Fukuyama T, Lee VM, Trojanowski JQ, Tomita T, Iwatsubo T. (2011). BACE1 activity is modulated by cell-associated sphingosine-1-phosphate. J Neurosci. 31(18):6850-7.

Takasugi N, Sasaki T, Ebinuma I, Osawa S, Isshiki H, Takeo K, Tomita T, Iwatsubo T. (2013) FTY720/fingolimod, a sphingosine analogue, reduces amyloid-β production in neurons. PLoS One. May 7, 2013;8(5).

Takuwa N, Ohkura S, Takashima S, Ohtani K, Okamoto Y, Tanaka T, Hirano K, Usui S, Wang F, Du W, Yoshioka K, Banno Y, Sasaki M, Ichi I, Okamura M, Sugimoto N, Mizugishi K, Nakanuma Y, Ishii I, Takamura M, Kaneko S, Kojo S, Satouchi K, Mitumori K, Chun J, Takuwa Y. (2010). S1P3-mediated cardiac fibrosis in sphingosine kinase 1 transgenic mice involves reactive oxygen species. Cardiovasc Res. 85(3):484-93.

Taniguchi M, Kitatani K, Kondo T, Hashimoto-Nishimura M, Asano S, Hayashi A, Mitsutake S, Igarashi Y, Umehara H, Takeya H, Kigawa J, Okazaki T. (2012). Regulation of autophagy and its associated cell death by "sphingolipid rheostat": reciprocal role of ceramide and sphingosine 1-phosphate in the mammalian target of rapamycin pathway. J Biol Chem. 287(47):39898-910.

(56) References Cited

OTHER PUBLICATIONS

Trifilieff A, Fozard JR. (2012). Sphingosine-1-phosphate-induced airway hyper-reactivity in rodents is mediated by the sphingosine-1-phosphate type 3 receptor. J Pharmacol Exp Ther. 342(2):399-406.

Uhlig S, Yang Y. (2013). Sphingolipids in Disease. Handbook of Experimental Pharmacology, Sphingolipids in Acute Lung Injury. vol. 216, pp. 227-246.

Wu YP, Mizugishi K, Bektas M, Sandhoff R, Proia RL. (2008). Sphingosine kinase 1/S1P receptor signaling axis controls glial proliferation in mice with Sandhoff disease. Hum Mol Genet. 17(15):2257-64.

Yamashita H, Kitayama J, Shida D, Yamaguchi H, Mori K, Osada M, Aoki S, Yatomi Y, Takuway, Nagawa H. (2006). Sphingosine 1-phosphate receptor expression profile in human gastric cancer cells: differential regulation on the migration and proliferation. J Surg Res. 130(1):80-7.

Yin Z, Fan L, Wei L, Gao H, Zhang R, Tao L, Cao F, Wang H. (2012). FTY720 protects cardiac microvessels of diabetes: a critical role of S1P1/3 in diabetic heart disease. PLoS One. 7(8):e42900.

Young N and Van Brooklyn JR. (2007). Roles of Sphingosine-1-Phosphate (S1P) Receptors in Malignant behavior of Glioma Cells. Differential Effects of S1P2 on Cell Migration and Invasiveness. Exp Cell Res. I; 313(8): 1615-1627.

Zhang YH, Fehrenbacher JC, Vasko MR, Nicoll GD. (2006). Sphingosine-1-Phosphate via Activation of a G-Protein-Coupled Receptor(s) Enhances the Excitability of Rat Sensory Neurons. J Neurophysiol. 96: 1042-1052.

Feb. 6, 2017 Office Action issued by the Eurasian Patent Office in connection with Eurasian Patent Application No. 201691160 (including English Language translation).

Mar. 12, 2014 European Search Report issued by the European Patent Office in connection with European Patent Application No. 13195372.1.

First Office Action issued by the Colombian Patent Office in connection with Colombian Patent Application No. NC2016/0000025.

Jan. 30, 2017 Response to First Office Action issued by the Colombian Patent Office in connection with Colombian Patent Application No. NC2016/0000025.

Feb. 7, 2018 First Office Action issued in connection with Chinese Patent Application No. CN 201480074769.6 (including English language translation).

Hemmati, Fatemeh. Behavioural Brai Research 252 (2013) 415-421.

UCSF Medical Center. Neurological Disorders. (2016) Web: <https://www.ucsfhealth.org/conditions/neurological_disorders/>.

MedicineNet.com (2004) Web: <http://www.medterms.com>.

* cited by examiner

S1P3 ANTAGONISTS

CROSS-REFERENCE TO RELATED APPLICATIONS

This application is a continuation of U.S. Ser. No. 15/923,837, filed Mar. 16, 2018, a continuation of U.S. Ser. No. 14/100,326, filed May 30, 2016, now U.S. Pat. No. 9,951,017, issued Apr. 24, 2018, which is a § 371 national stage of PCT International Application No. PCT/EP2014/076986, filed Nov. 28, 2014, claiming priority of European Patent Application No. EP 13195372.1, filed Dec. 2, 2013, the entire contents of each of which in their entireties are hereby incorporated by reference.

The present invention relates to novel antagonists of the S1P3 receptor of formula (A) as herein described and to their pharmaceutical uses.

Such antagonists can be used for the treatment of inflammation-related diseases such as arthritis, fibrosis, inflammatory syndromes, atherosclerosis, vascular diseases, asthma, bradycardia, acute lung injury, lung inflammation, cancer, ocular hypertension, glaucoma, neuroinflammatory diseases, Sandhoff's disease, kidney ischemia-reperfusion injury, pain, diabetic heart disease and neurodegenerative diseases such as Alzheimer's disease, Parkinson's disease, Amyotrophic lateral sclerosis, Huntington's disease or Multiple Sclerosis.

BACKGROUND OF THE INVENTION

The S1P3 receptor gene encodes for a member of the endothelial differentiation gene (EDG) family of receptors widely present in central and peripheral human tissues (Rosen et al., 2009; Ishii et al., 2001). $S1P_3$ receptor (also called: EDG3; LPB3; S1PR3; EDG-3) belong to a class of five ($S1P_{1-5}$) seven-spanning membrane proteins belonging to the class of G-Protein-Coupled Receptors (GPCRs), whose natural ligand is the bioactive lipid sphingosine-1-phosphate (S1P) (Chun et al., 2002). S1P is involved in a large array of cellular responses modulating several physiological processes such as innate immunity, wound healing, vascular endothelial cell functions, inflammatory response and others (Ishii et al., 2004; Brinkmann, 2007; Rosen et al., 2009; Maceyka et al., 2012). S1P is intracellularly produced, with the direct role of secondary messenger (Spiegel and Milstien, 2003), and extracellularly exported acting to S1P cell membrane receptors as endogenous ligand.

The S1P receptors expressed in many apparatuses are able to trigger signalling through a variety of heterotrimeric G proteins, including Gi/o, G12/13, and Gq. In the $S1P_{1-5}$ receptors family, $S1P_3$ has been shown to be functionally relevant in several physiological processes such as regulations of heart rate, angiogenesis and vascular contraction (Forrest et al., 2004; Sanna et al., 2004; Marsolais and Rosen, 2009; Means and Brown, 2009; Murakami et al., 2010), in embryonic angiogenesis development (Kono et al., 2004) or as autophagy modulator (Taniguchi et al., 2012). The $S1P_3$ receptor is also deeply involved in immunological processes (Brinkmann V. (2009). Importantly, mice lacking $S1P_3$ receptor did not show evident abnormalities indicating a non-essential role of the receptor for a normal animal development (Ishii et al., 2001). As mentioned, S1P plays an important role as essential modulator of innate immunity and inflammation inducer. S1P once produced and released as signalling molecule by a wide range of cell types or even non-nucleated cells (e.g. platelets) (Pyne and Pyne, 2000) can exert an important role in inflammation. As introduced, together with the whole S1P receptor family, $S1P_3$ receptor system has been largely studied focusing on its role in disease and has been shown to be involved in a large number of pathologies. From the literature $S1P_3$ emerges as an important target implicated in pathologies with inflammatory components, in this case a pharmacological inhibition of the receptor could potentially counteract the disease evolution. The $S1P_3$ receptor appears to be an appealing target also for other therapeutic areas, in which a potential healing role of $S1P_3$ antagonism has been demonstrated.

$S1P_3$ Antagonism in Peripheral Diseases $S1P_3$ activity has been shown to be implicated in inflammation-associated diseases such as arthritis (Lai et al., 2010), and several type of fibrosis (Shea and Tager, 2012) like heart (Takuwa et al., 2010), pulmonary (Kono et al., 2007), muscular (Cencetti et al., 2008) and liver fibrosis (Li et al., 2009) or in other more general inflammatory syndromes (Niessen et al., 2008) where $S1P_3$ receptor antagonism could potentially limit the pathologic processes.

$S1P_3$ receptor activation in the cardiovascular system could exert several pathologically-relevant effects. In the blood the S1P released by activated platelets stimulates $S1P_3$ (and $S1P_1$) receptors in vascular endothelium decreasing vascular para-cellular permeability (Mehta et al. 2005; Sun et al. 2009). Additionally, $S1P_3$ transactivation has been shown to disrupt vascular barrier regulation (Singleton et al., 2006). Furthermore, also the chemotactic effect of S1P in macrophages (demonstrated in vitro and in vivo) is mediated by $S1P_3$, so playing a causal role in atherosclerosis by promoting the recruitment of inflammatory monocyte/macrophage and altering vessel smooth muscle cells behaviour (Keul et al., 2011). Finally, the group of Takakura has demonstrated by a specific antagonist that the S1P-induced coronary flow decrease is dependent on $S1P_3$ receptor and so such antagonism might be adapt to counteract S1P related vascular diseases and vasospasm syndromes (Murakami et al., 2010). In the heart, interestingly, the sustained bradycardia induced by S1P receptor non-selective agonists is abolished in $S1P_3$ knockout mice or after $S1P_3$ pharmacological inhibition in rats (Sanna et al., 2004; Murakami et al., 2010). More, in the cardiac vascular microcirculation cells in diabetes, it has been shown in vivo and in vitro that the agonist FTY720 exerts a functional antagonism by stimulating the translocation of S1P3 from membrane to the nucleus. Arguably, the pharmacological modulation of $S1P_3$ receptors could be beneficial to alleviate cardiac microangiopathy in diabetes (Yin et al., 2012).

Bajwa et al. (2012) have demonstrated that S1P plays a pivotal role in kidney ischemia-reperfusion injury (IRI). $S1P_3$ receptor-deficient mice were protected from IRI. This protective effect was due, at least in part to differences between $S1P_3$-deficient dendritic cells. It was then supposed that pharmacological treatment are able to limit $S1P_3$ activity or treatments with dendritic cells lacking the S1P3 receptor could help against progression of IRI.

Also several physiological parameters of the respiratory system are affected by $S1P_3$ activity. It has been recently demonstrated that the S1P pathway activation induced a generalized airway hyperreactivity in vivo and in vitro and this is mediated by $S1P_3$ receptor. Then, the $S1P_3$ antagonism, besides or contextually to the abovementioned putative healing effects on lung fibrosis, could represent a new therapeutic strategy aimed at blocking the asthma-related airway hyperreactivity (Trifilieff and Fozard, 2012). $S1P_3$ has been also shown to be strictly involved in acute lung injury where it promotes chemotaxis and increased endothelial and epithelial permeability (Uhlig and Yang, 2013). In the publication of Chen et al., (2008) it is suggested that S1P acting through S1P$_3$, increasing calcium influx, and Rho kinase, activates cPLA(2)alpha and releases arachidonic acid in lung epithelial cells. Then, understanding this mechanism in lung epithelial cells may provide potential targets to control inflammatory processes in the lung.

S1P$_3$ receptors play an important role in other non-inflammatory diseases. In cancer, it has been shown that S1P$_3$ activation promotes breast cancer cells invasiveness (Kim et al., 2011) and this effect can be diminished by a specific antibody able to block the receptor (Harris et al., 2012). Similar results were obtained in thyroid cancer cells (Balthasar et al., 2006) and glioma cells (Young et al., 2007), where S1P$_3$ activation showed to enhance cell migration and invasion. Yamashita (2006) also demonstrated that S1P$_3$-mediated signals might be crucial in determining the metastatic response of gastric cancer cells to S1P.

In the eye, considering that S1P is constitutively present in the aqueous humor (Liliom et al., 1998), and, in addition, that the endothelial cells of the trabecular meshwork, which express S1P$_1$ and S1P$_3$ receptors (Mettu et al., 2004), respond to S1P stimulus increasing the outflow resistance, the S1P$_3$ receptors pharmacological inhibition represents a potential therapeutic strategy in healing pathologies involving high intraocular pressure such as ocular hypertension, glaucoma, glaucomatous retinopathy (Stamer et al., 2009).

S1P$_3$ Antagonism in PNS Diseases

The tissue injury inflammation is associated with an increased sensitivity to noxious stimuli, suggesting that there could be an important interaction between the activities of immune cells and the sensory neurons activated by noxious stimulation. A direct exposure of isolated sensory neurons to S1P (together with other inflammatory signals released by platelets or mast cells) increases their action potential firing through activation of ion channels (Zhang et al., 2006). In experimental conditions of isolated sensory neurons, the expression of S1P3 receptors is the highest in the panel of S1P receptors. In addition, the Kress's laboratory has demonstrated that S1P3 receptor was detected in all human and mouse dorsal root ganglia neurons and that S1P evokes significant nociception via G-protein-dependent activation of an excitatory chloride conductance (Camprubí-Robles et al., 2013). Considering that S1P-induced neuronal responses and spontaneous pain behavior in vivo were strongly reduced in S1P3-null mice, S1P3 receptors could represent important therapeutic targets for post-traumatic pain (Camprubí-Robles et al., 2013).

S1P3 Antagonism in CNS Diseases

In the CNS, neurons, astrocytes, oligodendrocytes and microglia cells have the capacity to produce and secrete S1P and express, with different extents depending on the cell type, S1P$_{1-3}$ and S1P$_5$ receptors (Anelli et al., 2005; Foster et al., 2007). In regard to S1P$_3$ receptor, an intrinsic high expression has been seen in both astrocytes and neurons (Foster et al., 2007). S1P$_3$ is described to induce glial activation under pro-inflammatory conditions (Fisher et al., 2011; Wu et al., 2008) and enhance spontaneous glutamate release in the hippocampus mossy fibers (Kanno and Nishizaki, 2011). In particular, apoptotic neurons self-induce an overexpression of sphingosine-kinase with a further release of S1P. This process, elegantly demonstrated by Gude (Gude et al., 2008) and defined as "come-and-get-me" signal, has the purpose of chemo-attract microglial cells and eliminate the dying neuron. Furthermore, S1P through a G12/13 protein, by remodelling of actin cytoskeleton, can inhibit astrocytes tight junction, conferring them mobility, and creating gaps through the brain tissue (Rouach et al., 2006). Then, the action of S1P to astrocytes could help the activated microglial cells to better move in the brain and so express their phagocytic role. The S1P$_3$ receptors coupling to the G12/13 protein, associated to a high S1P$_3$ receptor expression in astrocytes and its role in motility (Fischer et al., 2011) leaded to the consideration that the described process could be conducted by a S1P$_3$-activated signalling. Interestingly, microglial cells, once activated, enhance their S1P$_3$ expression (Foster et al., 2007). With these evidences it was conceivably hypothesised that activation of S1P$_3$ receptor system is strictly involved in a neuroinflammatory state and S1P$_3$ inhibition could have limited its development. Evidence supporting S1P$_3$ antagonism to be protective in neuroinflammation was given from a mouse model of Sandhoff disease in which the ablation of the gene encoding S1P$_3$ receptor strongly limited the astroglial proliferation, prolonging the survival and improving motor function of the mice (Wu et al., 2008).

In neurodegenerative diseases neuroinflammation can play a clear detrimental role during the pathologic evolution Alzheimer's, Parkinson's, Amyotrophic lateral sclerosis, Huntington and Multiple sclerosis (Bradl and Hohlfeld, 2003; Maragakis and Rothstein, 2006; Davies et al., 2013). In Alzheimer disease (AD) the accumulation of beta-amyloid plaques has been associated to inflammation development with activation of the CNS immune system (Meraz-Rios et al., 2013). A relevance of S1P receptors activity and modulation in AD is also shown in Takasugi et al., 2011 and in Takasugi et al., 2013

PRIOR ART

EP81756 discloses compounds that are useful for treating inflammation.

Wang et al. (Bioorganic & Medicinal Chemistry Letters (2010), 20(2), 493-498) disclose compounds that are FFA2 inhibitors useful for the treatment of diabetes.

WO2000026202 discloses antiproliferative compounds that are useful for the treatment of cancer.

WO2003063797 discloses potassium channel inhibitors that are useful for the treatment of arrhythmia.

JP2002155065 discloses compounds that are useful as insecticides or miticides.

WO2001036415 discloses compounds that are useful for controlling pests on domestic animals and livestock.

In WO2005075435, WO2007087066, WO2008141119, WO2008147797, WO2009006315, WO2009123896 and WO2010054138, Vertex discloses compounds as CFTR modulators for the treatment of cystic fibrosis or as intermediates towards such compounds.

Ingyong Huaxue (1990), 7(6), 54-7 discloses pesticides and fungicides.

The following disclose activators of glucokinase useful for the treatment of diabetes: Journal of Medicinal Chemistry (2012), 55(3), 1318-1333; WO2009140624; US-20100063063; Journal of Medicinal Chemistry (2012), 55(16), 7021-7036; Medicinal Chemistry Letters (2013), 4(4), 414-418; US-20010039344; WO2001083465; WO2003095438; WO2004052869; WO2006058923; WO2007026761; WO2007041365; WO2008005914; WO2008078674; WO2008119734; WO2009091014; U.S. Pat. No. 6,610,846; Journal of Medicinal Chemistry (2010), 53(9), 3618-3625; WO2002046173; US20070281942; US2010063063.

Figure 2:
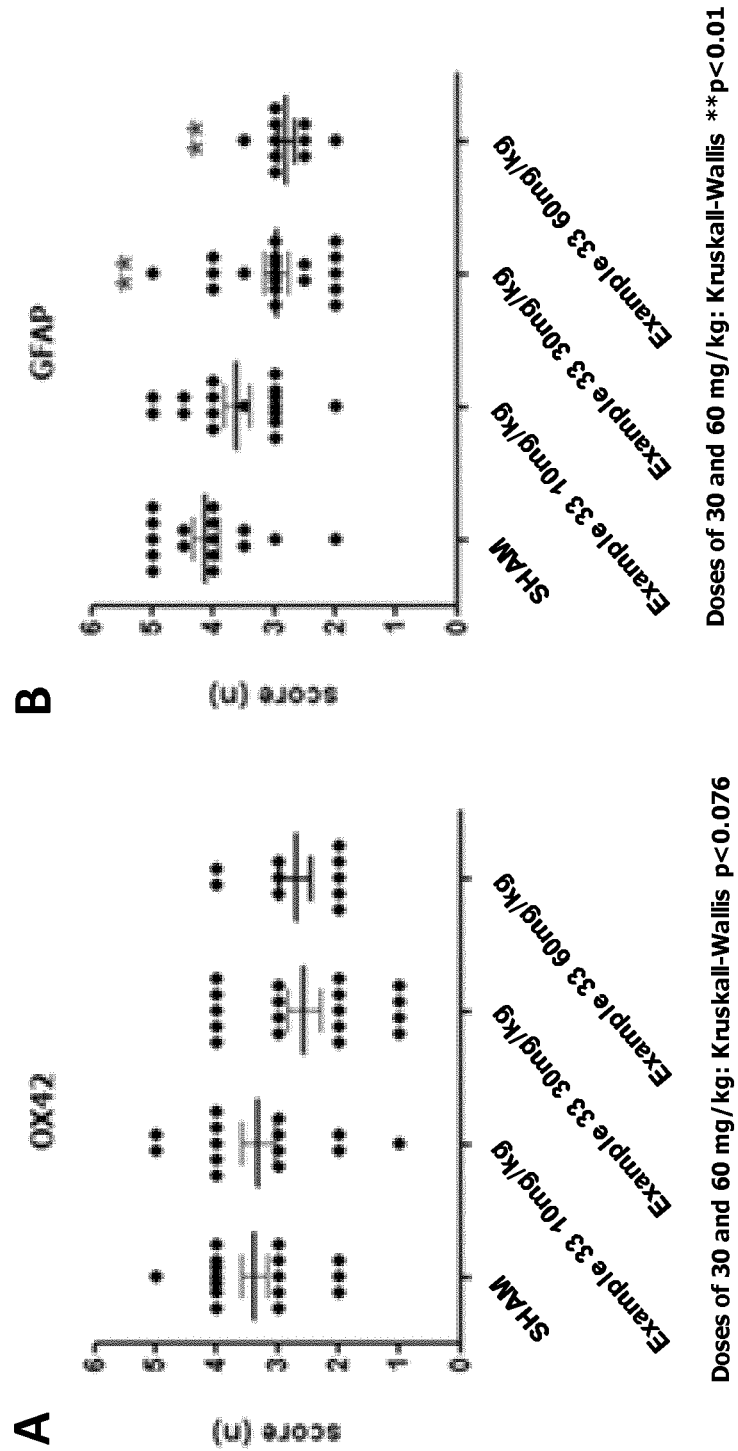

FIG. 2: Anti-neuroinflammatory effect of a compound on quisqualic acid lesioned rats. Example 33 has a strong activity on GFAP reactivity at 30 and 60 mg/Kg/day. A) effect on microglia cells, OX42 analysis; B) effect on astrocytes, GFAP analysis. These evidences are in line with the literature, in which the expression of S1P3 on microglia is considered low and not relevant (S1P2 is predominant), while the receptor appears to be highly expressed in astrocytes.

Figure 3:
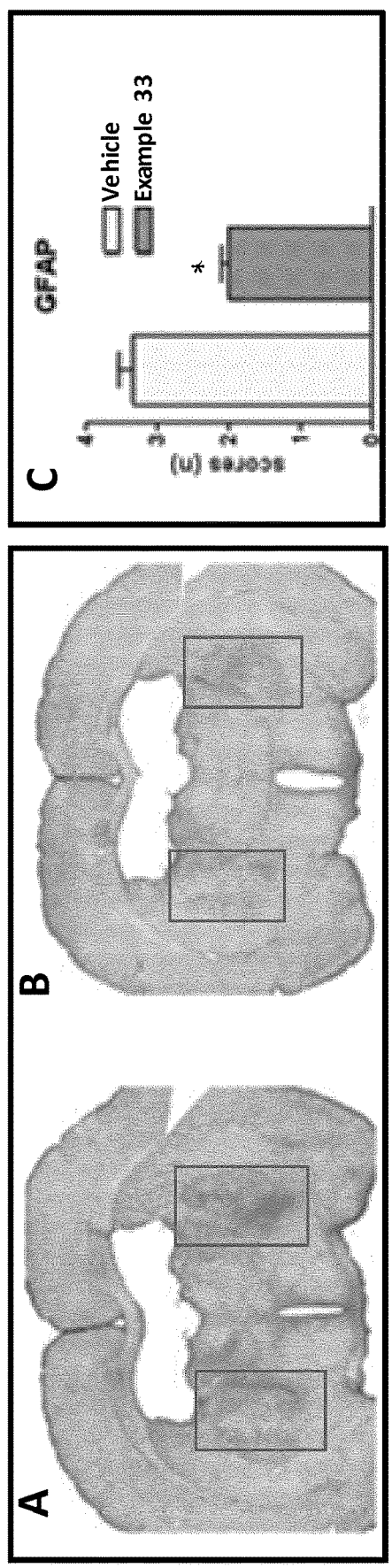

FIG. 3: Effect of a compound of the invention on Abeta (25-35) lesioned rats. Microscope scanning (GFAP staining) A) Ab (23-35) (right hemisphere)+Vehicle B) Ab(25-35) (right hemisphere)-example 33 at 30 mg/kg (left hemisphere was Sham-treated). C) quantitative analysis of GFAP-positive cells by visual scoring (*p<0.05 vs vehicle group, Kruskall-Wallis).

Figure 4:
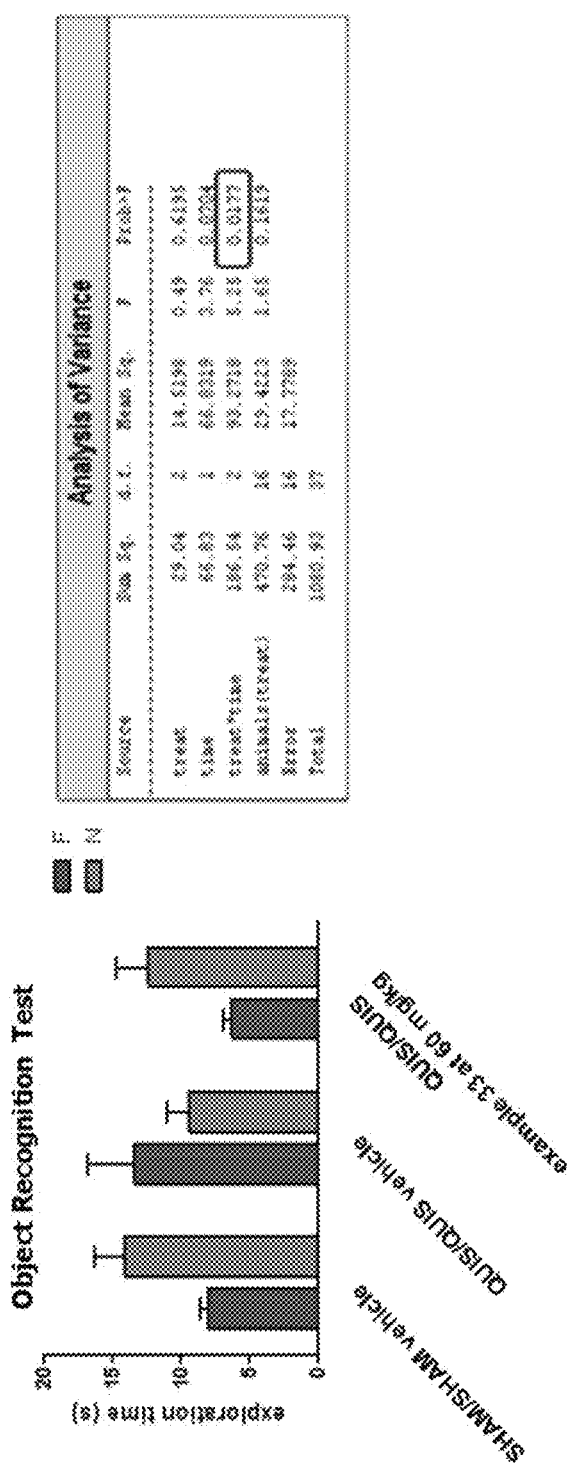

FIG. 4: Effect of a compound of the invention in the Object Recognition Test on quisqualic acid lesioned rats. Treatment with example 33 significantly ameliorates cognitive functions in ORT measuring episodic memory in Quisqualic lesioned rats as reported in the table of ANOVA (right panel). To note the difference in the exploration time between familiar and novel objects (F=familiar object, N=novel object).

DETAILED DESCRIPTION OF THE INVENTION

In a first aspect of this invention (embodiment A), there is provided compounds of formula (A),

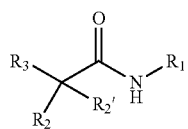

(A)

wherein

•-$R_1$ is

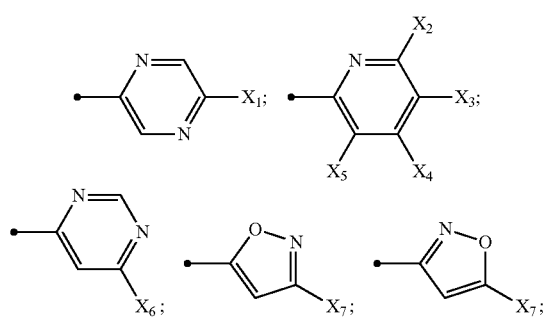

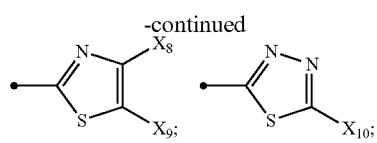

-continued $X_1$, $X_6$, $X_7$, $X_9$ and $X_{10}$ are halogen, $C_1$-$C_4$ linear branched or cyclic alkyl optionally substituted with one or more fluorine atoms;

$X_2$, $X_3$, $X_4$, $X_5$ and $X_8$, are hydrogen, halogen, $C_1$-$C_4$ linear branched or cyclic alkyl optionally substituted with one or more fluorine atoms;

with the proviso that at least one of $X_2$, $X_3$, $X_4$, and $X_5$ is not hydrogen;

$R_2$ is a $C_3$-$C_6$ linear branched or cyclic alkyl optionally substituted with phenyl, with one or more fluorine atoms or with trifluoromethyl-furanyl;

$R_2'$ is hydrogen, F, $C_1$-$C_3$ linear or branched alkyl optionally substituted with one or more fluorine atoms;

or $R_2$ and $R_2'$ together with the carbon atom they are attached to form a $C_3$-$C_6$ cycloalkyl ring;

•-$R_3$ is

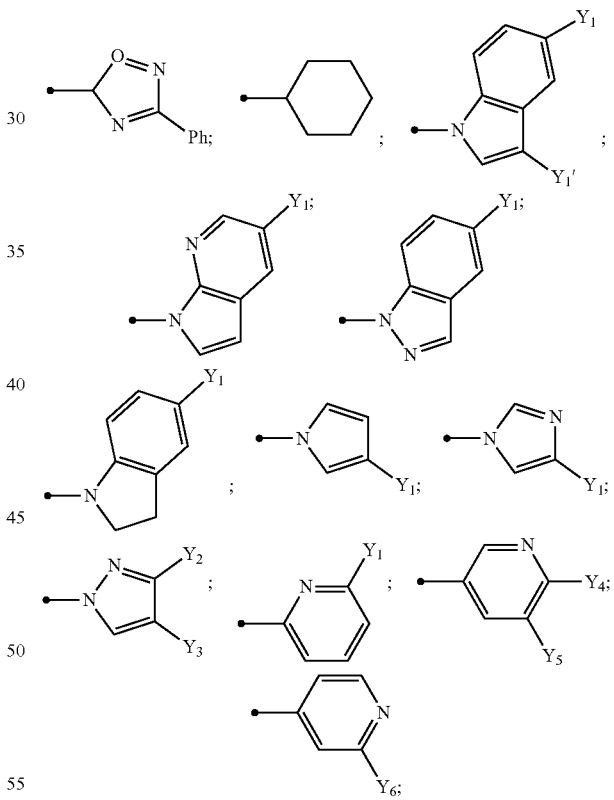

$Y_1$ is halogen;

$Y_1'$ is $C_1$-$C_3$ linear branched or cyclic alkyl optionally substituted with one or more fluorine atoms;

$Y_2$ is cyano or methoxyphenyl, $C_1$-$C_3$ linear branched or cyclic alkyl optionally substituted with one or more fluorine atoms;

$Y_3$ is hydrogen, halogen or methoxyphenyl;

$Y_4$ is hydrogen, halogen, N-methylpyrazolyl or a $C_1$-$C_3$ linear branched or cyclic alkoxy optionally substituted with one or more fluorine atoms, $Y_5$ is hydrogen, halogen, cyano, or a $C_1$-$C_3$ linear branched or cyclic alkyl optionally substituted with one or more fluorine atoms;
with the proviso that at least one of $Y_4$ and $Y_5$ is not hydrogen;
$Y_6$ is halogen, $C_1$-$C_3$ linear branched or cyclic alkyl optionally substituted with one or more fluorine atoms, or a $C_1$-$C_3$ linear branched or cyclic alkoxy optionally substituted with one or more fluorine atoms;
enantiomers, enantiomerically enriched mixtures, and pharmaceutically acceptable salts thereof.

Under one aspect of embodiment A (embodiment A1), there is provided compounds of formula (A) wherein halogen is selected from the list of Cl, Br and F;
$C_1$-$C_4$ linear branched or cyclic alkyl optionally substituted with one or more fluorine atoms is selected from the list of methyl, trifluoromethyl, n-propyl and t-butyl;
$C_1$-$C_3$ linear branched or cyclic alkyl optionally substituted with one or more fluorine atoms is selected from the list of methyl, trifluoromethyl and n-propyl; $C_1$-$C_3$ linear branched or cyclic alkoxy optionally substituted with one or more fluorine atoms is selected from the list of methoxy and difluoromethoxy;
$C_3$-$C_6$ linear branched or cyclic alkyl optionally substituted with phenyl, with one or more fluorine atoms or with trifluoromethyl-furanyl is selected from n-propyl,3-phenyl-n-propyl i-propyl, n-butyl, cyclohexyl and (5-trifluoromethyl-furan-2yl)-methyl;
$C_3$-$C_6$ cycloalkyl is selected from the list of cyclobutyl and cyclopentyl;

Under another aspect of embodiment A (embodiment A2), there is provided compounds of formula (A) wherein halogen is selected from the list of Cl, Br and F;
$C_1$-$C_4$ linear branched or cyclic alkyl optionally substituted with one or more fluorine atoms is selected from the list of methyl, trifluoromethyl and t-butyl; $C_1$-$C_3$ linear branched or cyclic alkyl optionally substituted with one or more fluorine atoms is selected from the list methyl and trifluoromethyl;
$C_1$-$C_3$ linear branched or cyclic alkoxy optionally substituted with one or more fluorine atoms is selected from the list of methoxy and difluoromethoxy;
$C_3$-$C_6$ linear branched or cyclic alkyl optionally substituted with phenyl, with one or more fluorine atoms or with trifluoromethyl-furanyl is selected from n-propyl,3-phenyl-n-propyl i-propyl, n-butyl, cyclohexyl and (5-trifluoromethyl-furan-2yl)-methyl;
$C_3$-$C_6$ cycloalkyl is selected from list of cyclobutyl and cyclopentyl;

Under another aspect of embodiment A (embodiment A3), there is provided compounds of formula (A) wherein $R_1$ and $R_3$ are as described under embodiment A and wherein
$X_1$ is halogen
$X_2$ is hydrogen, halogen or methyl
$X_3$ is hydrogen, halogen or trifluoromethyl
$X_4$ is hydrogen or methyl
$X_5$ is hydrogen or halogen
with the proviso that at least one of $X_2$, $X_3$, $X_4$, and $X_5$ is not hydrogen
$X_6$ is halogen
$X_7$ is t-butyl or trifluoromethyl, preferably t-butyl
$X_8$ is hydrogen, methyl or t-butyl
$X_9$ is halogen
$X_{10}$ is t-butyl
$R_2$ is n-propyl, 3-phenyl-n-propyl, i-propyl, n-butyl, cyclohexyl or (5-trifluoromethyl-furan-2yl)-methyl
$R_2'$ is hydrogen, F, methyl or $R_2$ and $R_2'$ together with the carbon atom they are attached to form a cyclobutyl or cyclopentyl ring;
$Y_1$ is halogen
$Y_1'$ is methyl
$Y_2$ is methyl, n-propyl, cyano, trifluoromethyl or 4-methoxyphenyl
$Y_3$ is hydrogen, halogen, or 4-methoxyphenyl
$Y_4$ is hydrogen, halogen, methoxy or 1-methyl-pyrazol-4-yl
$Y_5$ is hydrogen, halogen, cyano or methyl
with the proviso that at least one of $Y_4$ and $Y_5$ is not hydrogen
$Y_6$ halogen, methoxy or difluoromethoxy Under another aspect of embodiment A (embodiment A4), there is provided compounds of formula (A) wherein $R_1$ and $R_3$ are as described under embodiment A and wherein
$X_1$ is Cl or Br
$X_2$ is hydrogen, methyl, Br or F
$X_3$ is hydrogen, Br, Cl, F, or trifluoromethyl
$X_4$ is hydrogen or methyl
$X_5$ is hydrogen or F
with the proviso that at least one of $X_2$, $X_3$, $X_4$, and $X_5$ is not hydrogen
$X_6$ is Cl
$X_7$ is t-butyl or trifluoromethyl, preferably t-butyl
$X_8$ is hydrogen, methyl or t-butyl
$X_9$ is Br, Cl or F
$X_{10}$ is t-butyl
$R_2$ is n-propyl, 3-phenyl-n-propyl, i-propyl, n-butyl, cyclohexyl or (5-trifluoromethyl-furan-2yl)-methyl;
$R_2'$ is hydrogen, F, methyl;
or $R_2$ and $R_2'$ together with the carbon atom they are attached to form a cyclobutyl or cyclopentyl ring;
$Y_1$ is Br
$Y_1'$ is methyl
$Y_2$ is methyl, n-propyl, cyano, trifluoromethyl and 4-methoxyphenyl
$Y_3$ is hydrogen, Br, Cl, and 4-methoxyphenyl
$Y_4$ is hydrogen, Br, Cl, methoxy or 1-methyl-pyrazol-4-yl
$Y_5$ is hydrogen, Br, Cl, F, cyano or methyl
with the proviso that at least one of $Y_4$ and $Y_5$ is not hydrogen
$Y_6$ is Br, Cl, F, methoxy or difluoromethoxy Under specific aspects of embodiments A, A1, A2, A3 or A4 (embodiments B1) there is provided compounds of formula (A) wherein •-$R_1$ is selected from

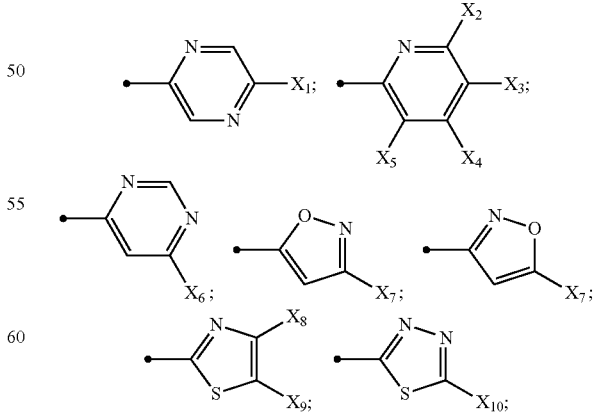

and wherein $R_2$, $R_2'$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiment A, A1, A2, A3 or A4

Under specific aspects of embodiments A, A1, A2, A3 or A4 (embodiments B2) there is provided compounds of formula (A) wherein •-R₁ is selected from

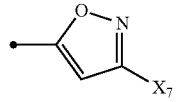

and wherein R₂, R₂', R₃, X₇, Y₁, Y₁', Y₂, Y₃, Y₄, Y₅ and Y₆ are, as the case may be, as defined under embodiment A, A1, A2, A3 or A4

Under specific aspects of embodiments A, A1, A2, A3 or A4 (embodiments B3) there is provided compounds of formula (A) wherein •-R₁ is selected from

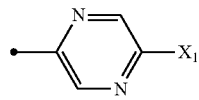

and wherein R₂, R₂', R₃, X₁, Y₁, Y₁', Y₂, Y₃, Y₄, Y₅ and Y₆ are, as the case may be, as defined under embodiment A, A1, A2, A3 or A4

Under specific aspects of embodiments A, A1, A2, A3 or A4 (embodiments B4) there is provided compounds of formula (A) wherein •-R₁ is selected from

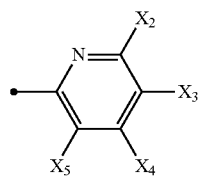

and wherein R₂, R₂', R₃, X₂, X₃, X₄, X₅, Y₁, Y₁', Y₂, Y₃, Y₄, Y₅ and Y₆ are, as the case may be, as defined under embodiment A, A1, A2, A3 or A4

Under a particular aspect of embodiments B4 (embodiments B4a), there is provided compounds of formula (A) wherein X₂ and X₄ are hydrogen
and wherein R₁, R₂, R₂', R₃, X₃, X₅, Y₁, Y₁', Y₂, Y₃, Y₄, Y₅ and Y₆ are, as the case may be, as defined under embodiments B4.

Under another particular aspect of embodiments B4 (embodiments B4b), there is provided compounds of formula (A) wherein X₂, X₄ and X₅ are hydrogen and wherein R₁, R₂, R₂', R₃, X₃, Y₁, Y₁', Y₂, Y₃, Y₄, Y₅ and Y₆ are, as the case may be, as defined under embodiments B4.

Under specific aspects of embodiments A, A1, A2, A3 or A4 (embodiments B5) there is provided compounds of formula (A) wherein •-R₁ is selected from

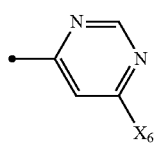

and wherein R₂, R₂', R₃, X₆, Y₁, Y₁', Y₂, Y₃, Y₄, Y₅ and Y₆ are, as the case may be, as defined under embodiment A, A1, A2, A3 or A4

Under specific aspects of embodiments A, A1, A2, A3 or A4 (embodiments B6) there is provided compounds of formula (A) wherein •-R₁ is selected from

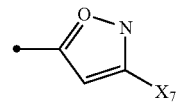

and wherein R₂, R₂', R₃, X₇, Y₁, Y₁', Y₂, Y₃, Y₄, Y₅ and Y₆ are, as the case may be, as defined under embodiment A, A1, A2, A3 or A4

Under specific aspects of embodiments A, A1, A2, A3 or A4 (embodiments B7) there is provided compounds of formula (A) wherein •-R₁ is selected from

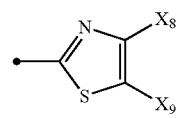

and wherein R₂, R₂', R₃, X₈, X₉, Y₁, Y₁', Y₂, Y₃, Y₄, Y₅ and Y₆ are, as the case may be, as defined under embodiment A, A1, A2, A3 or A4

Under specific aspects of embodiments A, A1, A2, A3 or A4 (embodiments B8) there is provided compounds of formula (A) wherein •-R₁ is selected from

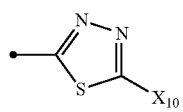

and wherein R₂, R₂', R₃, X₁₀, Y₁, Y₁', Y₂, Y₃, Y₄, Y₅ and Y₆ are, as the case may be, as defined under embodiment A, A1, A2, A3 or A4

Under specific aspects of embodiments A, A1, A2, A3, A4, B1, B2, B3, B4, B4a, B4b, B5, B6, B7 or B8 (embodiments C1) there is provided compounds of formula (A) wherein •-R₃ is selected from

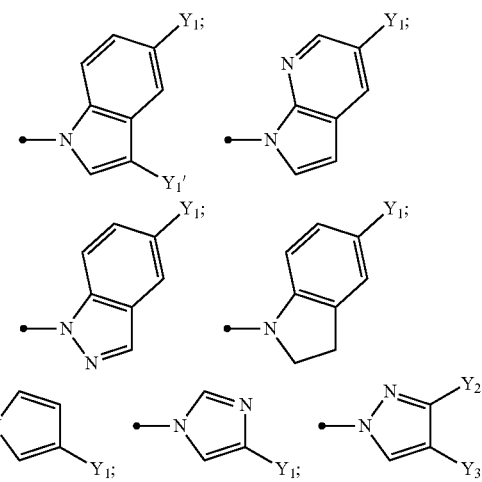

and wherein $R_1, R_2, R_2', X_1, X_2, X_3, X_4, X_5, X_6, X_7, X_8, X_9, X_{10}, Y_1, Y_2$, and $Y_3$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C2) there is provided compounds of formula (A) wherein •-$R_3$ is selected from

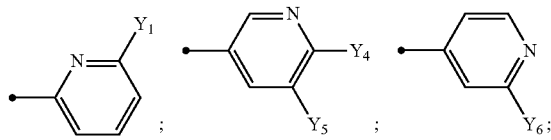

and wherein $R_1, R_2, R_2', X_1, X_2, X_3, X_4, X_5, X_6, X_7, X_8, X_9, X_{10}, Y_1, Y_4, Y_5$, and $Y_6$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C3) there is provided compounds of formula (A) wherein •-$R_3$ is selected from

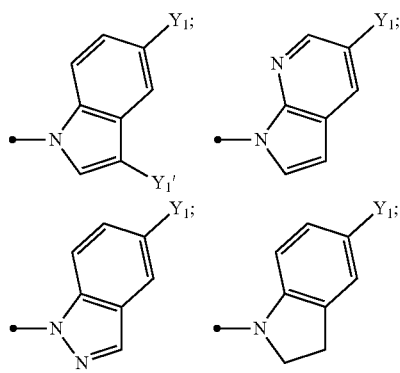

and wherein $R_1, R_2, R_2', X_1, X_2, X_3, X_4, X_5, X_6, X_7, X_8, X_9, X_{10}, Y_1, Y_1', Y_4, Y_5$, and $Y_6$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C4) there is provided compounds of formula (A) wherein •-$R_3$ is selected from

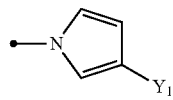

and wherein $R_1, R_2, R_2', X_1, X_2, X_3, X_4, X_5, X_6, X_7, X_8, X_9, X_{10}$ and $Y_1$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C5) there is provided compounds of formula (A) wherein •-$R_3$ is selected from

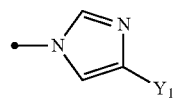

and wherein $R_1, R_2, R_2', X_1, X_2, X_3, X_4, X_5, X_6, X_7, X_8, X_9, X_{10}$ and $Y_1$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C6) there is provided compounds of formula (A) wherein •-$R_3$ is selected from

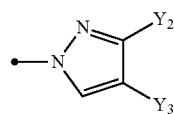

and wherein $R_1, R_2, R_2', X_1, X_2, X_3, X_4, X_5, X_6, X_7, X_8, X_9, X_{10}, Y_2$ and $Y_3$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C7) there is provided compounds of formula (A) wherein •-$R_3$ is selected from

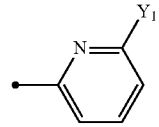

and wherein $R_1, R_2, R_2', X_1, X_2, X_3, X_4, X_5, X_6, X_7, X_8, X_9, X_{10}$ and $Y_1$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C8) there is provided compounds of formula (A) wherein •-$R_3$ is selected from

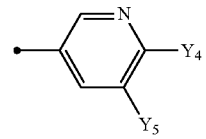

and wherein $R_1, R_2, R_2', X_1, X_2, X_3, X_4, X_5, X_6, X_7, X_8, X_9, X_{10}$ and $Y_4$ and $Y_5$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C9) there is provided compounds of formula (A) wherein •-$R_3$ is selected from

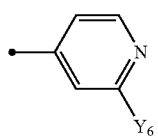

and wherein $R_1$, $R_2$, $R_2'$, $X_1$, $X_2$, $X_3$, $X_4$, $X_5$, $X_6$, $X_7$, $X_8$, $X_9$, $X_{10}$ and $Y_6$ are, as the case may be, as defined under embodiments A, A1, A2, A3, A4, B1, B2, B3, B4, B4a, B4b, B5, B6, B7 or B8

Under specific aspects of embodiments A, A1, A2, A3, A4, B1, B2, B3, B4, B4a, B4b, B5, B6, B7 or B8 (embodiments C10) there is provided compounds of formula (A) wherein •-$R_3$ is selected from

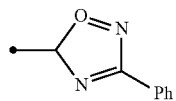

and wherein $R_1$, $R_2$, $R_2'$, $X_1$, $X_2$, $X_3$, $X_4$, $X_5$, $X_6$, $X_7$, $X_8$, $X_9$ and $X_{10}$ are, as the case may be, as defined under embodiments A, A1, A2, A3, A4, B1, B2, B3, B4, B4a, B4b, B5, B6, B7 or B8.

Under specific aspects of embodiments A, A1, A2, A3, A4, B1, B2, B3, B4, B4a, B4b, B5, B6, B7 and B8 (embodiments C11) there is provided compounds of formula (A) wherein •-$R_3$ is selected from

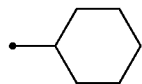

and wherein $R_1$, $R_2$, $R_2'$, $X_1$, $X_2$, $X_3$, $X_4$, $X_5$, $X_6$, $X_7$, $X_8$, $X_9$ and $X_{10}$ are, as the case may be, as defined under embodiments A, A1, A2, A3, A4, B1, B2, B3, B4, B4a, B4b, B5, B6, B7 or B8.

Under specific aspects of embodiments A, A1, A2, A3, A4, B1, B2, B3, B4, B4a, B4b, B5, B6, B7, B8, C1, C2, C3, C4, C5, C6, C7, C8, C9, C10 and C11 (embodiments D1) there is provided compounds of formula (A) wherein $R_2$ and $R_2'$ do not form a cycloalkyl ring together with the carbon atom they are attached to.
and wherein $R_1$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments A, A1, A2, A3, A4, B1, B2, B3, B4, B4a, B4b, B5, B6, B7, B8, C1, C2, C3, C4, C5, C6, C7, C8, C9, C10 or C11.

Under particular aspects of embodiments D1 (embodiments D1a), there is provided compounds of formula (A) wherein $R_2'$ is hydrogen and wherein $R_1$, $R_2$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments D1.

Under other particular aspects of embodiments D1 (embodiments D1b), there is provided compounds of formula (A) wherein $R_2'$ is F and wherein $R_1$, $R_2$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments D1.

Under another particular aspect of embodiments D1 (embodiments D1c), there is provided compounds of formula (A) wherein $R_2'$ is different from hydrogen or F and wherein $R_1$, $R_2$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments D.

Under specific aspect of embodiments D1a, D1b and D1c (embodiments D1d), there is provided compounds of formula (A) wherein $R_2$ is n-propyl and wherein $R_1$, $R_2'$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments D1a, D1b and D1c.

Under specific aspect of embodiments D1a, D1b and D1c (embodiments D1e), there is provided compounds of formula (A) wherein $R_2$ is i-propyl and wherein $R_1$, $R_2'$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments D1a, D1b and D1c.

Under specific aspect of embodiments D1a, D1b and D1c (embodiments D1f), there is provided compounds of formula (A) wherein $R_2$ is n-butyl and wherein $R_1$, $R_2'$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments D1a, D1b and D1c.

Under specific aspect of embodiments D1a, D1b and D1c (embodiments D1f), there is provided compounds of formula (A) wherein $R_2$ is cyclohexyl and wherein $R_1$, $R_2'$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments D1a, D1b and D1c.

Under specific aspects of embodiments A, A1, A2, A3, A4, B1, B2, B3, B4, B4a, B4b, B5, B6, B7, B8, C1, C2, C3, C4, C5, C6, C7, C8, C9, C10 and C11 (embodiments D2) there is provided compounds of formula (A) wherein $R_2$ and $R_2'$ together with the carbon atom they are attached to form a cycloalkyl ring and wherein $R_1$, $R_3$, $X_1$, $X_2$, $X_3$, $X_4$, $X_5$, $X_6$, $X_7$, $X_8$, $X_9$, $X_{10}$, $Y_1$, $Y_1'$, $Y_2$, $Y_3$, $Y_4$, $Y_5$ and $Y_6$ are, as the case may be, as defined under embodiments A, A1, A2, A3, A4, B1, B2, B3, B4, B4a, B4b, B5, B6, B7, B8, C1, C2, C3, C4, C5, C6, C7, C8, C9, C10 and C11.

The combination of any of the above embodiments gives rise to a new embodiment under this invention.

For example, from the combination of embodiments B3, B4 and B7 there is provided other specific aspects of embodiments A, A1, A2, A3 or A4 (Embodiments E1) which are compounds of formula (A) wherein •-$R_1$ is selected from

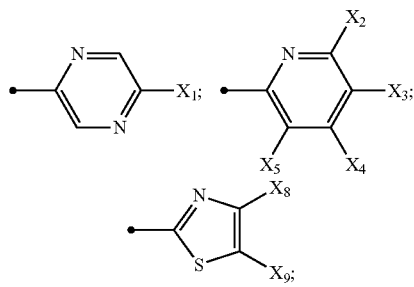

and wherein $R_2$, $R_2'$, $R_3$, $X_1$, $X_2$, $X_3$, $X_4$, $X_5$, $X_8$, $X_9$, $Y_1$, $Y_1'$, $Y_2$, $Y_3$, $Y_4$, $Y_5$ and $Y_6$ are, as the case may be, as defined under embodiment A, A1, A2, A3 or A4

Likewise, from the combination of embodiments B3, B4a and B7, there is provided other specific aspects of embodiments A, A1, A2, A3 or A4 (Embodiments E1a) which are compounds of formula (A) wherein •-$R_1$ is selected from

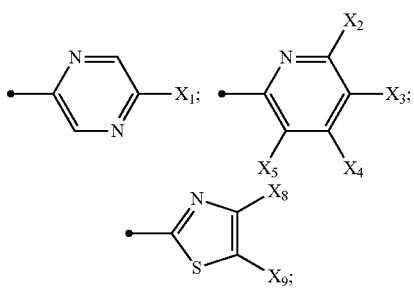

$X_2$ and $X_4$ are hydrogen;
and wherein $R_2$, $R_2'$, $R_3$, $X_1$, $X_3$, $X_5$, $X_8$, $X_9$, $Y_1$, $Y_1'$, $Y_2$, $Y_3$, $Y_4$, $Y_5$ and $Y_6$ are, as the case may be, as defined under embodiment A, A1, A2, A3 or A4

Also, from the combination of embodiments C6, C8, C9 and C11 there is provided other specific aspects of embodiments A, A1, A2, A3, A4, B1, B2, B3, B4, B4a, B4b, B5, B6, B7 or B8 (Embodiments E2) which are compounds of formula (A) wherein •-$R_3$ is selected from

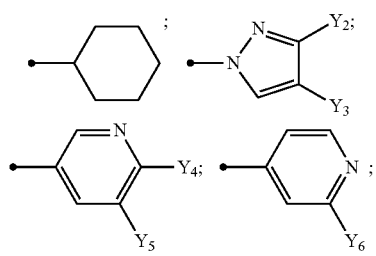

and wherein $R_1$, $R_2$, $R_2'$, $X_1$, $X_2$, $X_3$, $X_4$, $X_5$, $X_6$, $X_7$, $X_8$, $X_9$, $X_{10}$, $Y_2$, $Y_3$, $Y_4$, $Y_5$ and $Y_6$ are, as the case may be, as defined under embodiments A, A1, A2, A3, A4, B1, B2, B3, B4, B4a, B4b, B5, B6, B7 or B8.

Examples 1-151 described below all constitute further individual embodiments of this invention, and any list combining any of the examples is yet another further embodiment of this invention.

For example, in a further embodiment (embodiment F1) there is provided a compound selected form the list of
1-(5-Chloro-pyridin-3-yl)-cyclobutanecarboxylic acid (5-chloro-pyridin-2-yl)-amide;
2-(6-Chloro-5-cyano-pyridin-3-yl)-pentanoic acid (5-chloro-pyrazin-2-yl)-amide;
2-(6-Chloro-5-fluoro-pyridin-3-yl)-pentanoic acid (5-bromo-pyrazin-2-yl)-amide;
2-(6-Bromo-pyridin-2-yl)-pentanoic acid (5-bromo-pyrazin-2-yl)-amide;
2-(2-Bromo-pyridin-4-yl)-pentanoic acid (5-bromo-pyridin-2-yl)-amide;
2-(2-Methoxy-pyridin-4-yl)-pentanoic acid (5-bromo-pyridin-2-yl)-amide;
2-(6-Methoxy-pyridin-3-yl)-pentanoic acid (5-bromo-pyridin-2-yl)-amide;
2-(4-Bromo-3-trifluoromethyl-pyrazol-1-yl)-pentanoic acid (5-bromo-pyrazin-2-yl)-amide;
2-(2-Difluoromethoxy-pyridin-4-yl)-pentanoic acid (5-bromo-pyridin-2-yl)-amide;
2-[6-(1-Methyl-1H-pyrazol-4-yl)-pyridin-3-yl]-pentanoic acid (5-chloro-thiazol-2-yl)-amide;
2-(5-Bromo-pyridin-3-yl)-pentanoic acid (5-bromo-pyrazin-2-yl)-amide;
2-(5-Bromo-pyridin-3-yl)-pentanoic acid (5-bromo-3-methyl-pyridin-2-yl)-amide;
2-(5-Bromo-pyridin-3-yl)-pentanoic acid (5-bromo-6-fluoro-pyridin-2-yl)-amide;
2-(5-Bromo-pyridin-3-yl)-pentanoic acid (5-chloro-pyrazin-2-yl)-amide;
2-(5-Bromo-pyridin-3-yl)-2-fluoro-pentanoic acid (5-chloro-pyridin-2-yl)-amide;
2-(2-Bromo-pyridin-4-yl)-pentanoic acid (5-bromo-pyrazin-2-yl)-amide;
2-(2-Bromo-pyridin-4-yl)-pentanoic acid (5-chloro-pyridin-2-yl)-amide;
2-(5-Bromo-pyridin-3-yl)-pentanoic acid (5-fluoro-pyridin-2-yl)-amide;
2-(2-Methoxy-pyridin-4-yl)-pentanoic acid (5-bromo-thiazol-2-yl)-amide;
2-(2-Methoxy-pyridin-4-yl)-pentanoic acid (5-bromo-pyrazin-2-yl)-amide;
2-(4-Bromo-3-trifluoromethyl-pyrazol-1-yl)-pentanoic acid (5-bromo-pyridin-2-yl)-amide;
2-(4-Bromo-3-cyano-pyrazol-1-yl)-pentanoic acid (5-bromo-pyridin-2-yl)-amide;
2-(5-Bromo-pyridin-3-yl)-hexanoic acid (5-bromo-pyrazin-2-yl)-amide;
2-(4-[4-methoxy-phenyl]-3-trifluoromethyl-pyrazol-1-yl)-pentanoic acid (5-bromo-pyrazin-2-yl)-amide;
2-(4-Bromo-3-methyl-pyrazol-1-yl)-pentanoic acid (5-bromo-pyrazin-2-yl)-amide;
2-(4-Bromo-imidazol-1-yl)-pentanoic acid (5-bromo-pyridin-2-yl)-amide;
2-[3-(4-Methoxy-phenyl)-pyrazol-1-yl]-pentanoic acid (5-bromo-pyrazin-2-yl)-amide;
2-(4-Bromo-3-cyano-pyrazol-1-yl)-pentanoic acid (5-bromo-pyrazin-2-yl)-amide;
2-[5-Fluoro-6-(1-methyl-1H-pyrazol-4-yl)-pyridin-3-yl]-pentanoic acid (5-chloro-pyrazin-2-yl)-amide;
2-[5-Cyano-6-(1-methyl-1H-pyrazol-4-yl)-pyridin-3-yl]-pentanoic acid (5-chloro-pyrazin-2-yl)-amide;
2-(5-Bromo-pyridin-3-yl)-N-(5-bromo-pyrazin-2-yl)3-methyl-butyramide;
N-(5-Bromo-3-fluoro-pyridin-2-yl)-2-(5-bromo-pyridin-3-yl)-3-methyl-butyramide;
N-(5-Bromo-pyrazin-2-yl)-2,2-dicyclohexyl-acetamide;
1-(5-Bromo-pyridin-3-yl)-cyclobutanecarboxylic acid (5-bromo-pyrazin-2-yl)-amide;
1-(5-Chloro-pyridin-3-yl)-cyclobutanecarboxylic acid (5-bromo-pyrazin-2-yl)-amide;
2-(6-Chloro-5-cyano-pyridin-3-yl)-pentanoic acid (5-bromo-pyrazin-2-yl)-amide;
2-(5-Chloro-pyridin-3-yl)-pentanoic acid (5-bromo-pyrazin-2-yl)amide;
2-(5-Chloro-pyridin-3-yl)-pentanoic acid (5-chloro-pyridin-2-yl)-amide;
2-(6-Chloro-5-methyl-pyridin-3-yl)-pentanoic acid (5-chloro-pyrazin-2-yl)-amide;
and 2-(2-Chloro-pyridin-4-yl)-pentanoic acid (5-bromo-pyrazin-2-yl)-amide Likewise, in a in a further embodiment (embodiment F2) there is provided a compound selected form the list of 2-(5-Bromo-pyridin-3-yl)-pentanoic acid (3-tert-butyl-isoxazol-5-yl)-amide and 2-(5-Bromo-pyridin-3-yl)-hexanoic acid (3-tert-butyl-isoxazol-5-yl)-amide General Route to Compounds of the Invention Depending on the exact nature of the compound, compounds of the invention may be obtained under general Schemes 1-5.

Scheme 1
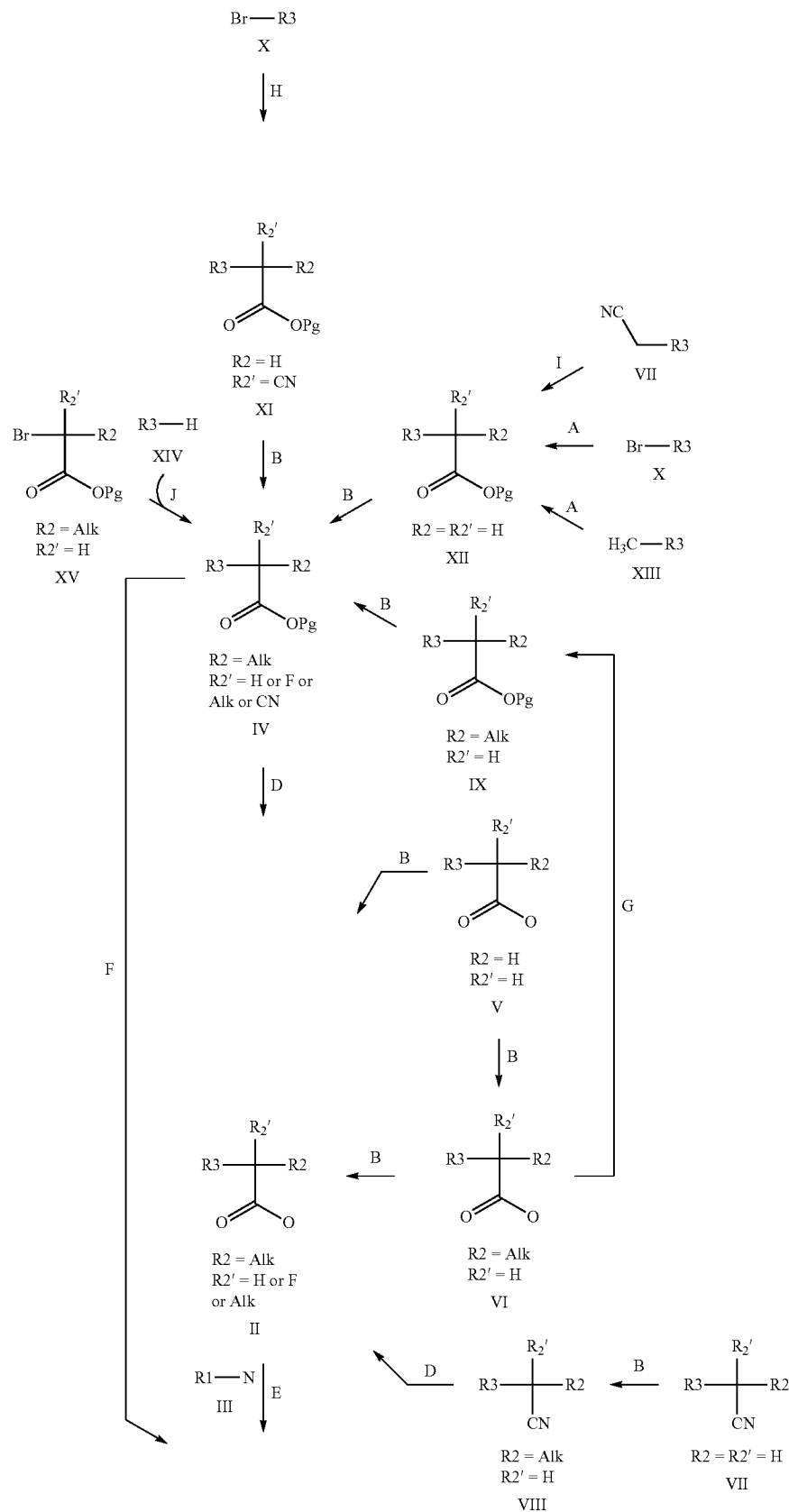

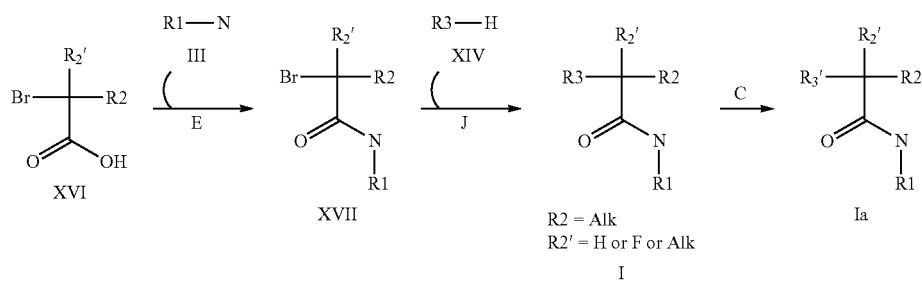

A: carboxylation or Reformatsky-Negishi coupling; B: alkylation; C: miscellaneous modifications on final compounds; D: Hydrolysis; E: Amide coupling between acid and amine; F: Amide coupling between ester and amine; G: esterification; H: alkylation on dicarbonyl compounds; I: alcoholysis; J: N-alkylation Compounds with general structure I can be prepared as shown in Scheme 1. The key step of the synthesis is coupling between acids of general structure II and the appropriate amines of general structure III using coupling agents known in literature. Alternatively, amides of structure I can be achieved directly from esters IV where R2 is alkyl and R2' can be fluorine or hydrogen. When acids of general structure II are not commercially available, they can be prepared according to different approaches.

Alkylation of commercially available heteroarylacetic acid of general structure V, with the appropriate haloalkane, in presence of a strong bases such LiHMDS, n-butyllithium, sodium hydride and other known in literature gives acids of general structure II.

When R2 and R2' are different alkyl groups, acids of general structure II can be prepared in two steps. Heteroaryl acetic acids of general structure V can be alkylated to give intermediates of general structure VI, which undergo to a second alkylation to furnish acids of general structure II.

Alternatively commercially available heteroarylacetonitriles of general structure VII can be alkylated affording intermediates of general structure VIII which can be hydrolyzed to acids II.

Acids of general structure II can be obtained from hydrolysis of esters of general structure IV as reported in Scheme 1 where Pg can be methyl, ethyl or tert-butyl group. In case R2' is a cyano group, hydrolysis and mono-decarboxylation occur simultaneously.

When esters of general structure IV are not commercially available they can be prepared following different synthetic pathways shown in Scheme 1.

Esters of general structure IV where R2 is an alkyl group and R2' is fluorine can be prepared from acids VI, which are converted to corresponding esters IX and finally fluorinated in presence of a strong base and an electrophilic source of fluorine as reported by Tengeiji et al. *Molecules* 2012, 17, 7356-7378.

Esters IV can be prepared from heteroaryl bromides of structure X which are transformed into intermediates XI via palladium catalyzed reaction with malonitrile for example see Xiang Wang et al. *J. Org. Chem.*, 2008, 73, 1643-1645. Derivatives XI can be alkylated to give esters IV where R2' is cyano group.

Ester IV can be prepared directly from alkylation of heteroaryl acetic esters of general structure XII.

When esters XII are not commercially available, they can be synthesised with three different approaches: by alcoholysis of heteroaryl acetonitriles of general structure VII, via Negishi-Reformatsky coupling between heteroaryl bromides of structure X and tert-butyl ester of bromoacetic acid as described by Hartwig, J. F. et al. *JACS*, 2003, 125, 11176-11177 or by carboxylation of methyl group of compounds of general structure XIII in presence of a strong base as LDA (see WO9815278).

Esters of general structure IV can be prepared from N-alkylation of nitrogen bearing heterocycles XIV (pyrazoles, pyrroles, indoles) with ester of α-bromoalkanoic acid of general structure XV.

An alternative approach for the synthesis of compounds of general structure I, depicted in Scheme 1, consists of coupling between appropriate amine of general structure III with α-bromoacid of general structure XVI using a suitable coupling agent to give intermediate of general structure XVII. N-alkylation of nitrogen bearing heterocycles XIV (pyrazoles, pyrroles, and indoles) with intermediates XVII offer compounds of general structure I.

Compounds of general structure I can be further modified into derivatives Ia when R3 contains groups that can be modified in few synthetic steps. For example, when R3 contains methoxy group, it can be demethylated and O-alkylated with different alkyl groups; or in presence of primary amino group, this one can be alkylated to the corresponding tertiary amine or can be acylated with the appropriate carboxylic acid.

Scheme 2

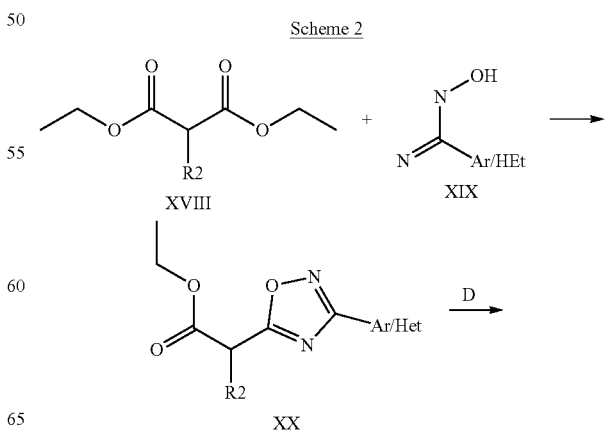

Scheme 3

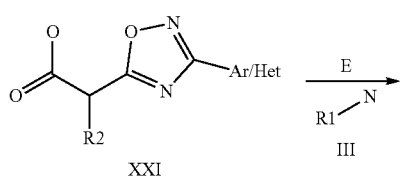

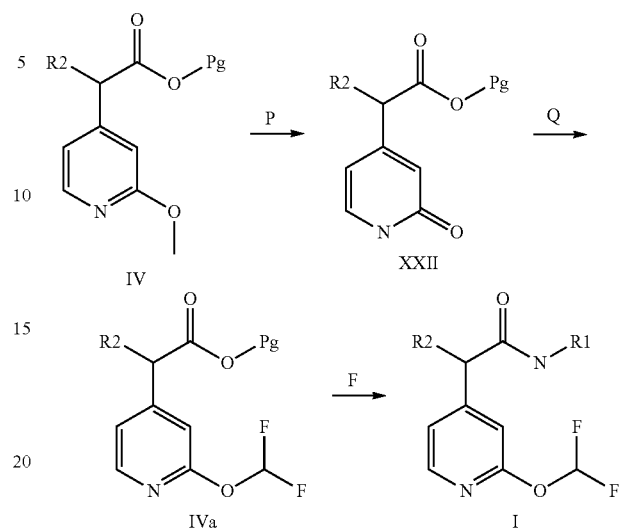

Scheme 2 describes the synthetic approach to prepare compounds of general structure Ib, where R3 is 1,2,4-oxadiazole substituted in position 3 with an aryl or heteroaryl group. Condensation between diethyl alkyl malonate XVIII and amidoxime XIX gives oxadiazole XX, which can be hydrolyzed to corresponding acid XXI and coupled with the appropriate amine of general structure III using a suitable coupling agent to give compounds of general structure Ib.

In Scheme 4 it is depicted the synthesis for a single point modification of intermediates of general structure IV, where methoxy group is replaced by difluoromethoxy moiety. Methoxypyridine esters of general structure IV are converted into the corresponding pyridones XXII followed by difluoromethylation of the oxygen (Makoto et al. *Organic Letters*, 2006, 8, 3805-3808) to give esters of general structure IVa. Direct coupling with the appropriate amines of general structure III affords final compounds I.

Scheme 4

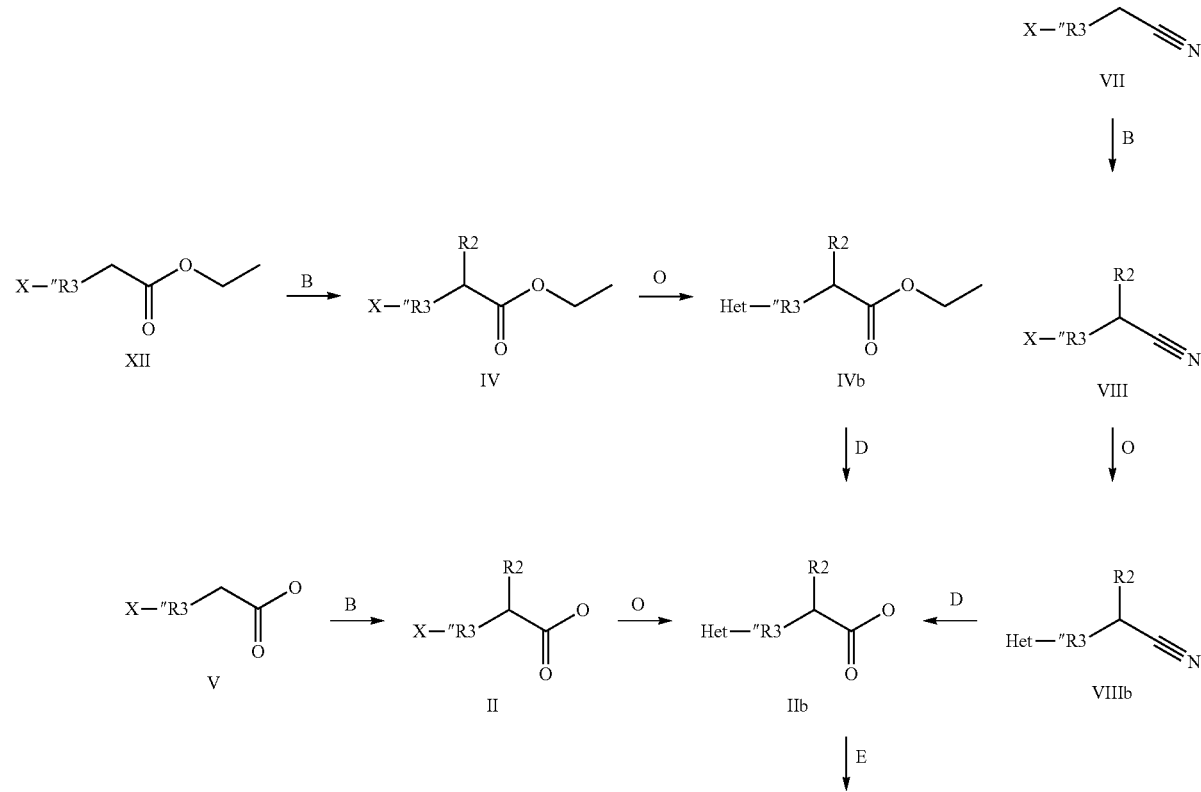

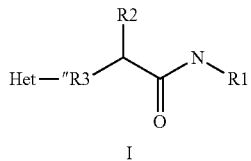

Scheme 4 depicts possible approaches for the synthesis of compounds of general structure I, where R3 is a bis-heteroaryl system. These syntheses can be applied on intermediates of general structure XII, V and VII containing a halogen in the R3 system. Intermediates of general structure II, IV, VIII can be obtained respectively from compounds V, XII and VII as described in Scheme 1. Suzuki coupling on II, IV and VIII gives compounds of general structure IIb, IVb and VIIIb. Intermediate IVb and VIIIb can be hydrolyzed to give compounds of general structure IIb which are converted into compounds I reacting with the appropriate amines of general structure III, using a suitable coupling agent.

Enantiomers or enantiomerically enriched compositions could also be obtained by using optically active starting materials or by enantiomeric resolution strategies.

Enantiomeric resolution strategies of compounds of general structure I are reported in scheme 5. Racemic mixtures of compounds I can be separated by chiral preparative HPLC.

Alternatively, acid of general structure II can be coupled with chiral auxiliaries such oxazolidinones to give diastereoisomers XXIIIa and XXIIIb. The resulting diastereoisomers could be separated and hydrolyzed to give the two acids in pure enantiomeric form that could be coupled with the appropriate amine of general structure III, using a suitable coupling agent to give compounds of general structure I as enantiomers. Alternatively racemic acids of general structure II can be solved before amide coupling with conventional approaches such as crystallization in presence of a chiral amine, enzymatic resolution, chiral preparative HPLC.

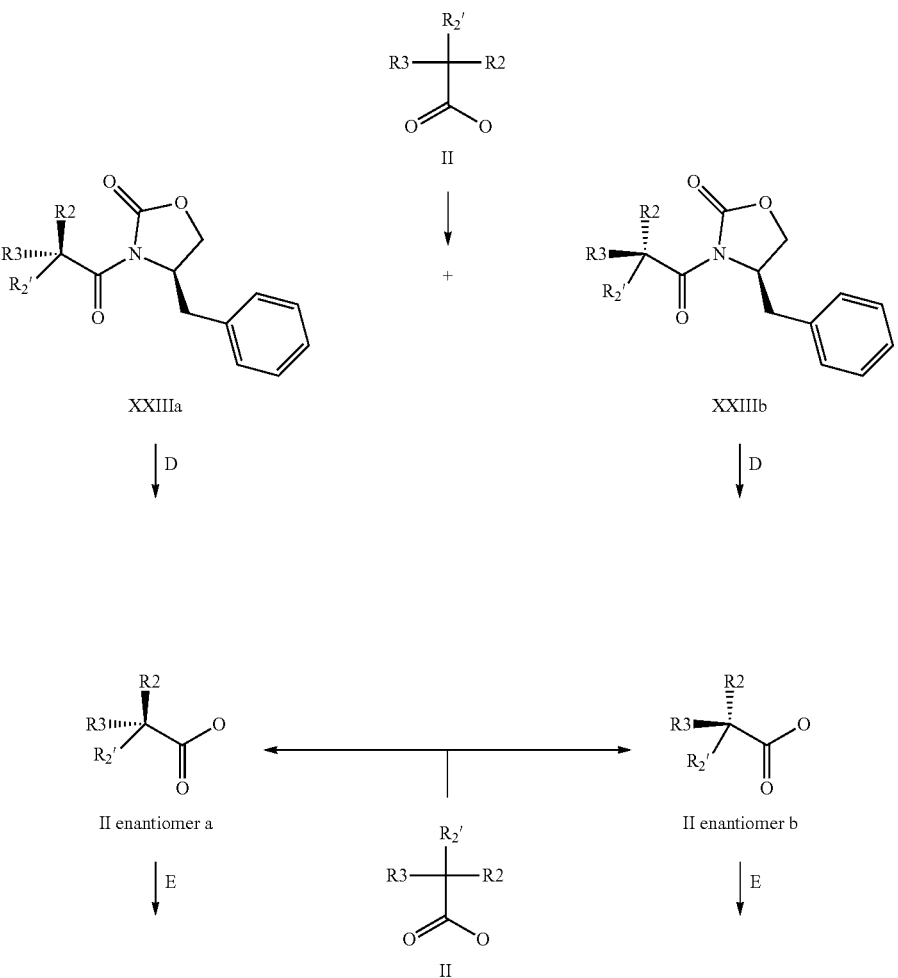

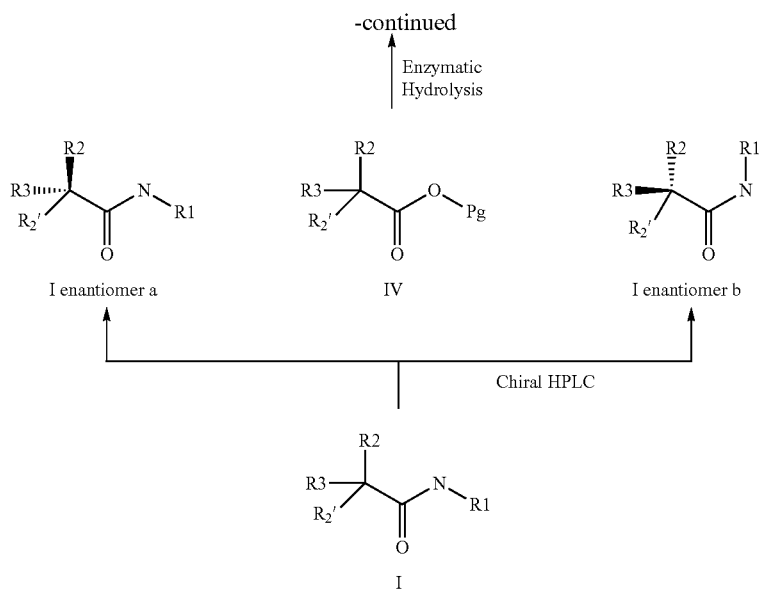

Enantiomers or enantiomerically enriched compositions could also be obtained by using optically active starting materials.

Biological Evaluation

In Vitro Cellular Assay for Activity Against S1P

CHO-S1P3 R1 cells were generated by stably transfecting wt CHO-K1 cells with pcDNA6.2/cLumioDEST-hS1P3 and were maintained under antibiotic selection with 6 μg/ml blasticidin. CHO-S1P1 MG12 cells were also generated by stable transfection of wt CHO-K1 cells and were selected with 1 mg/ml hygromycin.

The compounds were tested on CHO-S1P3 R1 cells for their ability to act as antagonists of the sphyngosine induced intracellular Ca-flux, that was measured by the fluorescent calcium indicator Fluo-4 AM on a Molecular Devices FLIPR3 instrument.

Cells were seeded as 30K cells per well in a 96-well plate (black, clear bottom, TC coated) in 100 μl culture medium. After 24 h incubation cells were loaded with 100 μL HBSS containing 20 mM HEPES buffer, 5 mM probenecid, 4 μM FLUO-4 AM and pluronic acid 0.02% and kept at 37° C., 5% CO2 for 30 minutes. Loading solution was then washed out with HBSS-20 mM Hepes buffer.

Compounds were dispensed to the cells as first addition, at the final concentration of 10 μM for primary screening and in 8 points concentration response (30 μM-0.001 μM) with a final DMSO concentration of 0.3%. Sphingosine was added as second addition at the final concentration equal to the EC80. Calcium responses were read on a fluorescence imaging plate reader (FLIPR3; Molecular Devices) by exciting the cells with an argon ion laser at 488 nm. Emission was recorded by using a band spectrum filter (510-570 nm; emission peak of Fluo-4/Ca2+=516 nm).

The compound activity was also evaluated for the activity on Gαi pathway both against S1P1 receptor and S1P3 receptor.

Changes in intracellular cAMP concentrations were measured with a HTRF® assay (cAMP Dynamic 2 Kit, Cisbio Bioassays, Codolet, France), according to the manufacturer's protocol.

CHO-S1P1 MG12 or CHO-S1P3 R1 ready-to-use frozen cells were thawed, resuspended in DPBS (Lonza, Basel, Switzerland) with 1 mM IBMX and dispensed in 384-well low volume microplates (Greiner Bio-One GmbH, Frickenhausen, Germany) as 10000 cells in 5 μl per well. Cell treatment was performed in assay buffer containing PBS 0.2% BSA. The cells were pre-incubated for 15 min at room temperature with 2.5 μl of a 4-fold concentrated compound solution either at single concentration or in a concentration response titration (0.6% final DMSO concentration). Subsequently, 2.5 μl of a Sphingosine/forskolin solution at 4-fold the respective EC80 concentrations were added to each well except for positive control wells, where only forskolin was added. After 45 min, 5 μl of the HTRF® detection reagents (anti cAMP-Cryptate and cAMP-d2) were added to the cells according to the kit instructions. After 1 hour incubation at room temperature, the time resolved fluorescence was read with an AnalystGT microplate reader (Molecular Devices, Sunnyvale, Calif., USA) with excitation at 337 nm, emission at 665 nm and 620 nm (for acceptor and donor signals, respectively).

In Vitro Phenotypic Assay: S1P Proliferation Assay in Primary Cortical Astrocytes Primary cortical astrocytes were prepared from E17 embryos (Sprague-Dawley) rat neocortex by enzymatic dissociation. The isolated cortices were minced into small pieces with a sterile blade, washed for three times with dissociation medium and incubated with trypsin (0.25%) in waterbath at 37° C. for 10 mins. The pellet was placed in FBS (10%)-containing MEM medium and pipetted for 20 strokes; the cell suspension was centrifuged at 1050 rpm for 10 mins at r.t. and the pellet was resuspended in growth medium (BME, 10% FBS, 2 mM glutamine, 1 mM pyruvate, Penicillin/Streptomycin 1000 U/ml). The cells were seeded in poly-D-lysine (70K-150K kD) pre-coated 75 cm² flasks on at, at 37° C., 5% CO₂ and 95% humidity. The mature cultures were grown until astrocytes had reached confluence (12-15 days). Then, cultures are placed in an orbital shaker and shacked (200 RPM) overnight at 37° C., 5% CO₂ and 95% humidity. Medium was then removed and the cell layer containing mostly astrocytes was removed by trypsinization (0.25%) for 15 mins at 37° C. Furthermore, after blocking trypsin with MEM 10% FBS, medium was eliminated by centrifugation at 1200 RPM. Cells are seeded into black wall, clear bottom 96-well plates (30K cells/well) in 10% FBS/BME (day 1). 24 h later, on day 2, the medium was replaced with serum free BME. On day 3, the cells were treated with the antagonists for 1 hr before S1P addition (S1P final concentration: 1 µM). The final DMSO concentration was 0.1% v/v. On day 5 (48 h S1P stimulation), cells were fixed in 4% paraformaldehyde/4% sucrose, permeabilized in 0.2% Triton-X 100, and blocked in 0.1% BSA. The primary antibody Rb-anti-Ki67 (1:500, Abcam) was incubated for 3 hr at room temperature, followed by the Alexa Fluor 546 conjugated secondary antibody. The plates were acquired with BD Pathway 435 and the nuclear intensity of the Ki67 staining measured with BD Attovision software. The proliferation was expressed as percentage of Ki67-positive nuclei per total nuclei.

Neurodegeneration, Neuroinflammation and Behavioural In Vivo Assays.

The efficacy of the compounds of the invention on neurodegeneration and neuroinflammation can be evaluated with two different methodological approaches aimed to reproduce some pathological features of Alzheimer's disease:
1) the excitotoxic insult (quisqualic acid—QUIS) in the Nucleus Basalis Magnocellularis (NBM), characterized by severe neurodegeneration of cholinergic neurons along with significant neuroinflammation.
2) the β-amyloid peptide 25-35 (Aβ25-35) injection in NBM of rats, inducing a significant glia reaction around Aβ25-35 deposits with modest toxicity on cholinergic neurons.
  Readouts are based on immunochemical analysis and are: count of cholinergic neurons (ChAT-positive), astrocytes (GFAP-positive) and microglia (OX-42 or Iba-1 positive). The analysis is performed by two different approaches, the visual scoring (blind) and the digital platform APERIO®.

QUIS-treated animals can also undergo the Object Recognition Test (ORT, measuring episodic memory) or other behavioural tests to measure the improvement of cognitive functions upon treatment with a compound of the invention.

Animals

Three-month old male Wistar rats (Harlan, Milan, Italy) weighing 230-250 g were used. The rats were housed in macrolon cages with ad lib food and water and maintained on a 12 h light/dark cycle at 23° C. room temperature (RT). All experiments were carried out according to the guidelines of the European Community's Council for Animal Experiments (86/609/EEC). Efforts were made to minimize the number of animals used and their suffering.

Quisqualic Acid and ABeta(25-35) Peptide Injections into the Nucleus Basalis and Drug Treatment The quisqualic acid (Sigma Chemical Co., Milan, Italy; dissolved in phosphate buffer at the concentration of 0.12 M volume 0.5 µl) or 10 ug of ABeta(25-35) peptide (Bachem) dissolved PBS at the concentration of 10 µg/µl and aggregate at 37° for 2 h before injection volume 1 µl) was injected by means of an Hamilton microsyringe into the right NBM under chloral hydrate anaesthesia at the following stereotaxic coordinates: AP=−0.2, L=−2.8 from bregma and H=7 from the dura (Paxinos and Watson, 1982, Casamenti et al., 1998). Controlateral NBM were injected with PBS solution. The study was performed for 7 days after surgery. Rats were orally administered (ip) with a compound of the invention or vehicles with two administration, 24 h and 1 h before surgery and once daily for 7 days after lesioning. Last administration was performed 1 h before sacrifice.

Object Recognition Test

Object recognition was evaluated according to Ennanceur and Delacour (1988) and Scali et al., (1997). Briefly, the rats were placed in a grey polyvinylchloride arena (60×60×40 h cm) illuminated by a 50 W lamp suspended 50 cm above the arena. The objects to be discriminated were prisms, pyramids and cylinders made of plastic. The day before testing, rats were allowed to explore the arena for 2 min. On the day of the test, in the scopolamine protocol, a session of 2 trials separated by an intertrial interval of 240 min was carried out. In the first trial (acquisition trial, T1) two identical objects were presented in two opposite corners of the arena. The rats were left in the arena until criterion of 20 s of total exploration of the objects was reached. Exploration was defined as directing the nose at a distance <2 cm to the object and/or touching it with the nose. During the second trial (retention trial, T2) one of the objects presented in T1 was replaced by a new (differently shaped) object and the rats were left in the arena for 5 min. The times spent exploring the familiar (F) and the new object (N) were recorded separately and the difference between the two exploration times was taken. From one rat to the next, care was taken to avoid object and place preference by randomly changing the role of the objects (familiar or new object) and their position in the two opposite corners of the box during T2. Furthermore, in order to avoid olfactory stimuli the objects to be discriminated were cleaned carefully. In the time delay procedure, T2 was performed 24 h after T1 when a spontaneous decay of memory was presents in control rats. Drug's administrations were performed 30 min before the acquisition trial T1.

Immunohistochemistry

Under deep chloral hydrate anaesthesia, the rats were perfused transcardially with ice-cold paraformaldehyde solution (4% in phosphate-buffer, pH 7.4). The brains were postfixed for 4 h and cryoprotected in 18% sucrose solution for at least 48 h. Brains were cut in a cryostat throughout the injected area into 30 µm-thick coronal sections and placed in anti-freezer solution (phosphate-buffered saline containing 30% ethylene glycol and 30% glycerol) and stored at −20° C. until used for immunohistochemistry, according to the following schedule.

Day 1 ChAT (marker of cholinergic neurons, goat antiserum, Millipore, 1:200), was used as neurodegeneration marker and GFAP (marker of astrocytes, rabbit polyclonal antibody DAKO, 1:1000) and Iba-1 (marker of microglia, rabbit antibody, Wako, 1 1:500) or OX-42 (CD11b/c, marker of activated microglia, mouse antibody, BD Biosciences Pharmingen, 1:400) as neuroinflammation markers of astrocytes and microglia, respectively.

Secondary antibodies: biotinylated IgG (Vector Laboratories, Burlingame, Calif.), diluted 1:1000.

Immunohistochemical Procedure

Slices were processed as free-floating sections, briefly, the primary antibody was added at the appropriate dilution (in Blocking buffer: PBST with 0.5% BSA) and left overnight under mild agitation at room temperature. Then the corresponding biotinylated secondary antibody (in Blocking buffer: PBST with 0.1% BSA) was added to the slices and left 90 min at room temperature, under mild agitation, and then removed and washed with PBS. Bound antibody was visualized by using Vectastain ABC Kit (Vector Laboratories, Burlingame, Calif.) with DAB (Vector Laboratories, Burlingame, Calif.) as chromogen. The sections were mounted, counterstained with Ematossilin (Carlo Erba Reagents, Italy), dehydrated and coverslipped with mounting medium (Leica).

Immunohistochemical Marker Quantification

All immunohistochemical markers were quantified in the NMB area by the Aperio® digital pathology platform; briefly, 4-6 slides per animal were digitalized by using the scanner Scanscope CS (Aperio®), then the right and left NMB areas were manually identified for each slide creating a Region Of Interest (ROI) where specific macros of analysis were applied to quantify the signal. Each right striatum (injected with AAV9-Ex1-AcGFP-Q138) was compared with its contralateral (left) one (injected with AAV9-Ex1-AcGFP-Q17). Data from each slide were averaged on a per animal basis and the resulting values were used for statistical analysis.

ChAT was quantified as number of cells per area, as a single cell population. GFAP and Iba-1, were evaluated as positive pixel counts per area in the Region of Interest (ROI).

Formulation and Administration

Compounds under formula (A) are formulated preferably in admixture with a pharmaceutically acceptable carrier, excipient or the like. In general, it is preferable to administer the pharmaceutical composition in orally-administrable form, but certain formulations may be administered via a parenteral, intravenous, intramuscular, transdermal, buccal, subcutaneous, suppository, nasal or other route. One of ordinary skill in the art may modify the formulations within the teachings of the specification to provide numerous formulations for a particular route of administration without rendering the compositions of the present invention unstable or compromising their therapeutic activity.

In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including ester and ether derivatives, as well as various salt forms of the present compounds, are preferred.

One of ordinary skill in the art will recognize how to readily modify the present compounds to pro-drug forms to facilitate delivery of active compounds to a targeted site within the host organism or patient.

The routineer also will take advantage of favourable pharmacokinetic parameters of the pro-drug forms, where applicable, in delivering the present compounds to a targeted site within the host organism or patient to maximize the intended effect of the compound.

Actual methods of preparing such dosage forms are known, or will be apparent, to those skilled in this art; for example, see Remington's Pharmaceutical Sciences, Mack Publishing Company, Easton, Pa., 15th Edition, 1975.

The composition or formulation to be administered will, in any event, contain a quantity of the active compound in an amount effective to alleviate the symptoms of the subject being treated.

While human dosage levels have yet to be optimized for the compounds of the invention, generally, a daily dose is from about 0.05 mg/kg to about 100 mg/kg of body weight.

The amount of active compound administered will, of course, be dependent on the subject and disease state being treated, the severity of the affliction, the manner and schedule of administration and the judgment of the prescribing physician.

For purposes of the present invention, a prophylactically or preventive effective amount of the compositions according to the present invention (i.e., an amount which substantially reduces the risk that a patient will either succumb to a disease state or condition or that the disease state or condition will worsen) falls within the same concentration range as set forth above for therapeutically effective amounts and is usually the same as a therapeutically effective amount.

In some embodiments of the present invention, one or more compounds of formula (A) are administered in combination with one or more other pharmaceutically active agents. The phrase "in combination", as used herein, refers to agents that are simultaneously administered to a subject. It will be appreciated that two or more agents are considered to be administered "in combination" whenever a subject is simultaneously exposed to both (or more) of the agents.

Each of the two or more agents may be administered according to a different schedule; it is not required that individual doses of different agents be administered at the same time, or in the same composition. Rather, so long as both (or more) agents remain in the subject's body, they are considered to be administered "in combination".

EXAMPLES

Experimental Section

All reagents and solvents were obtained commercially. Air and moisture sensitive liquid solutions were transferred via syringe. The course of reactions was followed by thin-layer chromatography (TLC) and/or liquid chromatography-mass spectrometry (HPLC-MS or UPLC-Ms). TLC analyses were performed on silica (Merck 60 F254) and spots revealed by UV visualisation at 254 nm and $KMnO^4$ or ninhydrin stain.

Purifications by column chromatography were performed using silica cartridges Isolute flash Si or silica (Merck 60) or with flash chromatography purification instruments (Biotage). Compounds purities were above 90%.

All nuclear magnetic resonance spectra were recorded using a Bruker Avance AV 400 System (400.13 MHz for $^1H$) equipped with BBI a probe.

Abbreviation

THF: Tetrahydrofuran
$NH_4Cl$: Ammonium chloride
AcOEt: Ethyl Acetate
$Na_2SO_4$: Sodium sulphate
HCl: Hydrochloric acid
DMF: N,N-dimethylformamide
NaH: Sodium Hydride
$H_2O$: Water
DCM: dichloromethane
NaOH: sodium hydroxide
$K_2CO_3$: potassium carbonate
$NaHCO_3$: sodium hydrogencarbonate
MeOH: methanol
EDC: 1-(3-dimethylaminopropyl)-3-ethylcarbodiimide hydrochloride
DCE: 1, 2-dichloroethane
DIPEA: N,N-diisopropyl-N-ethylamine
NaCl: sodium chloride
$K_3PO_4$: Tripotassium phosphate Pd$_2$(dba)$_3$: Tris(dibenzylideneacetone)dipalladium (0)
Qphos: 1,2,3,4,5-Pentaphenyl-1'-(di-tert-butylphosphino)ferrocene
T$_3$P: Propylphosphonic Anhydride
EtOH: ethanol
Cs$_2$CO$_3$: Cesium carbonate
LiHMDS: lithium bis(trimethylsilyl)amide
H$_2$SO$_4$: Sulfuric acid
LDA: Lithium diisopropylamide
cHex: cyclohexane
NH$_4$OH: ammonium hydroxide
H$_2$: hydrogen
Pd/C: palladium on activated carbon
CDI: 1,1'-Carbonyldiimidazole
CH$_3$CN: Acetonitrile
Analytical Methods
Method c:
Analytical HPLC-MS were run using a Waters 2795 separation module equipped with a Waters Micromass ZQ (ES ionisation) and Waters PDA 2996, using a X-Bridge C18 3.5 μm 2.10×50 mm column. Gradient: 0.1% ammonia/water and acetonitrile with gradient 85/15 to 5/95 flow 0.8 ml/min over 5/10 minutes. Temperature: 40° C. UV Detection at 215 and 254 nm. ESI+ detection in the 80-1000 m/z range
Method d:
Analytical UPLC-MS were run using a Acquity Waters UPLC with equipped with a Waters SQD (ES ionization) and Waters Acquity PDA detector, using a column BEH C18 1.7 μm, 2.1×5.00. Temperature: 40° C. UV Detection at 215 and 254 nm. ESI+ detection in the 80-1000 m/z range Gradient 0.1% ammonium bicarbonate/water and acetonitrile with a gradient 95/5 to 15/85 flow: 0.8 ml/min over 4 min.
Method e:
Analytical UPLC-MS were run using a Acquity Waters UPLC with equipped with a Waters SQD (ES ionization) and Waters Acquity PDA detector, using a column BEH C18 1.7 μm, 2.1×5.00. Temperature: 40° C. UV Detection at 215 and 254 nm. ESI+ detection in the 80-1000 m/z range. Gradient 0.04% formic acid/95% water/5% acetonitrile and CH3CN with a gradient 95/5 to 0/100 flow: 0.8 ml/min over 4 minutes.
Method f:
Analytical UPLC-MS were run using a Acquity Waters UPLC with equipped with a Waters SQD (ES ionization) and Waters Acquity PDA detector, using a column BEH C18 1.7 μm, 2.1×5.00. Temperature: 40° C. UV Detection at 215 and 254 nm. ESI+ detection in the 80-1000 m/z range. Gradient 0.1% formic acid/water and 0.1% formic acid/CH3CN with a gradient 95/5 to 5/95 flow: 0.6 ml/min over 3 minutes.
Preparative HPLC Method
Method a:
Preparative HPLC was run using a Waters 2767 system with a binary gradient Module Waters 2525 pump and coupled to a Waters Micromass ZQ 25 (ES) or Waters 2487 DAD, using a X-Bridge C18 5 μm 19×150. Gradient 0.1% ammonia/water and methanol flow: 17 ml/min.
Method b: Preparative HPLC was run using a Waters 2767 system with a binary gradient Module Waters 2525 pump and coupled to a Waters MS3100 SQ or Waters 2487 DAD, using a X-Bridge C18 5 μm 19×150. Gradient 0.1% formic acid/water and 0.1% formic acid/methanol flow: 17 ml/min.

General Synthetic Procedures
General Procedure A1 for Carboxylation
To a solution of N,N-diisopropylamine (2.1 eq) in anhydrous THF (0.4 mL*mmol) cooled to −78° C., a solution of n-butyllithium (2.5 M in hexane, 2 eq) was added dropwise under an inert atmosphere. The mixture was stirred at −78° C. for one hour and then the desired methylpyridine (1 eq) was added. The reaction mixture was stirred at −78° C. for one hour and a solution of diethyl carbonate (1.2 eq) in THF (0.3 mL*mmol) was added. The reaction mixture was allowed to warm up to room temperature and left stirring overnight. The mixture was quenched with $_{H2O}$ and extracted twice with AcOEt. The organic layer was collected, washed with saturated sodium chloride solution, dried over Na$_2$SO$_4$ and concentrated under reduced pressure. The crude product was purified by silica gel chromatography.
General Procedure A2 for Reformatsky-Negishi Coupling
To prepare the Reformatsky reagent Zinc dust (1.2 eq) was suspended in anhydrous THF under N$_2$ and Trimethylsilyl chloride 0.1 eq was added dropwise and the resulting suspension was refluxed for 1 h. Then bromoacetic acid tert-butyl ester (1.2 eq) was added dropwise and the resulting reaction mixture was refluxed for 2 h. The resulting Reformatsky reagent was added to a degassed suspension of Bromo-aryl or heteroaryl compound (1 eq), Q-phos (0.05 eq) and Palladium source (0.05 eq.) in anhydrous THF. The resulting reaction mixture was heated at 75° C. overnight. The reaction was worked up adding a saturated solution of NH$_4$Cl and AcOEt. The aqueous layer was extracted again with AcOEt and the resulting organic layers were combined, dried over Na$_2$SO$_4$ and concentrated in vacuo. The crude product was purified by silica gel chromatography.
General Procedure B1 for the Alkylation of Acid:
To a solution of heteroaryl-acetic acid (1 eq) in anhydrous THF cooled to −78° C., a solution of LiHMDS (1M 2.2 eq) in THF was added. The resulting mixture was stirred at −78° C. for 1 hour. Then 1-iodoproprane (1.1 eq) was added portionwise and the reaction mixture was allowed to warm up to room temperature and left stirring overnight. The reaction mixture was quenched with $_{H2O}$ and extracted with AcOEt. The aqueous layer was separated; the solution was acidified to pH3 with 6N HCl and extracted with AcOEt three times. The organic phases were collected, dried over Na$_2$SO$_4$ and concentrated under reduced pressure. The crude product was purified by silica gel chromatography.
General Procedure B2 for Alkylation-Cyclization
Ethyl 2-(5-bromopyridin-3-yl)acetate (1 eq) was dissolved in DMF (5 mL*mmol); 18-crown-6 ether (0.05 eq) and NaH 60% dispersion in mineral oil (2.5 eq) were added and the mixture was stirred at room temperature for 30 minutes; dibromo alkane (1.1 eq) was added dropwise and reaction was stirred at room temperature for 5 h. NaOH 15% solution in H$_2$O (1.5 mL*mmol) was added and the mixture was stirred for 16 h at room temperature. H$_2$O was added and pH was adjusted to 3 with HCl 6N. Aqueous solution was extracted with DCM; organic phases were collected, dried over Na$_2$SO$_4$, filtered and evaporated. The crude product was purified by silica gel chromatography
General Procedure B3 for Alkylation
A solution of acid (1 eq) in dry THF (1.4 mL*mmol) was added dropwise to a solution of n-Butyllithium 1.6 M in n-hexane (2.2 eq) in THF (0.3 mL*mmol) at −78° C. The reaction was stirred at −78° C. in inert atmosphere for 2 h; then a solution of haloalkane (1.1 eq) in THF (0.6 mL*mmol) was added dropwise. Solution was allowed to warm up to room temperature and stirred for 16 h. H$_2$O was carefully added and mixture was diluted with AcOEt. Aqueous phase was collected, acidified to pH=1 with 6N HCl and extracted with AcOEt; organic layer was collected, dried over $Na_2SO_4$, filtered and evaporated under vacuum General Procedure B4 for Fluoro Insertion A solution of LiHMDS 1M in THF (1.1 eq) was diluted with THF (4.0 mL*mmol) and cooled to −78° C.; a solution of ethyl ester (1.0 eq) in the same solvent (2.0 mL*mmol) was added drop-wise. The mixture was stirred at 0° C. for 30 minutes and then cooled to −78° C. again. A solution in THF (4.0 mL*mmol) of N-fluorobenzene sulfonimide (1.3 eq) was added dropwise; the mixture was then warmed to room temperature and stirred for 12 hours. The reaction was quenched with $NH_4Cl$ saturated aqueous solution, extracted with AcOEt and washed with $H_2O$. The organic layer was collected and the solvent was removed under reduce pressure. The crude product was purified by silica gel chromatography.

General Procedure B5 for Alkylation of Acid and Ester

Heteroaryl acetic acid ethyl ester (1 eq) was dissolved in DMF (2 mL*mmol), cesium carbonate (1.2 eq) and iodoalkane (1.1 eq) were added and the mixture was stirred at room temperature overnight. $H_2O$ was added and crude extracted three times with AcOEt. Organic phases were combined, dried over $Na_2SO_4$ and concentrated in vacuo. The crude product was purified by silica gel chromatography.

General Procedure C1 for Phenol Alkylation

To a suspension of the desired phenol (1 eq) and $K_2CO_3$ (2 eq) in DMF, the desired alkyl bromide (4 eq) was added and the mixture was heated at 70° C. for 18 hours. $_{H2O}$ was added and the mixture was extracted with AcOEt. The organic phase was collected and concentrated under reduced pressure. The crude product was purified by silica gel chromatography.

General Procedure D1 for Acid Hydrolysis

A solution of the desired ester in concentrated HCl (0.37 mmol/mL) was stirred at 100° C. for two hours. The mixture was concentrated under reduce pressure and the crude product was used in the next step without further purification.

General Procedure D2 for Acid Hydrolysis

To a solution of tert-butyl ester (1 eq) in DCM (10 mL*mmol), trifluoroacetic acid (1 mL*mmol) was added and the mixture was stirred at room temperature for three days. The mixture was concentrated under reduced pressure, then was diluted with DCM and extracted with $NaHCO_3$ saturated solution. The aqueous layer was separated, acidified to pH3 with HCl 1N and extracted with DCM. The organic phase was separated, dried over $Na_2SO_4$ and concentrated under reduced pressure, affording the title compound.

General Procedure D3 for Basic Hydrolysis

To a solution of ester (1 eq) in MeOH (7.5 mL*mmol), a solution of 2N NaOH (7.5 mL*mmol) was added and the mixture was stirred at room temperature for 3 hours. The solvent was removed under reduced pressure, the residue was suspended in $_{H2O}$ and the mixture was acidified with 1N HCl to pH3. The aqueous phase was extracted with DCM and the organic layer was collected and dried over $Na_2SO_4$. The title compound was obtained without further purification.

General Procedure E1 for the Amide Coupling with Thionyl Chloride:

To a solution of carboxylic acid (1 eq) in 1,2-dichloroethane (4.3 mL*mmol) thionyl chloride (1.2 eq) and catalytic amount of DMF were added and the mixture was stirred at 60° C. for 4 hours. Then the mixture was allowed to cool down to room temperature and the desired amine (1.2 eq) and DIPEA (3 eq) were added. The mixture was stirred at room temperature overnight then washed with saturated $NaHCO_3$ solution, the organic layer collected and the solvent was removed under reduce pressure. The crude product was purified by silica gel chromatography.

General Procedure E2 for Amide Coupling with EDC and 1-Hydroxybenzotriazole Hydrate To a solution of acid (1 eq) in DMF (3 mL*mmol), amine (1.1 eq), 1-hydroxybenzotriazole hydrate (0.36 eq) and EDC (1.5 eq) were added. The mixture was stirred at room temperature for one hour. $NaHCO_3$ saturated solution was added and the mixture was extracted with DCM. The combined organic extracts were washed with saturated NaCl solution, dried over $Na_2SO_4$ and evaporated. The crude product was purified by silica gel chromatography.

General Procedure E3 for the Amide Coupling with N-Bromosuccinimide Triphenylphosphine:

To a solution of triphenylphosphine (1.6 eq) in DCM (1 ml*mmol of carboxylic acid) cooled at 0° C., N-bromosuccinimide (1.6 eq) was added and the mixture left at 0° C. for 30 minutes. The desire carboxylic acid (1 eq) was added and the reaction was allowed to warm up to room temperature and lest stirring for 45 minutes. Amine (2.5 eq) was added and the mixture was left stirring for 18 hours at room temperature. The mixture was washed with 1N HCl solution and $NaHCO_3$ saturated solution. The organic phase was collected and the solvent was removed under reduced pressure. The crude product was purified by silica gel chromatography.

General Procedure E4 for the Amide Coupling with T3P

To a solution of carboxylic acid (1 eq) and amine (1 eq) in AcOEt, DIPEA (2 eq) was added and solution cooled to 0° C. T3P 50% solution in AcOEt (1.5 eq) was added and reaction was stirred for 12 h at room temperature. $NaHCO_3$ saturated solution was added, organic layer was separated, dried over $Na_2SO_4$, filtered and evaporated. The crude product was purified by silica gel chromatography.

General Procedure F1 for Amide Coupling of Ester

To a solution of acid (1 eq 0.12 g, 0.47 mmol) in DMF (3 mL*mmol), amine (1.1 eq), 1-hydroxybenzotriazole hydrate (0.36 eq) and EDC (1.5 eq) were added. The mixture was stirred at room temperature for one hour. $NaHCO_3$ saturated solution was added and the mixture was extracted with DCM. The combined organic extracts were washed with saturated NaCl solution, dried over $Na_2SO_4$ and evaporated. The crude product was purified by silica gel chromatography.

General Procedure I for Nitrile Alcoholysis

To a solution of EtOH (2 mL*mmol of nitrile) $H_2SO_4$ concentrated (0.76 mL*mmol of nitrile) was added dropwise and the desired nitrile (1 eq) was added portion wise. The solution was stirred at 100° C. for three hours. The mixture was added dropwise to a solution of $NaHCO_3$ (3.00 g*mmol of nitrile) in $H_2O$ (7.5 mL*mmol of nitrile) and it was extracted twice with DCM. The organic layer were collected, dried and evaporated, affording the desired compound.

General Procedure C1 for Phenol Alkylation

To a suspension of the desired phenol (1 eq) and $K_2CO_3$ (2 eq) in DMF, the desired alkyl bromide (4 eq) was added and the mixture was heated at 70° C. for 18 hours. $H_2O$ was added and the mixture was extracted with AcOEt. The organic phase was collected and concentrated under reduced pressure. The crude product was purified by silica gel chromatography.

General Procedure J1 for Alkylation

To a solution of N-heterocycle (1 eq) in DMF (2 ml*mmol), NaH (60% in mineral oil, 1.2 eq) was added and the mixture was stirred at room temperature for 30 minutes. 2-Bromo-alkanoic acid ethyl ester (1.1 eq) was added and the reaction was left stirring at room temperature overnight. Saturated NaCl solution was added and the mixture was extracted with DCM. The organic phase was collected, dried over $Na_2SO_4$ and concentrated under reduced pressure. The crude product was purified by silica gel chromatography.

General Procedure J2 for Alkylation

A suspension of N-heterocycle (1 eq) and $K_2CO_3$ (2 eq) in acetone (4 mL*mmol) was heated at 55° C. for 10 minutes and then was allowed to cool down to room temperature. 2-Bromo-alkanoic acid ethyl ester (1.1 eq) was the added and the mixture was heated at 55° C. for 18 hours. The solvent was removed under reduced pressure and the crude product was suspended in DCM and washed with H2O. The organic phase was collected, dried over $Na_2SO_4$ and concentrated under reduced pressure.

General Procedure O for Suzuki Coupling

Ester/Acid (1 eq) was dissolved in degassed dioxane (4 mL*mmol), boronic acid or ester (1 eq), $K_3PO_4$ (1.7 eq), phosphine (0.02 eq), $Pd_2(dba)_3$ (0.01 eq) were added then degassed $H_2O$ (0.5 mL*mmol) was added and reaction mixture was heated at 100° C. in a pressure tube for 16 h. AcOEt and NaCl saturated solution were added. Organic phase was collected and evaporated. The crude product was purified by silica gel chromatography.

Example 1: 2-(5-Bromo-pyridin-3-yl)-pentanoic Acid (5-bromo-pyridin-2-yl)-amide

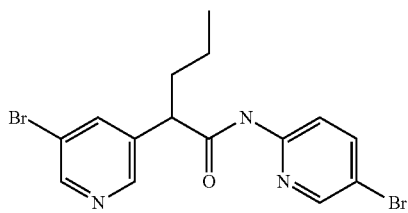 [SMILES: CCCC(C(=O)Nc1ccc(Br)cn1)c1cncc(Br)c1]

2-(5-Bromo-pyridin-3-yl)-pentanoic Acid

To a solution of (5-Bromo-pyridin-3-yl)-acetic acid (2.00 g, 9.2 mmol) in anhydrous THF (20 mL) cooled to −78° C., a solution of LiHMDS (1M, 20 mmol) in THF was added. The resulting mixture was stirred at −78° C. for 1 hour. Then 1-iodo-propane (1.70 g, 10.2 mmol) was added portionwise and the reaction mixture was allowed to warm up to room temperature and left stirring overnight. The reaction mixture was quenched with $_{H2O}$ and extracted with AcOEt. The aqueous layer was separated; the solution was acidified to pH3 with HCl 6N and extracted with AcOEt three times. The organic phases were collected, dried over $Na_2SO_4$ and concentrated under reduced pressure. The crude product was purified by silica gel chromatography (cHex/AcOEt 1/1) to afford the title compound (1.2 g, 50%).

$C_{10}H_{12}BrNO_2$ Mass (calculated) [258.12]; (found) $[M+H]^+$=269.

2-(5-Bromo-pyridin-3-yl)-pentanoic Acid (5-bromo-pyridin-2-yl)-amide

To a solution of 2-(5-bromo-pyridin-3-yl)-pentanoic acid (0.12 g, 0.47 mmol) in DCE (2 mL) thionyl chloride (0.08 g, 0.56 mmol) and catalytic amount of DMF were added and the mixture was stirred at 60° C. for four hours. Then the mixture was allowed to cool down to room temperature and 5-bromo-pyridin-2-ylamine (0.10 g, 0.59 mmol) and DIPEA (0.18 g, 1.395 mmol) were added. The mixture was stirred at room temperature overnight then washed with sodium bicarbonate saturated solution, the organic layer collected and the solvent was removed under reduce pressure. The crude product was purified by silica gel chromatography (cHex/AcOEt 1/1), to afford the title compound (0.05 g, 25%).

$^1$H NMR (400 MHz, Chloroform-d3) δ 8.62 (d, J=2.1 Hz, 1H), 8.49 (d, J=2.1 Hz, 1H), 8.31 (d, J=2.4 Hz, 1H), 8.14 (d, J=8.8 Hz, 1H), 7.98-7.91 (m, 2H), 7.81 (dd, J=8.8, 2.4 Hz, 1H), 3.47 (t, J=7.5 Hz, 1H), 2.23-2.12 (m, 1H), 1.87-1.75 (m, 1H), 1.44-1.24 (m, 2H), 0.96 (t, J=7.3 Hz, 3H).

$C_{15}H_{15}Br_2N_3O$, Calculated [413.11], found $[M+H^+]$ 414, RT=1.74 (method f).

Example 2: 2-(5-Bromo-pyridin-3-yl)-hexanoic Acid (5-bromo-3-fluoro-pyridin-2-yl)-amide

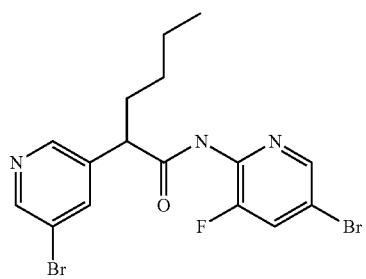 [SMILES: CCCCC(C(=O)Nc1ncc(Br)cc1F)c1cncc(Br)c1]

2-(5-Bromo-pyridin-3-yl)-hexanoic Acid

The title compound was obtained following general procedure for alkylation B1 and starting from (5-bromo-pyridin-3-yl)-acetic acid and 1-Iodo-butane (1.82 g, 51%).

$C_{11}H_{14}BrNO_2$ Mass (calculated) [272]; (found) $[M+H]^+$=274.

5-Bromo-3-fluoro-pyridin-2-ylamine

To a solution of 3-fluoro-pyridin-2-ylamine (0.30 g, 2.68 mmol) in acetonitrile (15 mL), in inert atmosphere, N-bromosuccinimide (0.48 g, 2.68 mmol) was added. The mixture was stirred for 4 hours. Solvent was removed under reduced pressure and the crude product was purified by silica gel chromatography (cHex/AcOEt 66/34) to give the title compound (0.46 g, 89%).

$C_5H_4BrFN_2$ Mass (calculated) [191]; (found) $[M+H]^+$=193.

2-(5-Bromo-pyridin-3-yl)-hexanoic Acid (5-bromo-3-fluoro-pyridin-2-yl)-amide

The title compound was obtained following general procedure E1 for amide coupling and starting from 2-(5-bromo-pyridin-3-yl)-hexanoic acid and 5-bromo-3-fluoro-pyridin-2-ylamine, (0.10 g, 34%).

$^1$H NMR (400 MHz, Chloroform-d3) δ 8.60 (d, J=2.2 Hz, 1H), 8.49 (d, J=2.2 Hz, 1H), 8.27 (d, J=2.0 Hz, 1H), 7.97 (t, J=2.2 Hz, 1H), 7.78 (s, 1H), 7.64 (dd, J=9.0, 2.0 Hz, 1H), 3.90 (bs, 1H), 2.28-2.14 (m, 1H), 1.88-1.74 (m, 1H), 1.46-1.18 (m, 4H), 0.89 (t, J=7.1 Hz, 3H). $C_{16}H_{16}Br_2FN_3O$, Calculated [445.12], found [M+H⁺], 2Br pattern 446, RT=1.64 (method f).

Example 3: N-(5-Bromo-6-fluoro-pyridin-2-yl)-2-(5-bromo-pyridin-3-yl)-3-methyl-butyramide

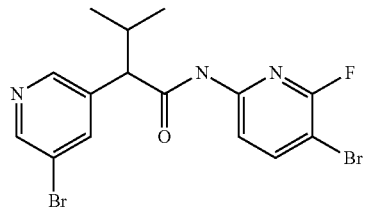 [SMILES: CC(C)C(C(=O)Nc1ccc(Br)c(F)n1)c1cncc(Br)c1]

2-(5-Bromo-pyridin-3-yl)-3-methyl-butyric Acid

The title compound was prepared following general procedure B1 for the alkylation of acid. (1.80 g, 61%).
Mass (calculated) $C_{10}H_{12}BrNO_2$ [258]; found [M+1]=258-260 bromine pattern.

N-(5-Bromo-6-fluoro-pyridin-2-yl)-2-(5-bromo-pyridin-3-yl)-3-methyl-butyramide

Amide coupling was performed with thionyl chloride following the procedure E4. The crude product was purified by silica gel chromatography eluting (CHex/AcOEt 0-40%) to give title compound (0.09 g, 36%).
¹H NMR (400 MHz, Chloroform-d3) δ 8.62 (d, J=2.2 Hz, 1H), 8.46 (d, J=1.9 Hz, 1H), 8.05-7.97 (m, 2H), 7.93 (t, J=8.5 Hz, 1H), 7.84 (bs, 1H), 2.98 (d, J=10.2 Hz, 1H), 2.52-2.38 (m, 1H), 1.12 (d, J=6.5 Hz, 3H), 0.79 (d, J=6.6 Hz, 3H). C15H14N3OFBr2, Calculated [431.10], found [M+H⁺], 432, RT=1.79 (method f).

Example 4: 1-(5-Bromo-pyridin-3-yl)-cyclobutanecarboxylic Acid (5-bromo-pyridin-2-yl)-amide

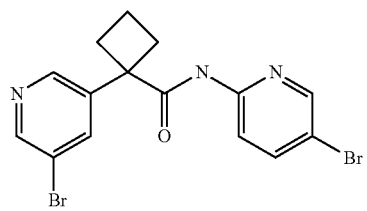 [SMILES: O=C(Nc1ccc(Br)cn1)C1(c2cncc(Br)c2)CCC1]

1-(5-Bromo-pyridin-3-yl)-cyclobutane carboxylic Acid

Ethyl 2-(5-bromopyridin-3-yl)acetate (1.0 g, 4.09 mmol, 1 eq) was dissolved in DMF (20 mL); 18-crown-6 ether (0.054 g, 0.205 mmol, 0.05 eq) and NaH 60% dispersion in mineral oil (0.41 g, 10.2 mmol, 2.5 eq) were added and the mixture was stirred at room temperature for 30 minutes; 1,3-dibromopropane (0.46 mL, 4.50 mmol, 1.1 eq) was added dropwise and reaction was stirred at room temperature for 5 h. NaOH 15% solution in H₂O (10 mL) were added and the mixture was stirred for 16 h at room temperature. H₂O was added and pH was adjusted to pH=3 with HCl 6N. Aqueous solution was extracted with DCM (2×20 mL), organic phases were collected, dried over Na₂SO₄, filtered and evaporated. The crude product was purified by silica gel chromatography (cHex/AcOEt 5%-60%) to give the title compound (0.38 g, 37% over two steps).
$C_{10}H_{10}BrNO_2$ Mass (calculated) [256]; found [M+1]=256-258 bromine pattern.

1-(5-Bromo-pyridin-3-yl)-cyclobutanecarboxylic Acid (5-bromo-pyridin-2-yl)-amide Amide coupling on 1-(5-bromo-pyridin-3-yl)-cyclobutane carboxylic acid and 5-bromo-pyridin-2-ylamine was performed using general procedure E2 to give the title compound (0.015 g, 11%).
¹H NMR (400 MHz, Chloroform-d3) δ 8.66-8.56 (m, 2H), 8.29-8.24 (m, 1H), 8.19-8.12 (m, 1H), 7.88-7.76 (m, 2H), 7.58 (s, 1H), 3.01-2.89 (m, 2H), 2.63-2.51 (m, 2H), 2.24-1.93 (m, 2H).
$C_{15}H_{13}N_3OBr_2$, Calculated [411.09], found [M+H⁺], 2 Br pattern 412, RT=1.61 (method f).

Example 5: 1-(5-Bromo-pyridin-3-yl)-cyclopentanecarboxylic Acid (5-bromo-pyrazin-2-yl)-amide

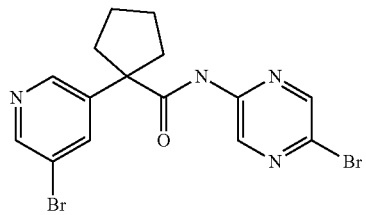 [SMILES: O=C(Nc1cnc(Br)cn1)C1(c2cncc(Br)c2)CCCC1]

1-(5-Bromo-pyridin-3-yl)-cyclopentanecarboxylic Acid

Starting from 1-(5-bromo-pyridin-3-yl)-acetic acid ethyl ester, the title compound was synthesised using the general procedure B2 for cyclization, followed by basic hydrolysis (D3) (0.66 g, 59% over two steps).
Mass (calculated) $C_{11}H_{12}BrNO_2$ [270]; found [M−1]=270-272 bromine pattern.

1-(5-Bromo-pyridin-3-yl)-cyclopentanecarboxylic Acid (5-bromo-pyrazin-2-yl)-amide Amide coupling was performed with thionyl chloride following the procedure E1 to give the title compound (0.021 g, 9%).
¹H NMR (400 MHz, Chloroform-d) δ 9.31 (d, J=1.7 Hz, 1H), 8.62 (dd, J=10.7, 2.1 Hz, 2H), 8.28 (d, J=1.7 Hz, 1H), 7.86 (t, J=2.1 Hz, 1H), 7.53 (s, 1H), 2.71-2.55 (m, 2H), 2.17-2.03 (m, 2H), 1.99-1.73 (m, 4H).
$C_{15}H_{14}N_4OBr_2$, Calculated [426.11], found [M+H⁺], 2Br pattern, 427, RT=1.61 (method f).

Example 6: 1-(5-Chloro-pyridin-3-yl)-cyclobutanecarboxylic Acid (5-chloro-pyridin-2-yl)-amide

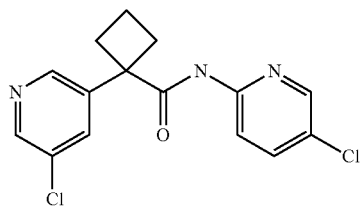 [SMILES: O=C(Nc1ccc(Cl)cn1)C1(c2cncc(Cl)c2)CCC1]

(5-Chloro-pyridin-3-yl)-acetic Acid tert-butyl ester

The title compound was synthesized from 3-bromo-5-chloropyridine using general procedure A2 for alkylation (8.20 g, 77%).
$C_{11}H_{14}ClNO_2$ Mass (calculated) [227]; found [M+1]=228-230 chlorine pattern.

1-(5-Chloro-pyridin-3-yl)-cyclobutanecarboxylic Acid tert-butyl ester

The title compound was prepared using the general procedure B2 for cyclization starting from (5-Chloro-pyridin-3-yl)-acetic acid tert-butyl ester and 1,3-diiodopropane (0.47 g, 37%).
$C_{14}H_{18}ClNO_2$ Mass (calculated) [267]; found [M+1]=268-270 chlorine pattern.

1-(5-Chloro-pyridin-3-yl)-cyclobutanecarboxylic Acid

The acid was obtained from 1-(5-Chloro-pyridin-3-yl)-cyclobutanecarboxylic acid tert-butyl ester using general procedure D2 for acid hydrolysis (0.33 g, quant.).
$C_{10}H_{10}ClNO_2$ Mass (calculated) [211]; found [M+1]=268-270 chlorine pattern.

1-(5-Chloro-pyridin-3-yl)-cyclobutanecarboxylic Acid (5-chloro-pyridin-2-yl)-amide Starting from 1-(5-Chloro-pyridin-3-yl)-cyclobutanecarboxylic acid and 5-bromo-pyridin-2-ylamine amide coupling was performed with thionyl chloride following the procedure E1 To give the title compound (0.05 g, 4%).
$^1$H NMR (400 MHz, Chloroform-d3) δ 8.56 (d, J=2.2 Hz, 1H), 8.53 (d, J=2.2 Hz, 1H), 8.20 (d, J=8.9 Hz, 1H), 8.17 (d, J=2.4 Hz, 1H), 7.70 (t, J=2.2 Hz, 1H), 7.67 (dd, J=8.9, 2.4 Hz, 1H), 7.58 (s, 1H), 3.03-2.90 (m, 2H), 2.64-2.51 (m, 2H), 2.25-2.09 (m, 1H), 2.09-1.94 (m, 1H).
$C_{15}H_{13}N_3OCl_2$, Calculated [322.19], found [M+H$^+$], 322, RT=1.53 (method f).

Example 7: 1-(6-Chloro-5-cyano-pyridin-3-yl)-cyclobutanecarboxylic Acid (5-chloro-pyridin-2-yl)-amide

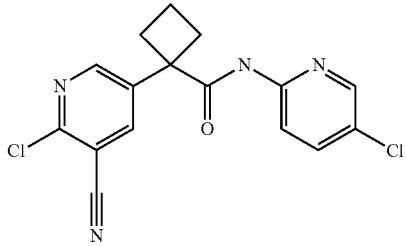 [SMILES: N#Cc1cc(C2(C(=O)Nc3ccc(Cl)cn3)CCC2)cnc1Cl]

(6-Chloro-5-cyano-pyridin-3-yl)-acetic Acid tert-butyl ester

The title compound was synthesized from 5-Bromo-2-chloronicotinonitrile using general procedure A2 for alkylation. (1.60 g, 35%).
Mass (calculated) $C_{12}H_{13}ClN_2O_2$ [252]; found [M+1]=253.

1-(6-Chloro-5-cyano-pyridin-3-yl)-cyclobutanecarboxylic Acid

The title compound was prepared using the general procedure B2 for cyclization, followed by acid hydrolysis using general procedure D2. (0.18 g, 30%).
Mass (calculated) $C_{11}H_9ClN_2O_2$ [236]; found [M+1]=237.

1-(6-Chloro-5-cyano-pyridin-3-yl)-cyclobutanecarboxylic Acid (5-chloro-pyridin-2-yl)-amide Amide coupling was performed following the procedure E1, starting from 1-(6-chloro-5-cyano-pyridin-3-yl)-cyclobutanecarboxylic acid and acid (5-chloro-pyridin-2-yl)-amine to give the title compound (0.066 g, 50%).
$^1$H NMR (400 MHz, Chloroform-d3) δ 8.64 (d, J=2.5 Hz, 2H), 8.24-8.07 (m, 2H), 8.03 (d, J=2.5 Hz, 1H), 7.76 (s, 1H), 7.69 (dd, J=9.0, 2.5 Hz, 1H), 3.17-2.71 (m, 2H), 2.64-2.29 (m, 2H), 2.36-1.92 (m, 2H).
$C_{16}H_{12}N_4OCl_2$, Calculated [347.20], found [M+H$^+$], 347, RT=1.59 (method f).

Example 8: 2-(6-Chloro-5-cyano-pyridin-3-yl)-pentanoic Acid (5-chloro-pyrazin-2-yl)-amide

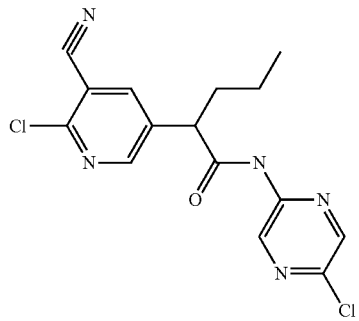 [SMILES: CCCC(C(=O)Nc1cnc(Cl)cn1)c1cnc(Cl)c(C#N)c1]

(6-Chloro-5-cyano-pyridin-3-yl)-acetic Acid tert-butyl ester

The title compound was synthesized following the general procedure A2 starting from 5-bromo-2-chloro-nicotinonitrile. The crude product was purified by silica gel chromatography (cHex/AcOEt gradient) to give the title compound (0.85 g, 75% y).

$^1$H NMR (400 MHz, CDCl3) δ 8.47 (s, 1H), 7.97 (s, 1H), 3.58 (s, 2H), 1.46 (s, 9H).

2-(6-Chloro-5-cyano-pyridin-3-yl)-pentanoic Acid tert-butyl ester

Alkylation was performed following the general procedure B1 starting from (6-Chloro-5-cyano-pyridin-3-yl)-acetic acid tert-butyl ester, to give the title compound (0.60 g, 60% y).

$C_{15}H_{19}ClN_2O_2$ Mass (calculated) [294]; (found) [M+H]$^+$=295.

2-(6-Chloro-5-cyano-pyridin-3-yl)-pentanoic Acid

The title compound was synthesized following the general procedure D2 starting from 2-(6-Chloro-5-cyano-pyridin-3-yl)-pentanoic acid tert-butyl ester; (0.12 g, 98% y). $C_{11}H_{11}ClN_2O_2$ Mass (calculated) [238]; (found) [M+H]$^+$=239.

2-(6-Chloro-5-cyano-pyridin-3-yl)-pentanoic Acid (5-chloro-pyrazin-2-yl)-amide The title product was synthesized following the general procedure E2 starting from 2-(6-Chloro-5-cyano-pyridin-3-yl)-pentanoic acid and 5-Chloro-pyrazin-2-ylamine, (0.10 g, 53%).

$^1$H NMR (400 MHz, Chloroform-d3) δ 9.30 (s, 1H), 8.56 (d, J=2.3 Hz, 1H), 8.27 (s, 1H), 8.18 (d, J=2.3 Hz, 1H), 7.92 (s, 1H), 3.59 (t, J=7.6 Hz, 1H), 2.27-2.12 (m, 1H), 1.90-1.80 (m, 1H), 1.46-1.19 (m, 2H), 0.98 (t, J=7.3 Hz, 3H).

$C_{15}H_{13}N_5OCl_2$, Calculated [350.20], found [M+H$^+$], 2 Cl pattern 350-352, RT=1.60 (method f).

Example 9: 2-(6-Chloro-5-fluoro-pyridin-3-yl)-pentanoic Acid (5-bromo-pyrazin-2-yl)-amide

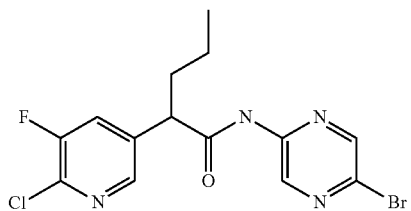 [SMILES: CCCC(C(=O)Nc1cnc(Br)cn1)c1cnc(Cl)c(F)c1]

(6-Chloro-5-fluoro-pyridin-3-yl)-acetic Acid tert-butyl ester

The title compound was synthesized following the general procedure A2 starting from 5-bromo-2-chloro-3-fluoro-pyridine. The crude product was purified by silica gel chromatography (cHex/AcOEt gradient) to give (6-Chloro-5-fluoro-pyridin-3-yl)-acetic acid tert-butyl ester (0.36 g, 30%).

$C_{11}H_{13}ClFNO_2$ Mass (calculated) [245]; (found) [M+H]$^+$=246.

2-(6-Chloro-5-fluoro-pyridin-3-yl)-pentanoic Acid tert-butyl ester

The title compound was synthesized following the general procedure B1 starting from (6-Chloro-5-fluoro-pyridin-3-yl)-acetic acid tert-butyl ester. The crude product was purified by silica gel chromatography (cHex/AcOEt gradient) to give 2-(6-Chloro-5-fluoro-pyridin-3-yl)-pentanoic acid tert-butyl ester (0.17 g, 56%).

$C_{14}H_{19}ClFNO_2$ Mass (calculated) [287]; (found) [M+H]$^+$=288.

2-(6-Chloro-5-fluoro-pyridin-3-yl)-pentanoic Acid

The title compound was synthesized following the general procedure D2 starting from (2-(6-Chloro-5-fluoro-pyridin-3-yl)-pentanoic acid tert-butyl ester (0.16 g, quant.). $C_{10}H_{11}ClFNO_2$ Mass (calculated) [231]; (found) [M+H]$^+$=232.

2-(6-Chloro-5-fluoro-pyridin-3-yl)-pentanoic Acid (5-bromo-pyrazin-2-yl)-amide The title compound was synthesized following the general procedure E1 starting from 2-(6-Chloro-5-fluoro-pyridin-3-yl)-pentanoic acid and 5-Bromo-pyrazin-2-ylamine (0.03 g, 33%).

$^1$H NMR (400 MHz, Methanol-d4) δ 9.20 (d, J=1.5 Hz, 1H), 8.45 (d, J=1.5 Hz, 1H), 8.23 (d, J=1.9 Hz, 1H), 7.84 (dd, J=9.4, 1.9 Hz, 1H), 3.90 (dd, J=8.3, 7.0, Hz, 1H), 2.20-2.06 (m, 1H), 1.86-1.72 (m, 1H), 1.47-1.19 (m, 2H), 0.96 (t, J=7.4 Hz, 3H).

$C_{14}H_{13}N_4OFClBr$, Calculated [387.63], found [M+H$^+$], Cl—Br pattern 389, RT=1.77 (method f).

Example 10: 2-(5-Bromo-pyridin-3-yl)2-Fluoro-pentanoic Acid (5-bromo-pyridin-2-yl) amide

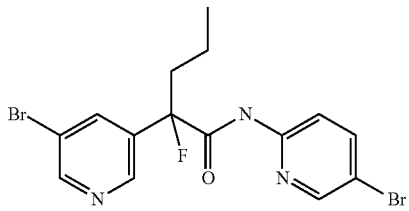 [SMILES: CCCC(F)(C(=O)Nc1ccc(Br)cn1)c1cncc(Br)c1]

2-(5-Bromo-pyridin-3-yl)-pentanoic Acid

To a solution of (5-Bromo-pyridil-3-yl) acetic acid (2.0 g, 9.3 mmol, 1 eq) in anhydrous THF cooled to −78° C., a solution of LiHMDS (20.4 mL, 20.4 mmol, 2.2 eq) in THF was added. The resulting mixture was stirred at −78° C. for 1 hour. Then 1-iodopropane (1.0 mL, 10.2 mmol, 1.1 eq) was added portionwise and the reaction mixture was allowed to warm up to room temperature and left stirring overnight. The reaction mixture was quenched with $_{H_2O}$ and extracted with AcOEt. The aqueous layer was separated; the solution was acidified to pH=3 with 6N HCl and extracted with AcOEt. The organic phases were collected, dried over Na$_2$SO$_4$ and concentrated under reduced pressure. The crude product was purified by silica gel chromatography (cHex: AcOEt 92:8 to 34:66) to give the title compound (1.2 g, 50%).

$C_{10}H_{12}BrNO_2$ mass (calculated) [258]; (found) $[M+H]^+=259$ m/z.

2-(5-Bromo-pyridin-3-yl)-pentanoic ethyl ester

To a solution of 2-(5-Bromo-pyridin-3-yl)-pentanoic acid (1.50 g, 5.8 mmol, 1 eq) in EtOH (10 mL), $H_2SO_4$ (0.5 mL, 2.6 eq, 15.2 mmol) was added and the mixture was stirred at 85° C. for 12 hours. Then the mixture was allowed to cool to room temperature. The mixture was concentrated under reduced pressure, dissolved in DCM and washed with sodium bicarbonate saturated solution. The organic layer was collected and the solvent was removed under reduce pressure to give the desired product employed in the next step without further purification (1.5 g, 88%).

$C_{12}H_{16}BrNO_2$ mass (calculated) [286]; (found) $[M+H]^+=287$ m/z.

2-(5-Bromo-pyridin-3-yl)-2-fluoro-pentanoic ethyl ester

A solution of LiHDMS (1M in THF, 0.58 mL, 1.1 eq) was diluted with THF (2.0 mL) and cooled to −78° C.; a solution of the 2-(5-Bromo-pyridin-3-yl)-pentanoic ethyl ester (0.15 g, 0.52 mmol, 1.0 eq) in the same solvent (1.0 mL) was added dropwise. The mixture was stirred at 0° C. for 30 minutes and then cooled to −78° C. again. A solution in THF (2.0 mL) of N-fluorobenzene sulfonimide (0.22 g, 0.68 mmol, 1.3 eq) was added dropwise; the mixture was then warmed to room temperature and stirred for 12 hours. The reaction was quenched with $NH_4Cl$ saturated aqueous solution, extracted with AcOEt and washed with $H_2O$. The organic layer was collected and the solvent was removed under reduce pressure. The crude product was purified by silica gel chromatography (cHex:AcOEt 100:0 to 80:20) give the desired product as an orange oil (0.10 g, 63%).

$C_{12}H_{15}BrFNO_2$ mass (calculated) [304]; (found) $[M+H]^+=305$ m/z.

2-(5-Bromo-pyridin-3-yl)-2-fluoro-pentanoic carboxylic Acid

To a solution of 2-(5-Bromo-pyridin-3-yl)-2-fluoro-pentanoic ethyl ester (0.48 g, 1.6 mmol, 1 eq) in MeOH (3 mL), a solution of 2N NaOH (3 mL, 6 mmol, 4 eq) was added and the mixture was stirred at room temperature for 3 hours. The solvent was removed under reduced pressure, the residue was suspended in $H_2O$ and the mixture was acidified with 1N HCl to pH=3. The aqueous phase was extracted with DCM and the organic layer was collected and dried over $Na_2SO_4$. The title compound was isolated without further purification (0.41 g, 95%).

$C_{10}H_{11}BrFNO_2$ Mass (calculated) [276]; (found) $[M+H]^+=277$ m/z.

2-(5-Bromo-pyridin-3-yl)2-Fluoro-pentanoic Acid (5-bromo-pyridin-2-yl)-amide

To a solution of 2-(5-Bromo-pyridin-3-yl)-2-fluoro-pentanoic carboxylic acid (0.12 g, 0.44 mmol, 1 eq) in DMF (1.5 mL), 5-Bromo-2-aminopyridine (0.08 g, 0.48 mmol, 1.1 eq), 1-hydroxybenzotriazole hydrate (0.02 g, 0.13 mmol, 0.3 eq) and EDC (0.10 g, 0.52 mmol, 1.2 eq) were added. The mixture was stirred at room temperature for one hour. $NaHCO_3$ saturated solution was added and the mixture was extracted with DCM. The combined organic extracts were washed with saturated NaCl solution, dried over $Na_2SO_4$ and evaporated. The crude product was purified by silica gel chromatography (cHex:AcOEt 100:0 to 77:23) to give the title compound (0.07 g, 38%).

$^1$H NMR (400 MHz, Chloroform-d3) δ 8.76-8.68 (m, 2H), 8.61 (d, J=2.3 Hz, 1H), 8.29 (d, J=2.4 Hz, 1H), 8.05 (d, J=8.8 Hz, 1H), 8.01 (t, J=2.3 Hz, 1H), 7.76 (dd, J=8.8, 2.4 Hz, 1H), 2.42-2.21 (m, 1H), 2.18-1.99 (m, 1H), 1.47-1.31 (m, 2H), 0.89 (t, J=7.4 Hz, 3H).

$C_{15}H_{14}Br_2FN_3O$, Calculated [431.10], found $[M+H^+]$, 432, RT=2.35 (method e).

Example 11: 2-(5-Bromo-pyridin-3-yl)-2-methyl-pentanoic Acid (5-bromo-pyrazin-2-yl)-amide

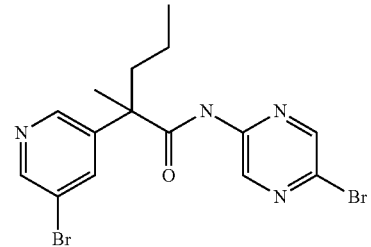 [SMILES: CCCC(C)(C(=O)Nc1cnc(Br)cn1)c1cncc(Br)c1]

2-(5-Bromo-pyridin-3-yl)-propionic Acid (5-Bromo-pyridin-3-yl)-acetic acid was alkylated with iodomethane using general procedure B1 for the alkylation of acid to give the title product (0.6 g, 61%).

$C_8H_8BrNO_2$ Mass (calculated) [230]; found [M+1]=230-232 bromine pattern.

2-(5-Bromo-pyridin-3-yl)-2-methyl-pentanoic Acid 2-(5-Bromo-pyridin-3-yl)-propionic acid was alkylated using general procedure B1 for the alkylation, heating at 50° C. to give the title compound (0.1 g, 28%). $C_{11}H_{14}BrNO_2$ Mass (calculated) [272]; found [M+1]=272-274 bromine pattern.

2-(5-Bromo-pyridin-3-yl)-2-methyl-pentanoic Acid (5-bromo-pyrazin-2-yl)-amide

Amide coupling was performed with thionyl chloride following the procedure E1, starting from 2-(5-bromo-pyridin-3-yl)-2-methyl-pentanoic acid and 5-bromo-pyrazin-2-yl)-amine to give the title compound after preparative HPLC in basic condition (0.02 g, 10%).

$^1$H NMR (400 MHz, DMSO-d6) δ 10.45 (s, 1H), 9.10 (d, J=2.1 Hz, 1H), 8.61-8.53 (m, 2H), 8.44 (d, J=2.1 Hz, 1H), 7.91 (t, J=2.1 Hz, 1H), 2.16-2.03 (m, 1H), 2.01-1.83 (m, 1H), 1.57 (s, 3H), 1.20-1.02 (m, 2H), 0.85 (t, J=7.1 Hz, 3H).

$C_{15}H_{16}N_4OBr_2$, Calculated [428.1], found $[M+H^+]$, 2Br pattern 429, RT=1.66 (method f).

Example 12: 2-(6-Bromo-pyridin-2-yl)-pentanoic Acid (5-bromo-pyrazin-2-yl)-amide

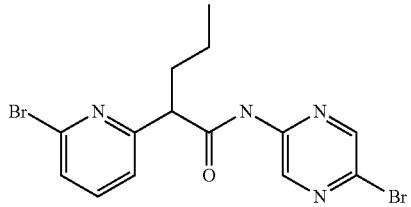 [SMILES: CCCC(C(=O)Nc1cnc(Br)cn1)c1cccc(Br)n1]

(6-Bromo-pyridin-2-yl)-acetic Acid ethyl ester

To a solution of N,N-diisopropylamine (1.85 g, 18.31 mmol) in anhydrous THF (7 mL) cooled to −78° C., a solution of n-butyllithium (2.5 M in hexane, 17.44 mmol) was added drop wise under inert atmosphere. The mixture was stirred at −78° C. for one hour and then 2-bromo-6-methylpyridine (1.5 g, 8.7 mmol). The reaction mixture was stirred at −78° C. for one hour and a solution of diethyl carbonate (1.23 g, 10.46 mmol) in THF (3 mL) was added. The reaction mixture was allowed to warm up to room temperature and left stirring overnight. The mixture was quenched with $H_2O$ and extracted twice with AcOEt. The organic layer was collected, washed with saturated sodium chloride solution, dried over $Na_2SO_4$ and concentrated under reduced pressure. The crude was purified by chromatography on silica gel (cHex/AcOEt 70/30) to give the title compound as an yellow oil (1.16 g, 55%).

$C_9H_{10}BrNO_2$ Mass (calculated) [244]; (found) [M+H]$^+$=246.

2-(6-Bromo-pyridin-2-yl)-pentanoic Acid ethyl ester

The title compound was obtained following the general procedure B1 and starting from (6-bromo-pyridin-2-yl)-acetic acid ethyl ester (0.85 g, 63%).

$C_{12}H_{16}BrNO_2$ Mass (calculated) [286]; (found) [M+H]$^+$=288.

2-(6-Bromo-pyridin-2-yl)-pentanoic Acid

To a solution of 2-(6-bromo-pyridin-2-yl)-pentanoic acid ethyl ester (0.40 g, 1.4 mmol) in MeOH (3 mL), a solution of 2N NaOH (3 ml) was added and the mixture was stirred at room temperature for 3 hours. The solvent was removed under reduced pressure, the crude product was suspended in $H_2O$ and the mixture was acidified with 1N HCl to pH3. The aqueous phase was extracted with DCM and the organic layer was collected and dried over $Na_2SO_4$. The title compound was obtained in quantitative yield without further purification.

$C_{10}H_{12}BrNO_2$ Mass (calculated) [258]; (found) [M+H]$^+$=260.

2-(6-Bromo-pyridin-2-yl)-pentanoic Acid (5-bromo-pyrazin-2-yl)-amide

To a solution of 2-(2-bromo-pyridin-4-yl)-pentanoic acid (0.12 g, 0.47 mmol) in DMF (1.5 mL), 5-bromo-pyrazin-2-ylamine (0.09 g, 0.51 mmol), 1-hydroxybenzotriazole hydrate (0.02 g, 0.17 mmol) and EDC (0.13 g, 0.70 mmol) were added. The mixture was stirred at room temperature for one hour. NaHCO$_3$ saturated solution was added and the mixture was extracted with DCM. The combined organic extracts were washed with saturated NaCl solution, dried over Na$_2$SO$_4$ and evaporated. The crude product was purified by silica gel chromatography (cHex/AcOEt 75/25) to give the title compound (0.02 g, 8%).

$^1$H NMR (400 MHz, Chloroform-d3) δ 9.59 (s, 1H), 9.29 (d, J=1.4 Hz, 1H), 8.37 (d, J=1.4 Hz, 1H), 7.57 (t, J=7.7 Hz, 1H), 7.45 (d, J=7.7 Hz, 1H), 7.27 (d, J=7.7 Hz, 1H), 3.75 (t, J=7.7 Hz, 1H), 2.21-2.16 (m, 1H), 2.08-1.92 (m, 1H), 1.45-1.21 (m, 2H), 0.95 (t, J=7.3 Hz, 3H).

$C_{15}H_{15}Br_2N_3O$, Calculated [414.09], found [M+H$^+$] 415, RT=1.71 (method f).

Example 13: 2-(2-Bromo-pyridin-4-yl)-pentanoic Acid (5-bromo-pyridin-2-yl)-amide

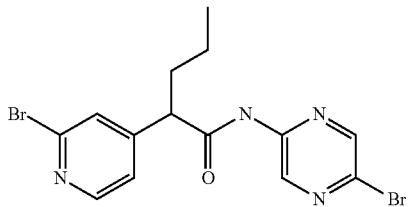 [SMILES: CCCC(C(=O)Nc1cnc(Br)cn1)c1ccnc(Br)c1]

(2-Bromo-pyridin-4-yl)-acetic Acid tert-butyl ester

To a solution of diisopropylamine (2.1 g, 20.93 mmol) in anhydrous THF (30 mL) under nitrogen, cooled at −78° C., a solution of n-butyllithium in hexane (2.5 M, 19.18 mmol) was added dropwise. The mixture was allowed to warm up to −30° C. and left stirring for 30 minutes. Then the reaction was cooled again to −78° C. and a solution of 2-bromo-4-methylpyridine (3.0 g, 17.44 mmol) in THF (10 mL) was added. The reaction turned to dark orange and it was stirred at −30° C. for 30 minutes. Then the reaction was cooled to −78° C. and a solution of di-tert-butyl dicarbonate (0.18 g, 19.18 mmol) in THF (10 ml) was added. Then the reaction mixture was allowed to warm up to room temperature and let stirring overnight. The mixture was quenched with H$_2$O and extracted with AcOEt twice. The organic layer was separated, washed with NaCl saturate solution, dried over Na$_2$SO$_4$ and concentrated under reduced pressure. The crude was purified by silica gel chromatography (cHex/AcOEt 80/20) to give the title compound (0.81 g, 13%).

$C_{11}H_{14}BrNO_2$ Mass (calculated) [272]; (found) [M+H]$^+$=274.

2-(2-Bromo-pyridin-4-yl)-pentanoic Acid tert-butyl ester

The title compound was obtained following general procedure for alkylation B1 and starting from (2-bromo-pyridin-4-yl)-acetic acid tert-butyl ester (0.83 g, 3.05 mmol), (0.68 g, 71%).

$C_{14}H_2OBrNO_2$ Mass (calculated) [314]; (found) [M+H]$^+$=316.

2-(2-Bromo-pyridin-4-yl)-pentanoic Acid

To a solution of 2-(2-Bromo-pyridin-4-yl)-pentanoic acid tert-butyl ester (0.68 g, 2.16 mmol) in DCM (20 mL), trifluoroacetic acid (2 mL) was added and the mixture was stirred at room temperature for three days. The mixture was concentrated under reduced pressure, then was diluted with DCM and extracted with NaHCO₃ saturated solution. The aqueous layer was separated, acidified to pH3 with HCl 1N and extracted with DCM. The organic phase was separated, dried over Na₂SO₄ and concentrated under reduced pressure, affording the title compound (0.44 g, 72%).

$C_{10}H_{12}BrNO_2$ Mass (calculated) [258]; (found) [M+H]⁺=260.

2-(2-Bromo-pyridin-4-yl)-pentanoic Acid (5-bromo-pyridin-2-yl)-amide

The title compound was obtained following the general procedure E2 for coupling with EDC and starting from 2-(2-bromo-pyridin-4-yl)-pentanoic acid and 5-bromo-pyridin-2-ylamine (0.05 g, 30%).

¹H NMR (400 MHz, Chloroform-d3) δ 8.34 (d, J=5.1 Hz, 1H), 8.31 (d, J=2.5 Hz, 1H), 8.13 (d, J=8.8 Hz, 1H), 7.89 (s, 1H), 7.81 (dd, J=8.8, 2.5 Hz, 1H), 7.52 (s, 1H), 7.28 (m, 1H), 3.42 (t, J=7.5 Hz, 1H), 2.23-2.09 (m, 1H), 1.88-1.74 (m, 1H), 1.34 (m, 2H), 0.96 (t, J=7.3 Hz, 3H).

$C_{15}H_{15}Br_2N_3O$, Calculated [413.11], found [M+H⁺] 414, RT=1.75 (method f).

Example 14: 2-(2-Methoxy-pyridin-4-yl)-pentanoic Acid (5-bromo-pyridin-2-yl)-amide

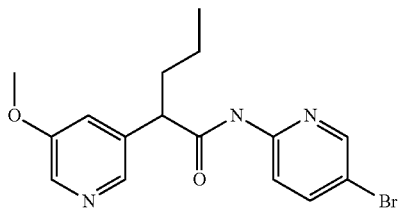 [SMILES: CCCC(C(=O)Nc1ccc(Br)cn1)c1cncc(OC)c1]

2-(Methoxy-pyridin-4-yl)-acetic Acid ethyl ester

The title compound was synthesized following the general procedure A1 starting from 2-methoxy-4-methyl-pyridine. (4.63 g, 73%) $C_{10}H_{13}NO_3$ Mass (calculated) [195]; (found) [M+H]⁺=196.

2-(2-Methoxy-pyridin-4-yl)-pentanoic Acid ethyl ester

The title compound was synthesized following the general procedure B1 starting 2-methoxy-pyridin-4-yl)-acetic acid ethyl ester. Title compound was obtained in (0.75 g, 75%).

$C_{13}H_{19}NO_3$ Mass (calculated) [237]; (found) [M+H]⁺=238.

2-(2-Methoxy-pyridin-4-yl)-pentanoic Acid (5-bromo-pyridin-2-yl)-amide

To 2-(2-Methoxy-pyridin-4-yl)-pentanoic acid ethyl ester (0.150 g, 0.6 mmol, 1 eq) 1,5,7-Triazabicyclo[440]dec-5-ene (0.03 g, 0.2 mmol, 0.3 eq) and 2-amino-5-bromopyridine (0.44 g, 2.5 mmol, 4 eq) were added in a vessel that was sealed with a septum and placed into the microwave cavity. Microwave irradiation (maximum emitted power 230W) was used to increase the temperature to 130° C. The reaction mixture was then kept at this temperature for 30 min. Then the residue was diluted with DCM and washed with NaHCO₃ saturated solution. The organic phase was separated, dried over Na₂SO₄ and concentrated in vacuo. The crude was purified by silica gel chromatography (cHex/AcOEt gradient) to give the title compound (0.03 g, 15%).

¹H NMR (400 MHz, Chloroform-d3) δ 8.29-8.23 (m, 1H), 8.18-8.09 (m, 2H), 7.98 (s, 1H), 7.83-7.74 (m, 1H), 6.90-6.82 (m, 1H), 6.72 (s, 1H), 3.93 (s, 3H), 3.43 (t, J=7.5 Hz, 1H), 2.22-2.07 (m, 1H), 1.88-1.74 (m, 1H), 1.41-1.21 (m, 2H), 0.93 (t, J=7.3, 1.5 Hz, 3H).

$C_{16}H_{15}BrN_3O_2$, Calculated [364.24], found [M+H⁺], Br pattern 364-366, RT=1.65 (method f).

Example 15: 2-(2-Methoxy-pyridin-4-yl)-pentanoic Acid (5-chloro-thiazol-2-yl)-amide

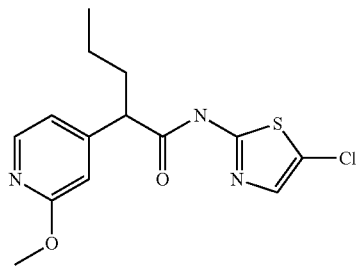 [SMILES: CCCC(C(=O)Nc1ncc(Cl)s1)c1ccnc(OC)c1]

2-(2-Methoxy-pyridin-4-yl)-pentanoic Acid

The title compound was synthesized following the general procedure D3 starting from 2-(2-methoxy-pyridin-4-yl)-pentanoic acid ethyl ester. (1.50 g, 79%).

Mass (calculated) $C_{11}H_{15}NO_3$ [209]; (found) [M+H⁺]=210.

Synthesis of 2-(2-Methoxy-pyridin-4-yl)-pentanoic Acid (5-chloro-thiazol-2-yl)-amide The title compound was synthesized following the general procedure E1 starting from 2-(2-methoxy-pyridin-4-yl)-pentanoic acid and 5-chloro-thiazol-2-ylamine (0.04 g, y 16%).

¹H NMR (400 MHz, Chloroform-d3) δ 10.11 (bp, 1H), 8.14 (d, J=5.4 Hz, 1H), 7.23 (s, 1H), 6.86 (dd, J=5.4, 1.4 Hz, 1H), 6.72 (d, J=1.4 Hz, 1H), 3.94 (s, 3H), 3.56 (t, J=7.5 Hz, 1H), 2.29-2.04 (m, 1H), 1.95-1.66 (m, 1H), 1.43-1.19 (m, 2H), 0.94 (t, J=7.3 Hz, 3H). $C_{14}H_{16}N_3O_2SCl$, Calculated [325.81], found [M+H⁺], 326, RT=2.01 (method e).

Example 16: 2-(6-Chloro-pyridin-3-yl)-pentanoic Acid (5-bromo-pyridin-2-yl)-amide

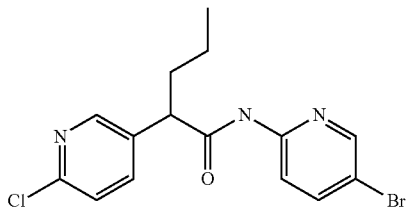 [SMILES: CCCC(C(=O)Nc1ccc(Br)cn1)c1ccc(Cl)nc1]

(6-Chloro-pyridin-3-yl)-acetic Acid ethyl ester

To a solution of EtOH (27 mL), concentrated $H_2SO_4$ (10 mL) was added dropwise and 2-chloropyridine-5-acetonitrile (2.00 g, 13.1 mmol) was added portionwise. The solution was stirred at 100° C. for three hours. The mixture was added dropwise to a solution of $NaHCO_3$ (30.00 g) in $H_2O$ (100 mL) and it was extracted twice with DCM. The organic layer were collected, dried and evaporated to give the title compound (2.60 g, quant.)

$C_9H_{10}ClNO_2$ Mass (calculated) [199]; (found) $[M+H]^+=200$.

2-(6-Chloro-pyridin-3-yl)-pentanoic Acid ethyl ester

The title compound was obtained following general procedure B1 for alkylation and starting from (6-chloro-pyridin-3-yl)-acetic acid ethyl ester (0.72 g, 45%). $C_{12}H_{16}ClNO_2$ Mass (calculated) [241]; (found) $[M+H]^+=242$.

2-(6-Chloro-pyridin-3-yl)-pentanoic Acid 2-(6-Chloro-pyridin-3-yl)-pentanoic acid ethyl ester (0.72 g, 2.96 mmol) was dissolved in concentrated HCl (8 mL) and the solution was stirred at 100° C. for two hours. The mixture was concentrated under reduce pressure and the crude product was used in the next step without further purification (1.00 g, quant.).

$C_{10}H_{12}ClNO_2$ Mass (calculated) [213]; (found) $[M+H]^+=214$.

2-(6-Chloro-pyridin-3-yl)-pentanoic Acid (5-bromo-pyridin-2-yl)-amide

The title compound was obtained following general procedure E1 for amide coupling and starting from 2-(6-Chloro-pyridin-3-yl)-pentanoic acid and 5-bromo-pyridin-2-ylamine, (0.12 g, 65%).

$C_{15}H_{15}BrClN_3O$ Mass (calculated) [368]; (found) $[M+H]^+=370$.

Example 17: 2-(5-Bromo-pyridin-3-yl)-N-(5-bromo-pyridin-2-yl)-3-(5-trifluoromethyl-furan-2-yl)-propionamide

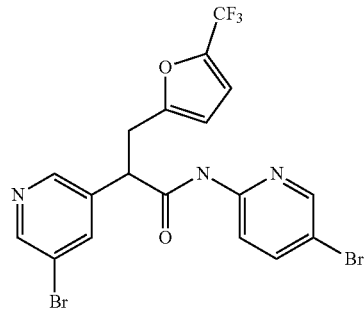 [SMILES: O=C(Nc1ccc(Br)cn1)C(Cc1ccc(C(F)(F)F)o1)c1cncc(Br)c1]

2-(5-Bromo-pyridin-3-yl)-3-(5-trifluoromethyl-furan-2-yl)-propionic Acid ethyl ester The title compound was obtained starting from (5-bromo-pyridin-3-yl)-acetic acid ethyl ester and 2-bromomethyl-5-methyl-furan following general procedure B1 for alkylation (0.33 g, 72%).

$C_{15}H_{13}BrF_3NO_3$ Mass (calculated) [392]; found [M+1] 392-394 bromine pattern.

2-(5-Bromo-pyridin-3-yl)-3-(5-trifluoromethyl-furan-2-yl)-propionic Acid

The title compound was obtained using general procedure D3 for ester hydrolysis and starting from 2-(5-bromo-pyridin-3-yl)-3-(5-trifluoromethyl-furan-2-yl)-propionic acid ethyl ester (0.30 g, quant.).

$C_{13}H_9BrF_3NO_3$ Mass (calculated) [364]; found [M+1] 364-366 bromine pattern.

2-(5-Bromo-pyridin-3-yl)-N-(5-bromo-pyridin-2-yl)-3-(5-trifluoromethyl-furan-2-yl)-propionamide Acid (0.06 g, 0.165 mmol, 1 eq) and 5-bromo-2-aminopyridine (0.029 g, 0.165 mmol, 1 eq) were dissolved in AcOEt (2 mL), DIPEA (0.057 mL, 0.33 mmol, 2 eq) were added and solution cooled to 0° C. T3P 50% solution in AcOEt (0.127 mL, 0.33 mmol, 1.5 eq) was added and reaction was stirred for 12 h at room temperature. NaHCO3 saturated solution (2 mL) was added; organic layer was separated, dried over Na2SO4, filtered and evaporated. The crude product was purified by silica gel chromatography (cHex/0-35% AcOEt) to give the title compound (0.08 g, 78%).

$^1$H NMR (400 MHz, Chloroform-d3) δ 8.63 (d, J=2.2 Hz, 1H), 8.45 (d, J=2.0 Hz, 1H), 8.30 (d, J=2.4 Hz, 1H), 8.12 (d, J=8.9 Hz, 1H), 7.97 (bs, 1H), 7.92 (t, J=2.0 Hz, 1H), 7.82 (dd, J=8.8, 2.4 Hz, 1H), 6.63 (d, J=3.3, 1H), 6.09 (d, J=3.3 Hz, 1H), 3.95 (t, J=7.7 Hz, 1H), 3.59 (m, 1H), 3.17 (m, 1H).

$C_{15}H_{12}N_3O_2F_3Br_2$, Calculated [519.11], found $[M+H^+]$, 520, RT=1.81 (method f).

Example 18: 2-(6-Methoxy-pyridin-3-yl)-pentatonic Acid (5-bromo-pyridin-2-yl)-amide

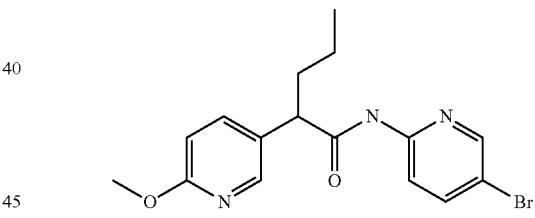

Cyano-(6-methoxy-pyridin-3-yl)-acetic Acid ethyl ester

Ethyl cyanoacetate (0.938 mL, 8.8 mmol, 1 eq) and 5-bromo-2-methoxy-pyridine (1.3 mL, 10 mmol, 1.2 eq) were added to a suspension of potassium tert-butoxide (2.4 g, 21.4 mmol, 2.5 eq) in 1,4-dioxane (25 mL) dry under $N_2$ atmosphere. A solution of palladium acetate (0.039 g, 0.17 mmol, 0.02 eq) and Qphos (0.198 g, 0.39 mmol, 0.04 eq) in 1,4-dioxane (10 mL) dry was added dropwise to reaction mixture. The reaction was heated at 70° C. for 2 h before cooling to room temperature; 1N acetic acid solution (15 mL) and AcOEt (20 mL) were added, organic layer was collected, dried over $Na_2SO_4$ and evaporated. The crude product was purified by silica gel chromatography with (cHex-10% AcOEt) to give the title compound (1.13 g, 60%).

$C_{11}H_{12}N_2O_3$ Mass (calculated) [220]; (found) $[M+H]^+=221$.

2-Cyano-2-(6-methoxy-pyridin-3-yl)-pentanoic Acid ethyl ester

Cyano-(6-methoxy-pyridin-3-yl)-acetic acid ethyl ester (1.13 g, 5.1 mmol, 1 eq) was dissolved in dimethylformamide (10 mL), cesium carbonate (2 g, 6.12 mmol, 1.2 eq) and 1-iodo-propane (0.55 mL, 5.6 mmol, 1.1 eq) were added and the mixture was stirred at room temperature overnight. $H_2O$ (500 mL) was added and crude extracted three times with AcOEt (3×100 mL). Organic phases were combined, dried over Na2SO4 and concentrated in vacuo. The crude product was purified by silica gel chromatography (cHex-10% AcOEt) to give the title compound (1 g, 74%).

$C_{14}H_{18}N_2O_3$ Mass (calculated) [262]; (found) $[M+H]^+=263$.

2-(6-Methoxy-pyridin-3-yl)-pentanoic acid 2-cyano-2-(6-methoxy-pyridin-3-yl)-pentanoic acid ethyl ester (1 g, 3.8 mmol, 1 eq) was dissolved in methanol (7.5 mL) NaOH 2N solution (7.5 mL, 15 mmol, 4 eq) was added and mixture was stirred one hour at room temperature and at 60° C. for 2 hours. The reaction mixture was acidified to pH=5 with HCl 1 N and extracted with AcOEt (3×20 ml). Organic layers were collected, dried over $Na_2SO_4$ and concentrated in vacuo. The crude product was purified by silica gel chromatography (cHex-33% AcOEt) to give the title compound (0.65 g, 82%).

$C_{11}H_{15}NO_3$ Mass (calculated) [209]; (found) $[M+H]^+=210$.

2-(6-Methoxy-pyridin-3-yl)-pentatonic Acid (5-bromo-pyridin-2-yl)-amide

The amide coupling was performed using general procedure E1 to give the title compound (0.01 g, 5%).

$^1$H NMR (400 MHz, Chloroform-d) δ 8.42 (s, 1H), 8.26 (d, J=2.5 Hz, 1H), 8.22-8.11 (m, 2H), 7.79 (dd, J=8.9, 2.5 Hz, 1H), 7.72 (dd, J=8.7, 2.6 Hz, 1H), 6.80 (d, J=8.7 Hz, 1H), 3.97 (s, 3H), 3.58 (t, J=7.7 Hz, 1H), 2.21-2.10 (m, 1H), 1.92-1.65 (m, 1H), 1.49-1.15 (m, 2H), 0.93 (t, J=7.3 Hz, 3H).

$C_{16}H_{18}N_3O_2Br$, Calculated [364.24], found $[M+H^+]$, Br pattern 364-366, RT=1.67 (method f).

Example 19: 2-(5-Bromo-2,3-dihydro-indol-1-yl)-pentanoic Acid (5-bromo-pyridin-2-yl)-amide

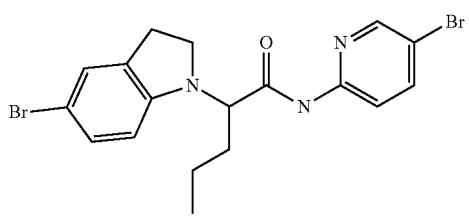 [SMILES: CCCC(C(=O)Nc1ccc(Br)cn1)N1CCc2cc(Br)ccc21]

2-Bromo-pentanoic acid (5-bromo-pyridin-2-yl)-amide

2-Bromopentanoic acid (2.17 mL, 16.57 mmol, 1 eq) was dissolved in dichloroethane (15 mL) solution was reach to 0° C., Oxalyl chloride (2.90 mL, 33.15 mmol, 2 eq) was added follow by 1 drop of DMF and reaction was stirred at room temperature for 5 h. Solution was evaporated to dryness. Acyl chloride was dissolved in dichloroethane (15 mL) and slowly added to a solution of 5-bromo-2-aminopyridine (3.1 g, 18.23 mmol, 1.1 eq) and DIPEA (5.78 mL, 33.15 mmol, 2 eq) in dichloroethane over a period of 10 minutes; reaction was stirred at room temperature for 1 h. $NaHCO_3$ saturated solution was added, organic phase was collected, washed with a saturated solution of NaCl, dried over Na2SO4, filtered and evaporated. The crude product was purified by silica gel chromatography (cHex-5% AcOEt) to give the title compound (3.3 g, 65%).

$C_{10}H_{12}Br_2N_2O$ Mass (calculated) [336]; found [M+1]=336-338 bromine pattern.

2-(5-Bromo-2,3-dihydro-indol-1-yl)-pentanoic Acid (5-bromo-pyridin-2-yl)-amide 2-Bromo-pentanoic acid (5-bromo-pyridin-2-yl)-amide (0.13 g, 0.39 mmol, 1 eq) was dissolved in $CH_3CN$ (2 mL), DIPEA (0.081 mL, 0.46 mmol, 1.2 eq) and 5-bromoindoline (0.087 mL, 0.46 mmol, 1.2 eq) were added. Reaction was heated at 70° C. for 16 h. Acetonitrile was evaporated, the crude residue was partitioned in AcOEt (2 mL) and $H_2O$ (2 mL), organic phase was collected, dried over $Na_2SO_4$, filtered and evaporated. The crude product was purified by reverse phase chromatography to give the title compound (0.021 g, 12%).

$^1$H NMR (400 MHz, Chloroform-d3) δ 8.97 (s, 1H), 8.29 (d, J=2.5 Hz, 1H), 8.21 (d, J=8.8 Hz, 1H), 7.81 (dd, J=8.8, 2.5 Hz, 1H), 7.22 (d, J=2.0 Hz, 1H), 7.14 (dd, J=8.4, 2.0 Hz, 1H), 6.33 (d, J=8.4 Hz, 1H), 3.95 (dd, J=7.5, 6.4 Hz, 1H), 3.62-3.43 (m, 2H), 3.16-2.97 (m, 2H), 2.23-2.00 (m, 1H), 1.79 (m, 1H), 1.55-1.29 (m, 2H), 0.96 (t, J=7.3 Hz, 3H).

$C_{15}H_{19}N_3OBr_2$, Calculated [453.17], found $[M+H^+]$, 2Br pattern 454, RT=2.12 (method f).

Example 20: 2-(5-Bromo-3-methyl-indol-1-yl)-pentanoic Acid (5-bromo-pyridin-2-yl)-amide

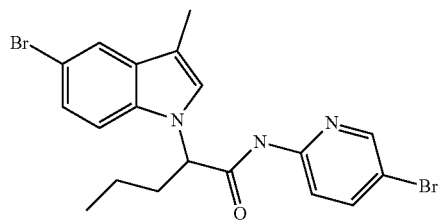 [SMILES: CCCC(C(=O)Nc1ccc(Br)cn1)n1cc(C)c2cc(Br)ccc21]

2-(5-Bromo-3-methyl-indol-1-yl)-pentanoic Acid ethyl ester

To a solution of 5-bromo-3-methyl-1H-indole (0.50 g, 2.38 mmol) in DMF (4 mL), NaH (60% in mineral oil, 0.11 g, 2.85 mmol) was added and the mixture was stirred at room temperature for 30 minutes. 2-Bromo-pentanoic acid ethyl ester (0.45 mL, 2.62 mmol) was added and the reaction was left stirring at room temperature overnight. Saturated NaCl solution was added and the mixture was extracted with DCM. The organic phase was collected, dried over $Na_2SO_4$ and concentrated under reduced pressure. The crude product was purified by silica gel chromatography (cHex/AcOEt 80/20) to afford the title compound (0.35 g, 46%).

$C_{16}H_{20}BrNO_2$ Mass (calculated) [338]; (found) $[M+H]^+=340$.

2-(5-Bromo-3-methyl-indol-1-yl)-pentanoic Acid (5-bromo-pyridin-2-yl)-amide

The title compound was obtained following general procedure F1 for amide coupling and starting from 2-(5-bromo-3-methyl-indol-1-yl)-pentanoic acid ethyl ester and 5-bromo-pyridin-2-ylamine (0.08 g, 34%).

$^1$H NMR (400 MHz, Chloroform-d) δ 8.20 (d, J=2.4 Hz, 1H), 8.15 (d, J=8.9 Hz, 1H), 7.79 (dd, J=8.9, 2.4 Hz, 1H), 7.76-7.71 (m, 2H), 7.32 (dd, J=8.7, 1.9 Hz, 1H), 7.16 (d, J=8.7 Hz, 1H), 7.01 (s, 1H), 4.90 (dd, J=10.7, 4.7 Hz, 1H), 2.48-2.36 (m, 1H), 2.34 (s, 3H), 2.23-2.07 (m, 1H), 1.33-1.12 (m, 2H), 0.93 (t, J=7.3 Hz, 3H).

$C_{19}H_{19}Br_2N_3O$, Calculated [465.18], found [M+H$^+$], 2Br pattern, 466, RT=5.38 (method c).

Example 21: 2-(3-Bromo-pyrrol-1-yl)-pentanoic Acid (5-bromo-pyridin-2-yl)-amide

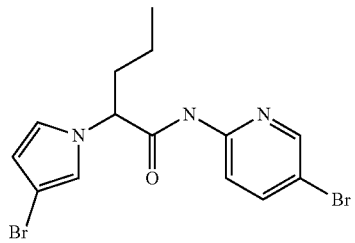 [SMILES: CCCC(C(=O)Nc1ccc(Br)cn1)n1ccc(Br)c1]

2-(3-Bromo-pyrrol-1-yl)-pentanoic Acid ethyl ester

To a solution of 3-bromo-1-triisopropylsilanyl-1H-pyrrole (1.10 g, 3.64 mmol) in THF (11 mL), a solution of tetrabutyl ammonium fluoride in THF (1M, 3.82 mL, 3.82 mmol) was added and reaction was stirred for 10 minutes at room temperature. 5 mL of diethyl ether were added and the mixture was washed with 10 mL of H$_2$O. The organic phase was collected, dried over Na$_2$SO$_4$ and concentrated under reduced pressure, obtaining 3-bromo-1H-pyrrole that was used without further purification. To a suspension of NaH (60% in mineral oil, 0.10 g, 4.11 mL) in THF (9 mL), under nitrogen atmosphere, a solution of 3-bromo-1H-pyrrole (0.50 g, 3.46 mmol) was added and the mixture was left stirring at room temperature for 1 hour. Then the reaction was cooled down to 0° C. and a solution of 2-bromo-pentanoic acid ethyl ester (0.86 g, 4.11 mmol) in DMF (9 mL) was added. The reaction was allowed to warm up to room temperature and was left stirring for 3 hours. Then H$_2$O was added (10 mL) and the mixture was extracted with AcOEt (10 mL), the organic phase was collected, dried over Na$_2$SO$_4$ and concentrated under reduced pressure. The crude product was purified by silica gel chromatography (cHex/AcOEt 95/5) to afford the title compound (0.45 g, 60%).

$C_{11}H_{16}BrNO_2$ Mass (calculated) [274]; (found) [M+H]$^+$=276.

2-(3-Bromo-pyrrol-1-yl)-pentanoic Acid (5-bromo-pyridin-2-yl)-amide

The title compound was obtained following the general procedure F1 for amide coupling and starting from 2-(3-bromo-pyrrol-1-yl)-pentanoic acid ethyl ester and 5-bromo-pyridin-2-ylamine (0.06 g, 32%).

$^1$H NMR (400 MHz, DMSO-d6) δ 11.00 (s, 1H), 8.45 (t, J=1.5 Hz, 1H), 8.04-7.98 (m, 2H), 6.97 (t, J=2.0 Hz, 1H), 6.86 (t, J=2.7 Hz, 1H), 6.08 (dd, J=2.7, 2.0 Hz, 1H), 4.91 (dd, J=8.9, 6.5 Hz, 1H), 2.06-1.85 (m, 2H), 1.22-1.08 (m, 2H), 0.87 (t, J=7.4 Hz, 3H).

$C_{14}H_{15}Br_2N_3O$, Calculated [401.10], found [M+H$^+$], 2 Br pattern, 402, RT=1.87 (method f).

Example 22: 2-(4-Bromo-3-trifluoromethyl-pyrazol-1-yl)-pentanoic Acid (5-bromo-pyrazin-2-yl)-amide

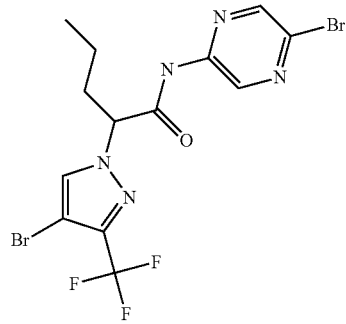 [SMILES: CCCC(C(=O)Nc1cnc(Br)cn1)n1cc(Br)c(C(F)(F)F)n1]

2-(4-Bromo-3-trifluoromethyl-pyrazol-1-yl)-pentanoic Acid ethyl ester

A suspension of 4-bromo-3-trifluoromethyl-1H-pyrazole (0.74 g, 3.44 mmol) and K$_2$CO$_3$ (0.95 g, 6.88 mmol) in acetone (16 mL) was heated at 55° C. for 10 minutes and then was allowed to cool down to room temperature. 2-Bromo-pentanoic acid ethyl ester (0.79 g, 3.78 mmol) was the added and the mixture was heated at 55° C. for 18 hours. The solvent was removed under reduced pressure and the residue was suspended in DCM and washed with H$_2$O. The organic phase was collected, dried over Na$_2$SO$_4$ and concentrated under reduced pressure to afford the title compound (1.38 g, quant.).

$C_{11}H_{14}BrF_3N_2O_2$ Mass (calculated) [343]; (found) [M+H]$^+$=345.

2-(4-Bromo-3-trifluoromethyl-pyrazol-1-yl)-pentanoic Acid (5-bromo-pyrazin-2-yl)-amide The title compound was prepared following general procedure F1 for amide coupling and starting from 2-(4-Bromo-3-trifluoromethyl-pyrazol-1-yl)-pentanoic acid ethyl ester and 5-bromo-pyrazin-2-ylamine (0.02 g, 15%).

$^1$H NMR (400 MHz, Chloroform-d3) δ 9.26 (s, 1H), 8.79 (s, 1H), 8.38 (s, 1H), 7.71 (s, 1H), 4.92 (t, J=7.7 Hz, 1H), 2.25 (q, J=7.7 Hz, 2H), 1.43-1.23 (m, 2H), 0.99 (t, J=7.5 Hz 3H). $C_{13}H_{12}Br_2F_3N_5O$, Calculated [471.07], found [M+H$^+$], 2Br pattern, 472. RT=1.81 (method f).

Example 23: 2-(4-Bromo-3-trifluoromethyl-pyrazol-1-yl)-pentanoic Acid (5-bromo-thiazol-2-yl)-amide

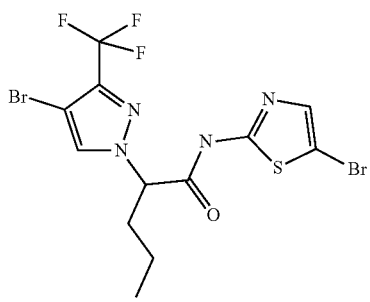 [SMILES: CCCC(C(=O)Nc1ncc(Br)s1)n1cc(Br)c(C(F)(F)F)n1]

2-(4-Bromo-3-trifluoromethyl-pyrazol-1-yl)-pentanoic Acid

The title compound was prepared following general procedure D3 for ester hydrolysis and starting form 2-[4-(4-Methoxy-phenyl)-3-trifluoromethyl-pyrazol-1-yl]-pentanoic acid ethyl ester (0.50 g, quant.).

$C_9H_{10}BrF_3N_2O_2$ Mass (calculated) [316]; (found) $[M+H]^+$=318.

2-(4-Bromo-3-trifluoromethyl-pyrazol-1-yl)-pentanoic Acid (5-bromo-thiazol-2-yl)-amide To a solution of triphenylphosphine (0.20 g, 0.76 mmol) in DCM (2 ml) cooled at 0° C., N-bromosuccinimide (0.14 g; 0.76 mmol) was added and the mixture left at 0° C. for minutes. 2-(4-Bromo-3-trifluoromethyl-pyrazol-1-yl)-pentanoic acid (0.15 g, 0.48 mmol) was added and the reaction was allowed to warm up to room temperature and lest stirring for 45 minutes. 5-Bromo-thiazol-2-ylamine (0.31 g, 1.19 mmol) was added and the mixture was left stirring for 18 hours at room temperature. The mixture was washed with 1N HCl solution and NaHCO$_3$ saturated solution. The organic phase was collected and the solvent was removed under reduced pressure. The crude product was purified by silica gel chromatography (cHex/AcOEt 3/1), to afford the title compound (0.07 g, 40%).

$^1$H NMR (400 MHz, Chloroform-d3) δ 10.41 (s, 1H), 7.72 (s, 1H), 7.49 (s, 1H), 4.98 (dd, J=8.7, 6.8 Hz, 1H), 2.32-2.14 (m, 2H), 1.46-1.20 (m, 2H), 0.98 (t, J=7.3 Hz, 3H). $C_{12}H_{11}Br_2F_3N_4OS$, Calculated [476.11], found [M+H$^+$], 2 Br pattern, 477 RT=1.90 (method f).

Example 24: 2-(4-Bromo-3-trifluoromethyl-pyrazol-1-yl)-pentanoic Acid (3-tert-butyl-isoxazol-5-yl)-amide

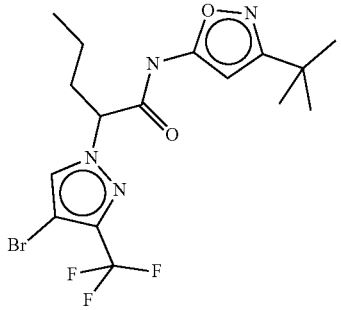

The title compound was obtained following general procedure E1 for amide coupling and starting from 2-(4-Bromo-3-trifluoromethyl-pyrazol-1-yl)-pentanoic acid and 3-tert-Butyl-isoxazol-5-ylamine (0.02 g, 15%).

$^1$H NMR (400 MHz, Chloroform-d3) δ 9.15 (s, 1H), 7.68 (s, 1H), 6.29 (s, 1H), 4.94-4.85 (m, 1H), 2.29-2.14 (m, 2H), 1.42-1.23 (m, 11H), 0.98 (t, J=7.3 Hz, 3H).

$C_{16}H_{20}N_4O_2F_3Br$, Calculated [437.25], found [M+H$^+$], Br pattern, 437-439, RT=1.90 (method f).

Example 25: 2-(3-Phenyl-[1,2,4]oxadiazol-5-yl)-pentanoic Acid (5-bromo-pyridin-2-yl)-amide

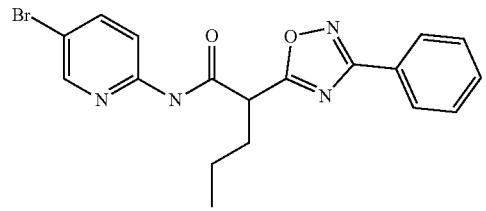 [SMILES: CCCC(C(=O)Nc1ccc(Br)cn1)c1nc(-c2ccccc2)no1]

2-(3-Phenyl-[1,2,4]oxadiazol-5-yl)-pentanoic Acid ethyl ester

Diethyl propyl malonate (1.0 g, 4.95 mmol, 1 eq) and N-hydroxy-benzamidine (0.337 g, 2.48 mmol, 0.5 eq) were mixed in a pressure tube and heated at 140° C. for 24 h. After cooling reaction, the crude residue was dissolved in AcOEt (5 mL) and purified by silica gel chromatography (cHex-50% AcOEt) to give the title compound (0.35 g, 50%). $C_{15}H_{18}N_2O_3$ Mass (calculated) [274.32]; (found) $[M+H]^+$=275.25.

2-(3-Phenyl-[1,2,4]oxadiazol-5-yl)-pentanoic Acid

The title compound was obtained following general procedure D3 for ester hydrolysis and starting from 2-(3-Phenyl-[1,2,4]oxadiazol-5-yl)-pentanoic acid ethyl ester, the crude product was purified by silica gel chromatography (cHex 20% AcOEt) to give the title compound (0.11 g, 30%).

$C_{13}H_{14}N_2O_3$ Mass (calculated) [246.27]; (found) $[M-H]^-$=245.3.

2-(3-Phenyl-[1,2,4]oxadiazol-5-yl)-pentanoic Acid (5-bromo-pyridin-2-yl)-amide 2-(3-Phenyl-[1,2,4]oxadiazol-5-yl)-pentanoic acid (0.11 g, 0.44 mmol, 1 eq) was dissolved in DCM (2 mL), CDI (0.798 g, 0.49 mmol, 1.1 eq) was added and reaction was stirred for 1 h at room temperature. 5-Bromo-2-aminopyridine (0.77 g, 0.44 mmol, 1 eq) was added and reaction was stirred for 16 h. NaOH 1N solution in $H_2O$ (2 mL) was added; organic phase was collected, dried over $Na_2SO_4$ and concentrated under vacuo. The crude product was purified by preparative HPLC to give the title compound (0.031 g, 20%).

$^1$H NMR (400 MHz, Chloroform-d3) δ 9.35 (s, 1H), 8.37 (d, J=2.4 Hz, 1H), 8.20-8.06 (m, 3H), 7.82 (dd, J=8.9, 2.4 Hz, 1H), 7.60-7.48 (m, 3H), 4.13 (t, J=7.4 Hz, 1H), 2.35-2.16 (m, 2H), 1.52-1.38 (m, 2H), 0.99 (t, J=7.3 Hz, 3H).

$C_{18}H_{17}N_4O_2Br$, Calculated [401.26], found [M+H$^+$], Br pattern 401-403, RT=1.88 (method f).

Example 26: 2-(2-Difluoromethoxy-pyridin-4-yl)-pentanoic Acid (5-bromo-pyridin-2-yl)-amide

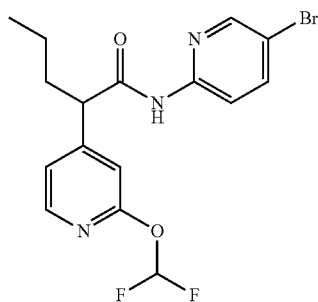 [SMILES: CCCC(C(=O)Nc1ccc(Br)cn1)c1ccnc(OC(F)F)c1]

2-(2-oxo-1,2-dihydro-pyridin-4-yl)-pentanoic Acid ethyl ester 2-(2-Methoxy-pyridin-4-yl)-pentanoic acid ethyl ester (1.0 g, 4.2 mmol, 1.0 eq.) was dissolved in acetonitrile (12 mL) at 20° C. and iodo-trimethylsilane (1.26 mL, 8.8 mmol, 2.1 eq.) was added dropwise. The mixture was heated to 80° C. for 12 h and then cooled at room temperature. The solvent was concentrated under reduced pressure and the crude product was purified by silica gel chromatography (AcOEt:cHex 1:9) to afford the title compound (0.6 g, 58%).

$C_{12}H_{17}NO_3$ mass (calculated) [222]; (found) [M+H]$^+$=223 m/z.

2-(2-difluoromethoxy-pyridin-4-yl)-pentanoic Acid ethyl ester 2-(2-oxo-1,2-dihydro-pyridin-4-yl)-pentanoic acid ethyl ester (0.50 g, 2.2 mmol, 1.0 eq) was dissolved in $CH_3CN$ (10 mL) at 20° C. and sodium chloro-difluoroacetate (0.41 g, 2.7 mmol, 1.2 eq.) was added portionwise. The reaction was heated at 100° C. for 12 h and then cooled to room temperature. The solvent was distilled under reduced pressure and the crude product was purified by silica gel chromatography (AcOEt:cHex 1:9) to give the title compound (0.26 g, 42%).

$C_{13}H_{17}F_2NO_3$ mass (calculated) [273]; (found) [M+H]$^+$=274 m/z.

2-(2-difluoromethoxy-pyridin-4-yl)-pentanoic Acid 5-(2-Br-pyridin-2-yl)-amide 2-(2-difluoromethoxy-pyridin-4-yl)-pentanoic acid ethyl ester (190 mg, 0.70 mmol, 1 eq.), 1,5,7-Triazabicyclo[4.4.0]dec-5-ene (30 mg, 0.22 mmol, 0.3 eq.) and 5-bromo-pyridin-2-yl amine (691 mg, 4 mmol, 5.7 eq.) were respectively transferred in the micro-wave tube and 2 micro-wave cycles were performed (T=130° C.; power=230 W; t=30 minutes). Then the reaction was cooled at room temperature and rinsed with dichloromethane. The organic solution was washed with sodium bicarbonate saturated solution and $H_2O$. The organic layer was concentrated under reduced pressure and the crude product was purified on silica gel chromatography (AcOEt:cHex 1:5) to give the title compound (0.036 g, 13%).

$^1$H NMR (400 MHz, Chloroform-d3) δ 8.29 (d, J=2.5 Hz, 1H), 8.18-8.11 (m, 2H), 8.04 (s, 1H), 7.81 (dd, J=8.9, 2.5 Hz, 1H), 7.46 (t, J=73.0 Hz, 1H), 7.11 (dd, J=5.3, 1.5 Hz, 1H), 6.90 (d, J=1.5 Hz, 1H), 3.48 (t, J=7.5 Hz, 1H), 2.23-2.09 (m, 1H), 1.89-1.75 (m, 1H), 1.45-1.19 (m, 2H), 0.95 (t, J=7.3 Hz, 3H).

$C_{16}H_{16}BrF_2N_3O_2$, Calculated [400.2], found [M+H$^+$], Br pattern, 400-402, RT=2.06 (method d).

Example 27: 2-(2-Difluoromethoxy-pyridin-4-yl)-pentanoic Acid (5-bromo-pyrazin-2-yl)-amide

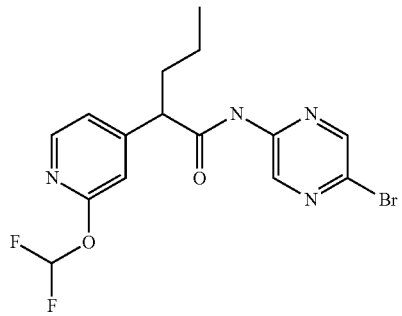 [SMILES: CCCC(C(=O)Nc1cnc(Br)cn1)c1ccnc(OC(F)F)c1]

2-(2-difluoromethoxy-pyridin-4-yl)-pentanoic acid ethyl ester (200 mg, 0.73 mmol, 1 eq.), 1,5,7-Triazabicyclo[4.4.0]dec-5-ene (30 mg, 0.22 mmol, 0.3 eq.) and 5-bromo-pyrazine-2-yl amine (690 mg, 4 mmol, 5.7 eq.) were respectively transferred in the micro-wave tube and 2 micro-wave cycles were performed (T=130° C.; power=230 W; t=30 minutes). Then the reaction was cooled at room temperature and rinsed with dichloromethane. The organic solution was washed with sodium bicarbonate saturated solution and $H_2O$. The organic layer was concentrated under reduced pressure and the crude product was purified on silica gel chromatography (AcOEt:cHex 1:5) to give the title compound (0.016 g, 7%).

$^1$H NMR (400 MHz, Chloroform-d3) δ 9.32 (d, J=1.4 Hz, 1H), 8.32 (d, J=1.6 Hz, 1H), 8.18 (d, J=5.3 Hz, 1H), 7.77 (s, 1H), 7.38 (t, J=72.8 Hz, 1H), 7.13 (dd, J=5.3, 1.6 Hz, 1H), 6.91 (d, J=1.4 Hz, 1H), 3.54 (t, J=7.5 Hz, 1H), 2.25-2.11 (m, 1H), 1.92-1.78 (m, 1H), 1.46-1.23 (m, 2H), 0.96 (t, J=7.3 Hz, 3H).

$C_{15}H_{15}N_4O_2F_2Br$, Calculated [401.21], found [M+H$^+$], Br pattern, 401-403, RT=2.17 (method e).

Example 28: 22-[6-(1-Methyl-1H-pyrazol-4-yl)-pyridin-3-yl]-pentanoic Acid (5-chloro-thiazol-2-yl)-amide

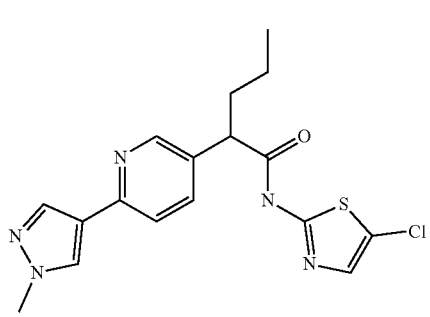 [SMILES: CCCC(C(=O)Nc1ncc(Cl)s1)c1ccc(-c2cnn(C)c2)nc1]

2-(6-Chloro-pyridin-3-yl)-pentanenitrile

The title compound was obtained starting from 2-chloro-pyridine-5-acetonitrile that was treated in the same conditions of general procedure B1 for alkylation (3.80 g, 58%).

2-[6-(1-Methyl-1H-pyrazol-3-yl)-pyridin-3-yl]-pentanenitrile

The title compound was synthesized following the general procedure O for Suzuki coupling starting from 2-(6-chloro-pyridin-3-yl)-pentanenitrile and 1-methylpyrazole-4-boronic acid pinacol ester (3.80 g, 83%).

$C_{14}H_{16}N_4$ Mass (calculated) [240]; found [M+H$^+$]=241.

2-[6-(1-Methyl-1H-pyrazol-3-yl)-pyridin-3-yl]-pentanoic Acid

The starting nitrile (3.8 g, 15.6 mmol, 1 eq) was dissolved in HCl 6N aqueous solution (40 mL), solution was heated at 100° C. for 12 h. H$_2$O was evaporated; the solid crude product was triturated with diethyl ether, filtered off and dried to give the title compound (3.7 g, 97%).

$C_{14}H_{17}N_3O_2$ Mass (calculated) [259]; found [M+H]$^+$=260.

2-[6-(1-Methyl-1H-pyrazol-4-yl)-pyridin-3-yl]-pentanoic Acid (5-bromo-thiazol-2-yl)-amide The title compound was obtained following procedure E1 for amide coupling with thionyl chloride after preparative HPLC purification (0.05 g, 37%).

$^1$H NMR (400 MHz, DMSO-d6) δ 12.65 (s, 1H), 8.44 (d, J=2.3 Hz, 1H), 8.23 (s, 1H), 7.94 (s, 1H), 7.71 (dd, J=8.3, 2.3 Hz, 1H), 7.60 (d, J=8.2 Hz, 1H), 7.50 (s, 1H), 3.90-3.81 (m, 4H), 2.11-1.97 (m, 1H), 1.80-1.66 (m, 1H), 1.28-1.13 (m, 2H), 0.87 (t, J=7.3 Hz, 3H). $C_{17}H_{18}N_5$OSCl, Calculated [375.88], found [M+H$^+$], 376, RT=1.28 (method f).

Example 29: 2-[5-Cyano-6-(1-methyl-1H-pyrazol-4-yl)-pyridin-3-yl]-pentanoic Acid (3-tert-butyl-isoxazol-5-yl)-amide

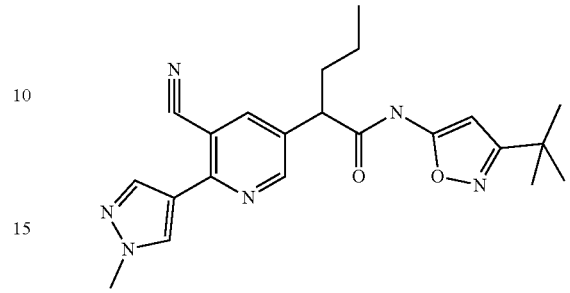

2-(6-Chloro-5-cyano-pyridin-3-yl)-pentanoic Acid tert-butyl ester

The title compound was obtained by alkylation of (6-chloro-5-cyano-pyridin-3-yl)-acetic acid tert-butyl ester was performed following the general procedure B1 (0.60 g, 60%). $C_{15}H_{19}ClN_2O_2$ Mass (calculated) [294]; (found) [M+H$^+$]=295.

2-[5-Cyano-6-(1-methyl-1H-pyrazol-4-yl)-pyridin-3-yl]-pentanoic Acid tert-butyl ester The title compound was synthesized following the general procedure O for Suzuki coupling, starting from 2-(6-chloro-5-cyano-pyridin-3-yl)-pentanoic acid tert-butyl ester and 1-methylpyrazole-4-boronic acid pinacol ester. The crude was purified by silica gel chromatography (cHex/AcOEt gradient) to give the title compound (0.25 g, 77%).

$C_{19}H_{24}N_4O_2$ Mass (calculated) [340]; (found) [M+H$^+$]=341.

2-[5-Cyano-6-(1-methyl-1H-pyrazol-4-yl)-pyridin-3-yl]-pentanoic Acid

The title compound was synthesized following the general procedure D2 starting from 2-[5-cyano-6-(1-methyl-1H-pyrazol-4-yl)-pyridin-3-yl]-pentanoic acid tert-butyl ester (0.20 g, quant.).

$C_{15}H_{16}N_4O_2$ Mass (calculated)=[284]; found [M+H$^+$]=285.

2-[5-Cyano-6-(1-methyl-1H-pyrazol-4-yl)-pyridin-3-yl]-pentanoic Acid (3-tert-butyl-isoxazol-5-yl)-amide The title compound was synthesized following the general procedure E1 starting from 2-[5-cyano-6-(1-methyl-1H-pyrazol-4-yl)-pyridin-3-yl]-pentanoic acid and 3-tert-Butyl-isoxazol-5-ylamine (0.01 g, 26%).

$^1$H NMR (400 MHz, DMSO-d6) δ 11.86 (s, 1H), 8.72 (d, J=2.4 Hz, 1H), 8.42 (s, 1H), 8.20 (d, J=2.4 Hz, 1H), 8.11 (s, 1H), 6.23 (s, 1H), 3.92 (s, 3H), 3.89-3.78 (m, 1H), 2.11 1.97 (m, 1H), 1.83-1.69 (m, 1H), 1.28-1.14 (m, 11H), 0.87 (t, J=7.3 Hz, 3H).

$C_{22}H_{26}N_6O_2$, Calculated [406.48], found [M+H$^+$], 407, RT=1.58 (method f).

Example 30: 2-[4-(4-Methoxy-phenyl)-3-trifluoromethyl-pyrazol-1-yl]-pentanoic Acid (5-bromo-pyrazin-2-yl)-amide

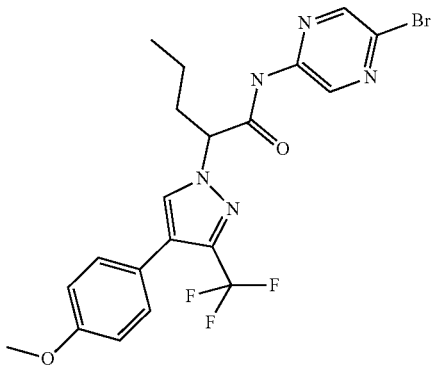 [SMILES: CCCC(C(=O)Nc1cnc(Br)cn1)n1cc(-c2ccc(OC)cc2)c(C(F)(F)F)n1]

2-[4-(4-Methoxy-phenyl)-3-trifluoromethyl-pyrazol-1-yl]-pentanoic Acid ethyl ester The title compound was prepared following general procedure O for Suzuki coupling and starting from 4-bromo-3-trifluoromethyl-1H-pyrazole and 4-methoxyphenyl boronic acid, after purification by silica gel chromatography (cHex/AcOEt 3/1) (0.09 g, 28%).

$C_{18}H_{21}F_3N_2O_3$ Mass (calculated) [370]; (found) $[M+H]^+=372$.

2-[4-(4-Methoxy-phenyl)-3-trifluoromethyl-pyrazol-1-yl]-pentanoic Acid (5-bromo-pyrazin-2-yl)-amide The title compound was prepared following general procedure F1 for amide coupling and starting from 2-[4-(4-methoxy-phenyl)-3-trifluoromethyl-pyrazol-1-yl]-pentanoic acid ethyl ester and 5-bromo-pyrazin-2-ylamine (0.01 g, 6%).

$^1$H NMR (400 MHz, Chloroform-d3) δ 9.29 (d, J=1.5 Hz, 1H), 9.21 (s, 1H), 8.38 (d, J=1.5 Hz, 1H), 7.63 (s, 1H), 7.35 (d, J=8.7 Hz, 2H), 6.95 (d, J=8.7 Hz, 2H), 4.93 (dd, J=8.6, 6.7 Hz, 1H), 3.85 (s, 3H), 2.38-2.23 (m, 2H), 1.42-1.28 (m, 2H), 1.00 (t, J=7.4 Hz, 3H). $C_{20}H_{19}BrF_3N_5O_2$, Calculated [498.30], found [M−H$^+$], Br pattern, 496-498, RT=1.87 (method f).

Example 31: 2,2-Dicyclohexyl-N-(6-methyl-pyridin-2-yl)-acetamide

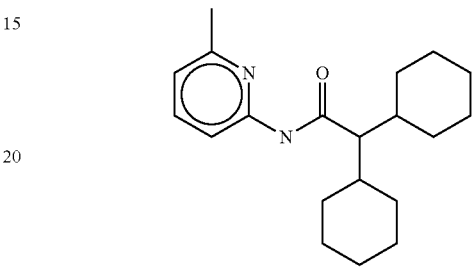

The title compound was prepared following general procedure for E1 amide coupling and starting from commercially available dicyclohexyl-acetic acid and N-(3-methyl-pyridin-2-yl)-amine (0.031 g, 8%).

1H NMR (400 MHz, cdcl3) δ 8.08 (d, J=8.3 Hz, 1H), 7.74 (s, 1H), 7.63-7.52 (m, 1H), 6.88 (d, J=7.5 Hz, 1H), 2.44 (s, 3H), 1.93-1.56 (m, 12H), 1.37-1.08 (m, 9H), 1.07-0.90 (m, 2H).

$C_{20}H_{30}N_2O$, Calculated [314,465], found [M+H$^+$] 315, RT=5.2 (method c).

Examples 32-151 listed in table 1 below were made according to the method of column 3 and characterised by NMR (data not shown), and HPLC-MS (columns 5, 6, 7 and 8)

TABLE

| | Example Name | Synthesis method | Expected MW | Retention time (min) | Found MW (M + 1) | Purity | Analytical method |
|---|---|---|---|---|---|---|---|
| 32 | 2-(5-Bromo-pyridin-3-yl)-pentanoic acid (5-chloro-pyridin-2-yl)-amide | As in Example 1 | 368.66 | 1.71 | 370 | 96 | f |
| 33 | 2-(5-Bromo-pyridin-3-yl)-pentanoic acid (5-bromo-pyrazin-2-yl)-amide | As in Example 1 | 414.10 | 1.63 | 415 | 100 | f |
| 34 | 2-(5-Bromo-pyridin-3-yl)-pentanoic acid (5-bromo-6-methyl-pyridin-2-yl)-amide | As in Example 1 | 427.13 | 1.87 | 428 | 90 | f |
| 35 | 2-(5-Bromo-pyridin-3-yl)-pentanoic acid (5-chloro-thiazol-2-yl)-amide | As in Example 1 | 374.68 | 1.73 | 376 | 97 | f |
| 36 | 2-(5-Bromo-pyridin-3-yl)-pentanoic acid (6-fluoro-pyridin-2-yl)-amide | As in Example 1 | 352.20 | 1.95 | 354 | 97 | e |
| 37 | 2-(5-Bromo-pyridin-3-yl)-pentanoic acid (6-bromo-pyridin-2-yl)-amide | As in Example 1 | 413.11 | 2.16 | 413 | 93 | e |
| 38 | 2-(5-Bromo-pyridin-3-yl)-pentanoic acid (3-tert-butyl-isoxazol-5-yl)-amide | As in Example 1 | 380.28 | 2.19 | 382 | 100 | e |
| 39 | 2-(6-Bromo-pyridin-2-yl)-pentanoic acid (5-bromo-thiazol-2-yl)-amide | As in Example 1 | 397.33 | 2.09 | 399 | 100 | e |
| 40 | 2-(5-Bromo-pyridin-3-yl)-pentanoic acid (5-fluoro-thiazol-2-yl)-amide | As in Example 1 | 358.23 | 1.58 | 359 | 98 | f |
| 41 | 2-(5-Bromo-pyridin-3-yl)-pentanoic acid (5-bromo-4-tert-butyl-thiazol-2-yl)-amide | As in Example 1 | 475.24 | 2.6 | 476 | 98 | e |
| 42 | 2-(5-Bromo-pyridin-3-yl)-pentanoic acid (5-bromo-4-methyl-thiazol-2-yl)-amide | As in Example 1 | 433.16 | 1.82 | 434 | 98 | f |
| 43 | 2-(5-Bromo-pyridin-3-yl)-pentanoic acid (5-bromo-3-methyl-pyridin-2-yl)-amide | As in Example 1 | 427.13 | 1.86 | 428 | 98 | e |

TABLE-continued

| Example | Name | Synthesis method | Expected MW | Retention time (min) | Found MW (M + 1) | Purity | Analytical method |
|---|---|---|---|---|---|---|---|
| 44 | 2-(5-Bromo-pyridin-3-yl)-pentanoic acid (5-bromo-thiazol-2-yl)-amide | As in Example 1 | 419.14 | 2.15 | 420 | 95 | e |
| 45 | 2-(5-Bromo-pyridin-3-yl)-pentanoic acid (5-bromo-6-fluoro-pyridin-2-yl)-amide | As in Example 1 | 431.10 | 1.82 | 432 | 97 | f |
| 46 | 2-(5-Bromo-pyridin-3-yl)-pentanoic acid (5-tert-butyl-isoxazol-3-yl)-amide | As in Example 1 | 380.28 | 1.8 | 382 | 100 | f |
| 47 | 2-(5-Bromo-pyridin-3-yl)-pentanoic acid (5-trifluoromethyl-pyridin-2-yl)-amide | As in Example 1 | 402.21 | 1.77 | 404 | 97 | f |
| 48 | 2-(5-Bromo-pyridin-3-yl)-pentanoic acid (5-bromo-4,6-dimethyl-pyridin-2-yl)-amide | As in Example 1 | 441.16 | 1.94 | 442 | 100 | f |
| 49 | 2-(5-Bromo-pyridin-3-yl)-pentanoic acid (5-bromo-4-methyl-pyridin-2-yl)-amide | As in Example 1 | 427.13 | 1.82 | 428 | 100 | f |
| 50 | 2-(5-Bromo-pyridin-3-yl)-pentanoic acid (5-chloro-pyrazin-2-yl)-amide | As in Example 1 | 369.64 | 1.59 | 371 | 100 | f |
| 51 | 2-(5-Bromo-pyridin-3-yl)-pentanoic acid (3-trifluoromethyl-isoxazol-5-yl)-amide | As in Example 1 | 392.17 | 1.76 | 394 | 95 | f |
| 52 | 2-(5-Bromo-pyridin-3-yl)-2-fluoro-pentanoic acid (5-chloro-pyridin-2-yl)-amide | As in Example 10 | 386.65 | 2.07 | 387 | 100 | d |
| 53 | 2-(5-Bromo-pyridin-3-yl)-2-fluoro-pentanoic acid (5-bromo-pyrazin-2-yl)-amide | As in Example 10 | 432.09 | 1.93 | 433 | 100 | d |
| 54 | 2-(5-Bromo-pyridin-3-yl)-2-fluoro-pentanoic acid (5-bromo-6-methyl-pyridin-2-yl)-amide | As in Example 10 | 445.12 | 2.51 | 446 | 95 | e |
| 55 | 2-(6-Bromo-pyridin-2-yl)-pentanoic acid (5-bromo-pyridin-2-yl)-amide | As in Example 12 | 413.11 | 1.81 | 414 | 95 | f |
| 56 | 2-(6-Bromo-pyridin-2-yl)-pentanoic acid (5-bromo-thiazol-2-yl)-amide | As in Example 12 | 419.14 | 1.76 | 420 | 95 | f |
| 57 | 2-(2-Bromo-pyridin-4-yl)-pentanoic acid (5-bromo-pyrazin-2-yl)-amide | As in Example 13 | 414.10 | 1.64 | 415 | 95 | f |
| 58 | 2-(2-Bromo-pyridin-4-yl)-pentanoic acid (5-chloro-pyridin-2-yl)-amide | As in Example 13 | 368.66 | 1.69 | 370 | 100 | f |
| 59 | 2-(5-Bromo-pyridin-3-yl)-pentanoic acid (5-fluoro-pyridin-2-yl)-amide | As in Example 13 | 352.20 | 1.55 | 354 | 100 | f |
| 60 | 2-(2-Methoxy-pyridin-4-yl)-pentanoic acid (5-bromo-thiazol-2-yl)-amide | As in Example 15 | 370.27 | 1.66 | 372 | 100 | f |
| 61 | 2-(2-Methoxy-pyridin-4-yl)-pentanoic acid (5-bromo-pyrazin-2-yl)-amide | As in Example 15 | 365.23 | 1.88 | 365 | 97 | e |
| 62 | 2-(2-Methoxy-pyridin-4-yl)-pentanoic acid (3-tert-butyl-isoxazol-5-yl)-amide | As in Example 15 | 331.41 | 2.07 | 332 | 94 | e |
| 63 | 2-(2-Methoxy-pyridin-4-yl)-pentanoic acid (5-bromo-6-methyl-pyridin-2-yl)-amide | As in Example 15 | 378.26 | 2.23 | 378 | 95 | e |
| 64 | 2-(6-Chloro-pyridin-3-yl)-pentanoic acid (5-chloro-pyridin-2-yl)-amide | As in Example 16 | 324.20 | 1.68 | 324 | 95 | f |
| 65 | 2-(6-Chloro-pyridin-3-yl)-pentanoic acid (5-chloro-pyrazin-2-yl)-amide | As in Example 16 | 325.19 | 1.85 | 325 | 95 | e |
| 66 | 2-(5-Bromo-pyridin-3-yl)-N-(5-bromo-pyrazin-2-yl)-3-(5-trifluoromethyl-furan-2-yl)-propionamide | As in Example 17 | 520.10 | 1.73 | 521 | 100 | f |
| 67 | 2-(5-Bromo-pyridin-3-yl)-N-(5-fluoro-pyridin-2-yl)-3-(5-trifluoromethyl-furan-2-yl)-propionamide | As in Example 17 | 458.20 | 1.67 | 458 | 100 | f |
| 68 | 2-(5-Bromo-pyridin-3-yl)-N-(5-chloro-pyridin-2-yl)-3-(5-trifluoromethyl-furan-2-yl)-propionamide | As in Example 17 | 474.66 | 1.78 | 474 | 100 | f |
| 69 | 2-(5-Bromo-pyridin-3-yl)-N-(5-chloro-pyrazin-2-yl)-3-(5-trifluoromethyl-furan-2-yl)-propionamide | As in Example 17 | 475.65 | 1.7 | 475 | 100 | f |
| 70 | 2-(6-Methoxy-pyridin-3-yl)-pentanoic acid (5-bromo-thiazol-2-yl)-amide | As in Example 18 | 370.27 | 1.67 | 372 | 100 | f |
| 71 | 2-(2-Methyl-pyridin-4-yl)-pentanoic acid (5-bromo-thiazol-2-yl)-amide | As in Example 18 | 354.27 | 1.07 | 356 | 95 | f |
| 72 | 2-(3-Trifluoromethyl-pyrazol-1-yl)-pentanoic acid (5-bromo-pyridin-2-yl)-amide | As in Example 19 | 391.19 | 1.77 | 393 | 100 | f |
| 73 | 2-(4-Bromo-5-methyl-3-trifluoromethyl-pyrazol-1-yl)-pentanoic acid (5-bromo-pyridin-2-yl)-amide | As in Example 19 | 484.11 | 2 | 485 | 100 | f |
| 74 | 2-(4-Bromo-3-trifluoromethyl-pyrazol-1-yl)-pentanoic acid (5-bromo-pyridin-2-yl)-amide | As in Example 19 | 470.08 | 1.91 | 471 | 95 | f |
| 75 | 2-(4-Bromo-3-cyano-pyrazol-1-yl)-pentanoic acid (5-bromo-pyridin-2-yl)-amide | As in Example 19 | 427.09 | 1.74 | 428 | 100 | f |
| 76 | 2-(5-Bromo-pyridin-3-yl)-hexanoic acid (5-bromo-pyridin-2-yl)-amide | As in Example 2 | 427.13 | 1.85 | 428 | 100 | f |
| 77 | 2-(5-Bromo-pyridin-3-yl)-hexanoic acid (5-chloro-pyridin-2-yl)-amide | As in Example 2 | 382.68 | 1.81 | 384 | 100 | f |
| 78 | 2-(5-Bromo-pyridin-3-yl)-hexanoic acid (5-bromo-pyrazin-2-yl)-amide | As in Example 2 | 428.12 | 1.2 | 429 | 100 | f |

TABLE-continued

| Example | Name | Synthesis method | Expected MW | Retention time (min) | Found MW (M + 1) | Purity | Analytical method |
|---|---|---|---|---|---|---|---|
| 79 | 2-(5-Bromo-pyridin-3-yl)-hexanoic acid (3-tert-butyl-isoxazol-5-yl)-amide | As in Example 2 | 394.31 | 1.86 | 396 | 100 | f |
| 80 | 2-(5-Bromo-pyridin-3-yl)-hexanoic acid (5-bromo-6-fluoro-pyridin-2-yl)-amide | As in Example 2 | 445.12 | 1.92 | 446 | 100 | f |
| 81 | 2-(5-Bromo-pyridin-3-yl)-5-phenyl-pentanoic acid (5-chloro-pyrazin-2-yl)-amide | As in Example 2 | 445.74 | 1.81 | 446 | 98 | f |
| 82 | 2-(5-Bromo-pyridin-3-yl)-5-phenyl-pentanoic acid (5-bromo-pyridin-2-yl)-amide | As in Example 2 | 489.20 | 1.91 | 489 | 90 | f |
| 83 | 2-(5-Bromo-3-methyl-indol-1-yl)-pentanoic acid (5-chloro-pyridin-2-yl)-amide | As in Example 20 | 420.73 | 5.28 | 421 | 95 | c |
| 84 | 2-(5-Bromo-3-methyl-indol-1-yl)-pentanoic acid (5-fluoro-pyridin-2-yl)-amide | As in Example 20 | 404.28 | 4.95 | 406 | 100 | c |
| 85 | 2-(5-Bromo-indazol-1-yl)-pentanoic acid (5-chloro-pyridin-2-yl)-amide | As in Example 20 | 407.69 | 4.73 | 409 | 95 | c |
| 86 | 2-(5-Bromo-pyrrolo[2,3-b]pyridin-1-yl)-pentanoic acid (5-chloro-pyridin-2-yl)-amide | As in Example 20 | 407.69 | 4.81 | 409 | 97 | c |
| 87 | 2-(5-Bromo-pyrrolo[2,3-b]pyridin-1-yl)-pentanoic acid (5-fluoro-pyridin-2-yl)-amide | As in Example 20 | 391.24 | 4.35 | 393 | 100 | c |
| 88 | 2-(3-Bromo-pyrrol-1-yl)-pentanoic acid (5-chloro-pyridin-2-yl)-amide | As in Example 21 | 356.65 | 1.84 | 358 | 100 | f |
| 89 | 2-(3-Bromo-pyrrol-1-yl)-pentanoic acid (5-bromo-pyrazin-2-yl)-amide | As in Example 21 | 402.08 | 1.78 | 403 | 100 | f |
| 90 | 2-(4-[4-methoxy-phenyl]-3-trifluoromethyl-pyrazol-1-yl)-pentanoic acid (5-bromo-pyrazin-2-yl)-amide | As in Example 22 | 371.66 | 1.81 | 373 | 93 | f |
| 91 | 2-(4-Bromo-3-methyl-pyrazol-1-yl)-pentanoic acid (5-bromo-pyrazin-2-yl)-amide | As in Example 22 | 417.10 | 1.74 | 418 | 100 | f |
| 92 | 2-(4-Bromo-imidazol-1-yl)-pentanoic acid (5-bromo-pyrazin-2-yl)-amide | As in Example 22 | 402.08 | 1.79 | 402 | 100 | f |
| 93 | 2-(4-Bromo-imidazol-1-yl)-pentanoic acid (5-bromo-6-methyl-pyridin-2-yl)-amide | As in Example 22 | 416.11 | 1.93 | 417 | 100 | e |
| 94 | 2-[3-(4-Methoxy-phenyl)-pyrazol-1-yl]-pentanoic acid (5-bromo-pyrazin-2-yl)-amide | As in Example 22 | 430.30 | 1.79 | 432 | 100 | f |
| 95 | 2-(4-Bromo-3-tert-butyl-pyrazol-1-yl)-pentanoic acid (5-bromo-pyrazin-2-yl)-amide | As in Example 22 | 459.18 | 2.09 | 460 | 91 | f |
| 96 | 2-(4-Bromo-3-cyano-pyrazol-1-yl)-pentanoic acid (5-bromo-pyrazin-2-yl)-amide | As in Example 22 | 428.08 | 1.67 | 427 | 100 | f |
| 97 | 2-(4-Bromo-3-propyl-pyrazol-1-yl)-pentanoic acid (5-bromo-pyrazin-2-yl)-amide | As in Example 22 | 445.15 | 1.97 | 444 | 98 | f |
| 98 | 2-(4-Bromo-3-trifluoromethyl-pyrazol-1-yl)-pentanoic acid (6-fluoro-pyridin-2-yl)-amide | As in Example 22 | 409.18 | 1.79 | 409 | 100 | f |
| 99 | 2-(4-Chloro-3-trifluoromethyl-pyrazol-1-yl)-pentanoic acid (5-bromo-pyrazin-2-yl)-amide | As in Example 22 | 426.62 | 1.8 | 428 | 92 | f |
| 100 | 2-(4-Chloro-3-trifluoromethyl-pyrazol-1-yl)-pentanoic acid (5-chloro-pyrazin-2-yl)-amide | As in Example 22 | 382.17 | 1.78 | 382 | 97 | f |
| 101 | 2-(4-Chloro-3-trifluoromethyl-pyrazol-1-yl)-pentanoic acid (5-bromo-pyridin-2-yl)-amide | As in Example 22 | 425.63 | 1.88 | 427 | 98 | f |
| 102 | 2-(4-Chloro-3-trifluoromethyl-pyrazol-1-yl)-pentanoic acid (5-chloro-pyridin-2-yl)-amide | As in Example 22 | 381.18 | 1.85 | 381 | 95 | f |
| 103 | 2-(3-Bromo-pyrrol-1-yl)-pentanoic acid (3-tert-butyl-isoxazol-5-yl)-amide | As in Example 23 | 368.27 | 1.83 | 370 | 100 | f |
| 104 | 2-(4-Bromo-3-trifluoromethyl-pyrazol-1-yl)-pentanoic acid (5-chloro-pyrazin-2-yl)-amide | As in Example 23 | 426.62 | 1.82 | 428 | 100 | f |
| 105 | 2-(4-Bromo-3-trifluoromethyl-pyrazol-1-yl)-pentanoic acid (5-fluoro-pyridin-2-yl)-amide | As in Example 23 | 409.18 | 1.76 | 411 | 100 | f |
| 106 | 1-(4-Bromo-3-trifluoromethyl-pyrazol-1-yl)-cyclobutanecarboxylic acid (5-bromo-pyridin-2-yl)-amide | As in Example 23 | 468.07 | 1.87 | 469 | 98 | f |
| 107 | 1-(4-Bromo-3-trifluoromethyl-pyrazol-1-yl)-cyclobutanecarboxylic acid (5-chloro-pyridin-2-yl)-amide | As in Example 23 | 423.62 | 1.84 | 425 | 100 | f |
| 108 | 1-(4-Bromo-3-trifluoromethyl-pyrazol-1-yl)-cyclobutanecarboxylic acid (5-chloro-pyrazin-2-yl)-amide | As in Example 23 | 424.60 | 1.75 | 426 | 100 | f |
| 109 | 1-(4-Chloro-3-trifluoromethyl-pyrazol-1-yl)-cyclobutanecarboxylic acid (5-bromo-pyrazin-2-yl)-amide | As in Example 23 | 424.60 | 1.77 | 424 | 95 | f |
| 110 | 1-(4-Chloro-3-trifluoromethyl-pyrazol-1-yl)-cyclobutanecarboxylic acid (5-bromo-pyridin-2-yl)-amide | As in Example 23 | 423.62 | 1.86 | 425 | 98 | f |
| 111 | 1-(4-Chloro-3-trifluoromethyl-pyrazol-1-yl)-cyclobutanecarboxylic acid (5-chloro-pyridin-2-yl)-amide | As in Example 23 | 379.16 | 1.83 | 379 | 98 | f |
| 112 | 1-(4-Bromo-3-cyano-pyrazol-1-yl)-cyclobutanecarboxylic acid (5-bromo-pyridin-2-yl)-amide | As in Example 23 | 425.08 | 1.69 | 424 | 95 | f |

TABLE-continued

| Example | Name | Synthesis method | Expected MW | Retention time (min) | Found MW (M + 1) | Purity | Analytical method |
|---|---|---|---|---|---|---|---|
| 113 | 2-(4-Bromo-3-trifluoromethyl-pyrazol-1-yl)-pentanoic acid (5-chloro-pyridin-2-yl)-amide | As in Example 23 | 425.63 | 1.86 | 427 | 100 | f |
| 114 | 2-(4-Bromo-3-trifluoromethyl-pyrazol-1-yl)-pentanoic acid (6-chloro-pyrimidin-4-yl)-amide | As in Example 23 | 426.62 | 1.78 | 428 | 98 | f |
| 115 | 1-(4-Bromo-3-trifluoromethyl-pyrazol-1-yl)-cyclobutanecarboxylic acid (5-bromo-pyrazin-2-yl)-amide | As in Example 23 | 469.05 | 1.78 | 468 | 95 | f |
| 116 | 1-(4-Bromo-3-trifluoromethyl-pyrazol-1-yl)-cyclobutanecarboxylic acid (5-fluoro-pyridin-2-yl)-amide | As in Example 23 | 407.16 | 1.73 | 409 | 95 | f |
| 117 | 2-[6-(1-Methyl-1H-pyrazol-4-yl)-pyridin-3-yl]-pentanoic acid (5-bromo-6-methyl-pyridin-2-yl)-amide | As in Example 28 | 428.33 | 1.4 | 430 | 99 | f |
| 118 | 2-[5-Cyano-6-(1-methyl-1H-pyrazol-4-yl)-pyridin-3-yl]-pentanoic acid (5-bromo-pyrazin-2-yl)-amide | As in Example 29 | 440.30 | 1.48 | 442 | 90 | f |
| 119 | 2-[5-Fluoro-6-(1-methyl-1H-pyrazol-4-yl)-pyridin-3-yl]-pentanoic acid (5-chloro-pyrazin-2-yl)-amide | As in Example 29 | 388.83 | 1.46 | 389 | 95 | f |
| 120 | 2-[5-Fluoro-6-(1-methyl-1H-pyrazol-4-yl)-pyridin-3-yl]-pentanoic acid (5-chloro-pyridin-2-yl)-amide | As in Example 29 | 387.84 | 1.54 | 388 | 98 | f |
| 121 | 2-[5-Cyano-6-(1-methyl-1H-pyrazol-4-yl)-pyridin-3-yl]-pentanoic acid (5-chloro-pyrazin-2-yl)-amide | As in Example 29 | 395.85 | 1.44 | 396 | 90 | f |
| 122 | 2-[5-Cyano-6-(1-methyl-1H-pyrazol-4-yl)-pyridin-3-yl]-pentanoic acid (5-fluoro-pyridin-2-yl)-amide | As in Example 29 | 378.40 | 1.4 | 379 | 95 | f |
| 123 | 2-(5-Bromo-pyridin-3-yl)-N-(5-bromo-pyridin-2-yl)-3-methyl-butyramide | As in Example 3 | 413.11 | 1.9 | 414 | 100 | d |
| 124 | 2-(5-Bromo-pyridin-3-yl)-N-(5-chloro-pyridin-2-yl)-3-methyl-butyramide | As in Example 3 | 368.66 | 1.85 | 369 | 95 | d |
| 125 | 2-(5-Bromo-pyridin-3-yl)-N-(5-bromo-pyrazin-2-yl)3-methyl-butyramide | As in Example 3 | 414.10 | 1.77 | 415 | 100 | d |
| 126 | N-(5-Bromo-3-methyl-pyridin-2-yl)-2-(5-bromo-pyridin-3-yl)-3-methyl-butyramide | As in Example 3 | 427.13 | 1.83 | 428 | 96 | e |
| 127 | 2-(5-Bromo-pyridin-3-yl)-N-(5-chloro-thiazol-2-yl)-3-methyl-butyramide | As in Example 3 | 374.68 | 1.7 | 376 | 100 | f |
| 128 | N-(5-Bromo-3-fluoro-pyridin-2-yl)-2-(5-bromo-pyridin-3-yl)-3-methyl-butyramide | As in Example 3 | 431.10 | 1.5 | 432 | 97 | f |
| 129 | 2-(5-Bromo-pyridin-3-yl)-N-(3-tert-butyl-isoxazol-5-yl)-3-methyl-butyramide | As in Example 3 | 380.28 | 1.78 | 382 | 100 | f |
| 130 | N-(5-Bromo-pyrazin-2-yl)-2,2-dicyclohexyl-acetamide | As in Example 31 | 380.32 | 2.52 | 380-382 | 97 | d |
| 131 | N-(5-Bromo-thiazol-2-yl)-2,2-dicyclohexyl-acetamide | As in Example 31 | 385.36 | 2.6 | 385-387 | 96 | d |
| 132 | 2,2-Dicyclohexyl-N-(5-fluoro-pyridin-2-yl)-acetamide | As in Example 31 | 318.43 | 2.42 | 319 | 100 | d |
| 133 | 1-(5-Bromo-pyridin-3-yl)-cyclobutanecarboxylic acid (5-bromo-pyrazin-2-yl)-amide | As in Example 4 | 412.08 | 1.5 | 413 | 93 | f |
| 134 | 1-(5-Bromo-pyridin-3-yl)-cyclobutanecarboxylic acid (5-chloro-pyridin-2-yl)-amid | As in Example 4 | 366.64 | 1.57 | 366 | 100 | f |
| 135 | 1-(5-Bromo-pyridin-3-yl)-cyclopentanecarboxylic acid (5-bromo-pyrazin-2-yl)-amide | As in Example 5 | 425.12 | 1.71 | 426 | 90 | f |
| 136 | 1-(5-Chloro-pyridin-3-yl)-cyclobutanecarboxylic acid (5-bromo-pyrazin-2-yl)-amide | As in Example 6 | 367.63 | 1.46 | 367 | 100 | f |
| 137 | 1-(5-Chloro-pyridin-3-yl)-cyclobutanecarboxylic acid (5-bromo-pyridin-2-yl)-amide | As in Example 6 | 366.64 | 1.57 | 364 | 95 | f |
| 138 | 2-(6-Chloro-5-cyano-pyridin-3-yl)-pentanoic acid (5-bromo-pyrazin-2-yl)-amide | As in Example 8 | 394.65 | 1.63 | 394 | 100 | f |
| 139 | 2-(6-Chloro-5-cyano-pyridin-3-yl)-pentanoic acid (5-bromo-pyridin-2-yl)-amide | As in Example 8 | 393.67 | 1.72 | 393 | 100 | f |
| 140 | 2-(6-Chloro-5-cyano-pyridin-3-yl)-pentanoic acid (5-chloro-pyridin-2-yl)-amide | As in Example 8 | 349.21 | 1.69 | 349 | 100 | f |
| 141 | 2-(5-Chloro-pyridin-3-yl)-pentanoic acid (5-bromo-pyrazin-2-yl)amide | As in Example 9 | 369.64 | 1.83 | 369 | 95 | f |
| 142 | 2-(5-Chloro-pyridin-3-yl)-pentanoic acid (5-chloro-pyrazin-2-yl)-amide | As in Example 9 | 325.19 | 1.58 | 323 | 95 | f |
| 143 | 2-(5-Chloro-pyridin-3-yl)-pentanoic acid (5-bromo-pyridin-2-yl)-amide | As in Example 9 | 368.66 | 1.68 | 368 | 100 | f |
| 144 | 2-(5-Chloro-pyridin-3-yl)-pentanoic acid (5-chloro-pyridin-2-yl)-amide | As in Example 9 | 324.20 | 1.65 | 324 | 100 | f |
| 145 | 2-(6-Chloro-5-methyl-pyridin-3-yl)-pentanoic acid (5-chloro-pyrazin-2-yl)-amide | As in Example 9 | 339.22 | 1.65 | 339 | 95 | f |

TABLE-continued

| | Example Name | Synthesis method | Expected MW | Retention time (min) | Found MW (M + 1) | Purity | Analytical method |
|---|---|---|---|---|---|---|---|
| 146 | 2-(6-Chloro-5-methyl-pyridin-3-yl)-pentanoic acid (5-bromo-pyrazin-2-yl)-amide | As in Example 9 | 383.67 | 1.68 | 383 | 100 | f |
| 147 | 2-(6-Chloro-5-methyl-pyridin-3-yl)-pentanoic acid (5-chloro-pyridin-2-yl)-amide | As in Example 9 | 338.23 | 1.72 | 338 | 100 | f |
| 148 | 2-(6-Chloro-5-methyl-pyridin-3-yl)-pentanoic acid (5-bromo-pyridin-2-yl)-amide | As in Example 9 | 382.68 | 1.76 | 383 | 100 | f |
| 149 | 2-(2-Chloro-pyridin-4-yl)-pentanoic acid (5-bromo-pyrazin-2-yl)-amide | As in Example 9 | 369.64 | 1.58 | 371 | 100 | f |
| 150 | 2-(2-Chloro-pyridin-4-yl)-pentanoic acid (5-chloro-pyridin-2-yl)-amide | As in Example 9 | 324.20 | 1.64 | 324 | 100 | f |
| 151 | 2-(2-Chloro-pyridin-4-yl)-pentanoic acid (5-bromo-pyridin-2-yl)-amide | As in Example 9 | 368.66 | 1.67 | 368 | 100 | f |

BIOLOGICAL ACTIVITY

Examples 1-151 were tested in the above described cellular against CHO-S1P3 R1 cells, and show IC50 values ranging from 19 nM to 590 nM.

Figure 1:
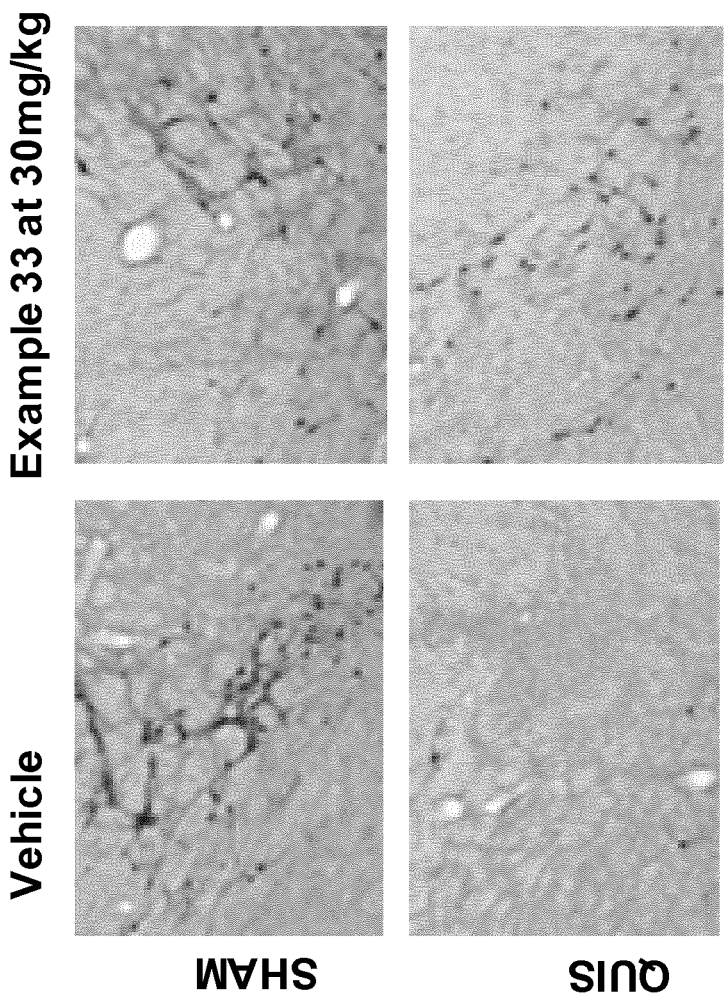
FIG. 1: Neuroprotective effect of a compound of the invention on quisqualic acid lesioned rats. Example 33 shows strong neuroprotective effects at 30 and 60 mg/Kg/day. Rat NBM ChAT-positive neuron counts using APERIO® (left), example 33 at doses of 30 and 60 mg/kg was administered once a day p.o.; the dose of 10 mg/kg was administered p.o. twice a day. In the microphotographs (right panel) a ChAT-qualitative analysis is shown in Quisqualic acid (QUIS) or Sham (SHAM)-injected rat NBM treated with vehicle or example 33 at 30 mg/kg p.o. *p<0.05 vs SHAM (Dunnet Test).
Figure 1:
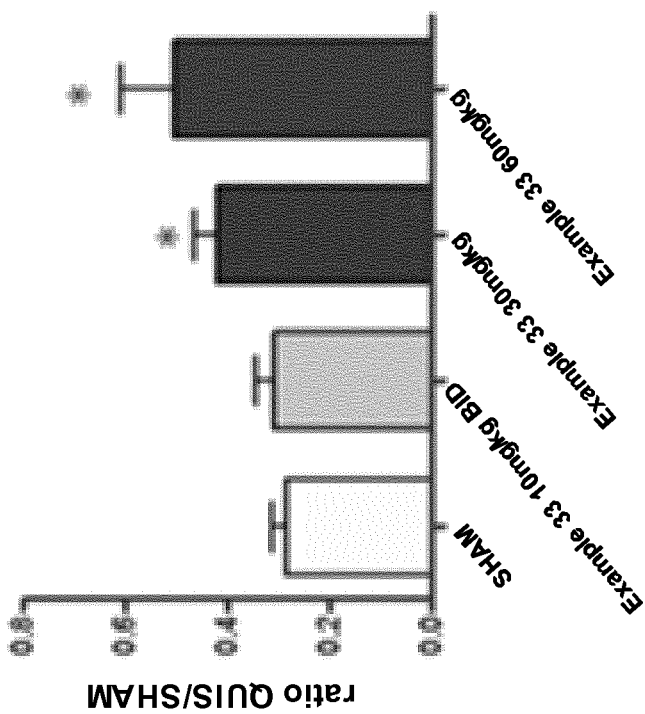

Example 33 was tested in the in vivo assays above described, at doses ranging 10 to 60 mg/kg showing anti-neuroinflammatory and neuroprotective activity (as et out in FIGS. 1-3) and improved cognitive functions (as set out in FIG. 4).

REFERENCES

Anelli, V., Bassi, R., Tettamanti, G., Viani, P. and Riboni, L. (2005) Extracellular release of newly synthesized sphingosine-1-phosphate by cerebellar granule cells and astrocytes. J. Neurochem., 92, 1204-1215.

Bajwa A, Huang L, Ye H, Dondeti K, Song S, Rosin D L, Lynch K R, Lobo P I, Li L, Okusa M D. (2012). Dendritic cell sphingosine 1-phosphate receptor-3 regulates Th1-Th2 polarity in kidney ischemia-reperfusion injury. J Immunol. 189(5):2584-96.

Balthasar S, Samulin J, Ahlgren H, Bergelin N, Lundqvist M, Toescu E C, Eggo M C, Törnquist K. (2006). Sphingosine 1-phosphate receptor expression profile and regulation of migration in human thyroid cancer cells. Biochem J. 398(3):547-56.

Brinkmann V. (2009). FTY720 (fingolimod) in Multiple Sclerosis: therapeutic effects in the immune and the central nervous system. Br J Pharmacol. 158(5):1173-82.

Brinkmann V. (2007). Sphingosine 1-phosphate receptors in health and disease: mechanistic insights from gene deletion studies and reverse pharmacology. Pharmacol Ther. 115(1):84-105.

Bradl M, Hohlfeld R. (2003). Molecular pathogenesis of neuroinflammation. J Neurol Neurosurg Psychiatry. 74(10):1364-70.

Camprubí-Robles M, Mair N, Andratsch M, Benetti C, Beroukas D, Rukwied R, Langeslag M, Proia R L, Schmelz M, Ferrer Montiel A V, Haberberger R V, Kress M. (2013). Sphingosine-1-phosphate-induced nociceptor excitation and ongoing pain behavior in mice and humans is largely mediated by S1P3 receptor. J Neurosci. 33(6):2582-92.

Casamenti F, Prosperi C, Scali C, Giovannelli L, Pepeu G. (1998). Morphological, biochemical and behavioural changes induced by neurotoxic and inflammatory insults to the nucleus basalis. Int J Dev Neurosci. 16(7-8):705-14.

Cencetti F, Bernacchioni C, Nincheri P, Donati C, Bruni P. (2010). Transforming growth factor-beta1 induces transdifferentiation of myoblasts into myofibroblasts via up-regulation of sphingosine kinase-1/S1P3 axis. Mol Biol Cell. 21(6):1111-24.

Chen L Y, Woszczek G, Nagineni S, Logun C, Shelhamer J H. (2008). Cytosolic phospholipase A2alpha activation induced by S1P is mediated by the S1P3 receptor in lung epithelial cells. Am J Physiol Lung Cell Mol Physiol. 295(2):L326-35.

Chun J, Goetzl E J, Hla T, Igarashi Y, Lynch K R, Moolenaar W. (2002). International Union of Pharmacology. XXXIV. Lysophospholipid receptor nomenclature. Pharmacol Rev 54: 265-269.

Davies L, Fassbender K, Walter S. 2013. Sphingolipids in neuroinflammation. Handb Exp Pharmacol. (216):421-30.

Ennaceur A, Delacour J. A new one-trial test for neurobiological studies of memory in rats. 1: Behavioral data. (1988). Behav Brain Res. 31(1):47-59.

Forrest M, Sun S Y, Hajdu R, Bergstrom J, Card D, Doherty G, Hale J, Keohane C, Meyers C, Milligan J, Mills S, Nomura N, Rosen H, Rosenbach M, Shei G J, Singer I I, Tian M, West S, White V, Xie J, Proia R L, Mandala S. (2004). Immune cell regulation and cardiovascular effects of sphingosine 1-phosphate receptor agonists in rodents are mediated via distinct receptor subtypes. J Pharmacol Exp Ther. 309(2):758-68.

Fischer I, Alliod C, Martinier N, Newcombe J, Brana C, Pouly S. (2011). Sphingosine kinase 1 and sphingosine 1-phosphate receptor 3 are functionally upregulated on astrocytes under pro-inflammatory conditions. PLoS One. 6(8):e23905.

Foster C A, Howard L M, Schweitzer A, Persohn E, Hiestand P C, Balatoni B, Reuschel R, Beerli C, Schwartz M, Billich A. (2007). Brain penetration of the oral immunomodulatory drug FTY720 and its phosphorylation in the central nervous system during experimental autoimmune encephalomyelitis: consequences for mode of action in multiple sclerosis. J Pharmacol Exp Ther. 323 (2):469-75.

Gude D R, Alvarez S E, Paugh S W, Mitra P, Yu J, Griffiths R, Barbour S E, Milstien S, Spiegel S. (2008). Apoptosis induces expression of sphingosine kinase 1 to release sphingosine-1-phosphate as a "come-and-get-me" signal. FASEB J. 22(8):2629-38.

Harris G L, Creason M B, Brulte G B, Herr D R. (2012). In vitro and in vivo antagonism of a G protein-coupled receptor (S1P3) with a novel blocking monoclonal antibody. PLoS One. 7(4):e35129.

Ishii I, Friedman B, Ye X, Kawamura S, McGiffert C, Contos J J, Kingsbury M A, Zhang G, Brown J H, Chun J. (2001). Selective Loss of Sphingosine 1-Phosphate Signaling with No Obvious Phenotypic Abnormality in Mice Lacking Its G Protein coupled Receptor, LPB3/EDG-3. J Biol Chem. 276(36): 33697-704.

Ishii I, Fukushima N, Ye X, Chun J. (2004). Lysophospholipid Receptors: Signaling and Biology. Annu Rev Biochem. 73:321-54.

Kanno T, Nishizaki T. (2011). Endogenous sphingosine 1-phosphate regulates spontaneous glutamate release from mossy fiber terminals via S1P(3) receptors. Life Sci. 18; 89(3-4):137-40.

Keul P, Lucke S, von Wnuck Lipinski K, Bode C, Gräler M, Heusch G, Levkau B. (2011). Sphingosine-1-phosphate receptor 3 promotes recruitment of monocyte/macrophages in inflammation and atherosclerosis. Circ Res. 108(3):314-23.

Kim E S, Kim J S, Kim S G, Hwang S, Lee C H, Moon A. (2011). Sphingosine 1-phosphate regulates matrix metalloproteinase-9 expression and breast cell invasion through S1P3-Gαq coupling. J Cell Sci. 1; 124(Pt 13):2220-30.

Kono M, Mi Y, Liu Y, Sasaki T, Allende M L, Wu Y P, Yamashita T, Proia R L. (2004). The sphingosine-1-phosphate receptors S1P1, S1P2, and S1P3 function coordinately during embryonic angiogenesis. J Biol Chem. 279(28):29367-73.

Kono Y, Nishiuma T, Nishimura Y, Kotani Y, Okada T, Nakamura S, Yokoyama M. (2007). Sphingosine kinase 1 regulates differentiation of human and mouse lung fibroblasts mediated by TGF-beta1. Am J Respir Cell Mol Biol. 37(4):395-404.

Lai W Q, Melendez A J, Leung B P. (2010). Role of sphingosine kinase and sphingosine-1-phosphate in inflammatory arthritis. World J Biol Chem. 1(11): 321-326.

Li C, Jiang X, Yang L, Liu X, Yue S, Li L. 2009. Involvement of sphingosine 1-phosphate (S1P)/S1P3 signaling in cholestasis induced liver fibrosis. Am J Pathol; 175(4): 1464-72.

Liliom K, Guan Z, Tseng J L, Desiderio D M, Tigyi G, Watsky M A. Growth factor-like phospholipids generated after corneal injury. (1998). Am J Physiol. 274:C1065-C1074.

Maceyka M, Harikumar K B, Milstien S, Spiegel S. (2012). Sphingosine-1-phosphate signaling and its role in disease. Trends Cell Biol. 22(1):50-60.

Maragakis N J, Rothstein J D. (2006). Mechanisms of Disease: astrocytes in neurodegenerative disease. Nat Clin Pract Neurol. 2(12):679-89.

Marsolais D, Rosen H. (2009). Chemical modulators of sphingosine-1-phosphate receptors as barrier-oriented therapeutic molecules. Nat Rev Drug Discov. 8(4):297-307.

Means K L, Brown J H. (2009). Cardiov Res_Sphingosine-1-phosphate receptor signalling in the heart. 82, 193-200.

Mehta D, Konstantoulaki M, Ahmmed G U, Malik A B. (2005). Sphingosine 1-phosphate-induced mobilization of intracellular Ca2+ mediates Rac activation and adherents junction assembly in endothelial cells. J Biol Chem. 280:17320-17328.

Meraz-Rios M A. Toral-Rios D, Franco-Bocanegra D, Villeda-Hernandez J, Campos-Pena V. (2013). Inflammatory process in Alzheimer's Disease. Front Integr Neurosci. 7(59): 1-15.

Mettu P, Deng P, Misra U, Gawdi G, Epstein D, Rao P. (2004). Role of lysophopholipid growth factors in the modulation of aqueous humor outflow facility. Invest. Ophthalmol. Vis. Sci. 45:2263-2271.

Murakami A, Takasugi H, Ohnuma S, Koide Y, Sakurai A, Takeda S, Hasegawa T, Sasamori J, Konno T, Hayashi K, Watanabe Y, Mori K, Sato Y, Takahashi A, Mochizuki N, Takakura N. (2010). Sphingosine 1-phosphate (S1P) regulates vascular contraction via S1P3 receptor: investigation based on a new S1P3 receptor antagonist. Mol Pharmacol. 77(4):704-13.

Niessen F, Schaffner F, Furlan-Freguia C, Pawlinski R, Bhattacharjee G, Chun J, Derian C K, Andrade-Gordon P, Rosen H, Ruf W. 2008. Dendritic cell PAR1-S1P3 signalling couples coagulation and inflammation. Nature. 452(7187):654-8.

Paxinos, G., Watson, C., Pennisi, M., Topple, A., 1985. Bregma, lambda and the interaural midpoint in stereotaxic surgery with rats of different sex, strain and weight. J. Neurosci. Methods 13, 139-143.

Pyne S and Pyne J N. (2000). Sphingosine 1-phosphate signalling in mammalian cells. Biochem J. 349, 385-402.

Rosen H, Gonzalez-Cabrera P J, Sanna M G, Brown S. (2009). Sphingosine 1-phosphate receptor signaling. Annu Rev Biochem. 78:743-68.

Rouach N, Pébay A, Même W, Cordier J, Ezan P, Etienne E, Giaume C, Tencé M. (2006). S1P inhibits gap junctions in astrocytes: involvement of G and Rho GTPase/ROCK. Eur J Neurosci. 23(6):1453-1464.

Scali C, Giovannini M G, Prosperi C, Bartolini L, and Pepeu G (1997). Tacrine administration enhances extracellular acetylcholine in vivo and restores the cognitive impairment in aged rats. Pharmacol Res 36:463-469.

Sarnia M G, Liao J, Jo E, Alfonso C, Ahn M Y, Peterson M S, Webb B, Lefebvre S, Chun J, Gray N, Rosen H. (2004). Sphingosine 1-Phosphate (S1P) Receptor Subtypes S1P1 and S1P3, Respectively, Regulate Lymphocyte Recirculation and Heart Rate. J Biol Chem. 279(14):13839-48.

Shea B S, Tager A M. (2012). Open Rheumat J. 6(Suppl 1: M8) 123-129.

Singleton P A, Dudek S M, Ma S F, Garcia J G. (2006). Transactivation of sphingosine 1-phosphate receptors is essential for vascular barrier regulation. Novel role for hyaluronan and CD44 receptor family. J Biol Chem. 281(45):34381-93.

Spiegel S, Milstien S. (2003). Exogenous and intracellularly generated sphingosine 1-phosphate can regulate cellular processes by divergent pathways. Biochem Soc Trans. 31(Pt 6):1216-9.

Stamer W D, Read A T, Sumida G M, Ethier C R. (2009). Sphingosine-1-phosphate effects on the inner wall of Schlemm's canal and outflow facility in perfused human eyes. Exp Eye Res. 89(6):980-8.

Sun X, Shikata Y, Wang L, Ohmori K, Watanabe N, Wada J, Shikata K, Birukov K G, Makino H, Jacobson J R, Dudek S M, Garcia J G. (2009). Enhanced interaction between focal adhesion and adherens junction proteins: involvement in sphingosine 1-phosphate-induced endothelial barrier enhancement. Microvasc Res. 77:304-313.

Takasugi N, Sasaki T, Suzuki K, Osawa S, Isshiki H, Hori Y, Shimada N, Higo T, Yokoshima S, Fukuyama T, Lee V M, Trojanowski J Q, Tomita T, Iwatsubo T. (2011). BACE1 activity is modulated by cell-associated sphingosine-1-phosphate. J Neurosci. 31(18):6850-7.

Takasugi N, Sasaki T, Ebinuma I, Osawa S, Isshiki H, Takeo K, Tomita T, Iwatsubo T. (2013). FTY720/fingolimod, a sphingosine analogue, reduces amyloid-β production in neurons. PLoS One. 8(5):e64050.

Takuwa N, Ohkura S, Takashima S, Ohtani K, Okamoto Y, Tanaka T, Hirano K, Usui S, Wang F, Du W, Yoshioka K, Banno Y, Sasaki M, Ichi I, Okamura M, Sugimoto N, Mizugishi K, Nakanuma Y, Ishii I, Takamura M, Kaneko S, Kojo S, Satouchi K, Mitumori K, Chun J, Takuwa Y. (2010). S1P3-mediated cardiac fibrosis in sphingosine kinase 1 transgenic mice involves reactive oxygen species. Cardiovasc Res. 85(3):484-93.

Taniguchi M, Kitatani K, Kondo T, Hashimoto-Nishimura M, Asano S, Hayashi A, Mitsutake S, Igarashi Y, Umehara H, Takeya H, Kigawa J, Okazaki T (2012). Regulation of autophagy and its associated cell death by "sphingolipid rheostat": reciprocal role of ceramide and sphingosine 1-phosphate in the mammalian target of rapamycin pathway. J Biol Chem. 287(47):39898-910.

Trifilieff A, Fozard J R. (2012). Sphingosine-1-phosphate-induced airway hyper-reactivity in rodents is mediated by the sphingosine-1-phosphate type 3 receptor. J Pharmacol Exp Ther. 342(2):399-406.

Uhlig S, Yang Y. (2013). Sphingolipids in Disease. Handbook of Experimental Pharmacology, Sphingolipids in Acute Lung Injury. Vol. 216, pp 227-246.

Welch S P, Sim-Selley L J, Selley D E. (2012). Sphingosine-1-phosphate receptors as emerging targets for treatment of pain. Biochem Pharmacol. 84(12):1551-62.

Wu Y P, Mizugishi K, Bektas M, Sandhoff R, Proia R L. (2008). Sphingosine kinase 1/S1P receptor signaling axis controls glial proliferation in mice with Sandhoff disease. Hum Mol Genet. 17(15):2257-64.

Yamashita H, Kitayama J, Shida D, Yamaguchi H, Mori K, Osada M, Aoki S, Yatomi Y, Takuwa Y, Nagawa H. (2006). Sphingosine 1-phosphate receptor expression profile in human gastric cancer cells: differential regulation on the migration and proliferation. J Surg Res. 130(1):80-7.

Yin Z, Fan L, Wei L, Gao H, Zhang R, Tao L, Cao F, Wang H. (2012). FTY720 protects cardiac microvessels of diabetes: a critical role of S1P1/3 in diabetic heart disease. PLoS One. 7(8):e42900.

Young N and Van Brocklyn J R. (2007). Roles of Sphingosine-1-Phosphate (S1P) Receptors in Malignant behavior of Glioma Cells. Differential Effects of S1P2 on Cell Migration and Invasiveness. Exp Cell Res. 1; 313(8):1615-1627.

Zhang Y H, Fehrenbacher J C, Vasko M R, Nicoll G D. (2006). Sphingosine-1-Phosphate Via Activation of a G-Protein-Coupled Receptor(s) Enhances the Excitability of Rat Sensory Neurons. J Neurophysiol. 96: 1042-1052.

Brinkmann V. (2007). Sphingosine 1-phosphate receptors in health and disease: mechanistic insights from gene deletion studies and reverse pharmacology. Pharmacol Ther. 115(1):84-105.

Spiegel S, Milstien S. (2003). Exogenous and intracellularly generated sphingosine 1-phosphate can regulate cellular processes by divergent pathways. Biochem Soc Trans. 31(Pt 6):1216-9.

Forrest M, Sun S Y, Hajdu R, Bergstrom J, Card D, Doherty G, Hale J, Keohane C, Meyers C, Milligan J, Mills S, Nomura N, Rosen H, Rosenbach M, Shei G J, Singer I I, Tian M, West S, White V, Xie J, Proia R L, Mandala S. (2004). Immune cell regulation and cardiovascular effects of sphingosine 1-phosphate receptor agonists in rodents are mediated via distinct receptor subtypes. J Pharmacol Exp Ther. 309(2):758-68.

Liliom K, Guan Z, Tseng J L, Desiderio D M, Tigyi G, Watsky M A. Growth factor-like phospholipids generated after corneal injury. (1998). Am J Physiol. 274:C1065-C1074.

Mettu P, Deng P, Misra U, Gawdi G, Epstein D, Rao P. (2004). Role of lysophopholipid growth factors in the modulation of aqueous humor outflow facility. Invest. Ophthalmol. Vis. Sci. 45:2263-2271.

Rouach N, Pébay A, Même W, Cordier J, Ezan P, Etienne E, Giaume C, Tencé M. (2006). S1P inhibits gap junctions in astrocytes: involvement of G and Rho GTPase/ROCK. Eur J Neurosci. 23(6):1453-1464.

Casamenti F, Prosperi C, Scali C, Giovannelli L, Pepeu G. (1998). Morphological, biochemical and behavioural changes induced by neurotoxic and inflammatory insults to the nucleus basalis.
Int J Dev Neurosci. 16(7-8):705-14.

The invention claimed is:

1. A compound of formula (A),

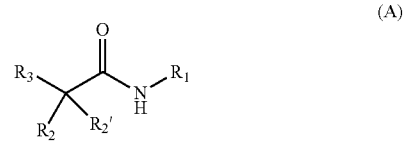

wherein

•-$R_1$ is

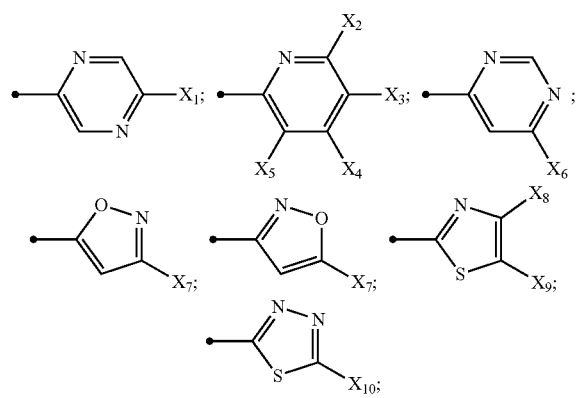

$X_1$, $X_6$, $X_7$, and $X_{10}$ are halogen, $C_1$-$C_4$ linear branched or cyclic alkyl optionally substituted with one or more fluorine atoms;

$X_9$ is chlorine, bromine, $C_1$-$C_4$ linear branched or cyclic alkyl optionally substituted with one or more fluorine atoms;

X₂, X₃, X₄, X₅ and X₈, are hydrogen, halogen, C₁-C₄ linear branched or cyclic alkyl optionally substituted with one or more fluorine atoms;

with the proviso that at least one of X₂, X₃, X₄, and X₅ is not hydrogen

R₂ is a C₃-C₆ linear branched or cyclic alkyl optionally substituted with phenyl, with one or more fluorine atoms or with trifluoromethyl-furanyl;

R₂' is hydrogen, F, C₁-C₃ linear or branched alkyl optionally substituted with one or more fluorine atoms;

or R₂ and R₂' together with the carbon atom they are attached to form a C₃-C₆ cycloalkyl ring;

•-R₃ is

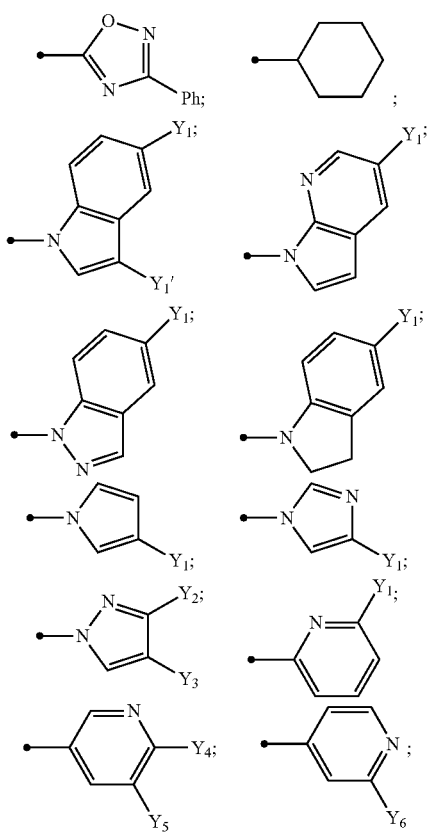

Y₁ is halogen;
Y₁' is C₁-C₃ linear branched or cyclic alkyl optionally substituted with one or more fluorine atoms;
Y₂ is cyano or methoxyphenyl, C₁-C₃ linear branched or cyclic alkyl optionally substituted with one or more fluorine atoms;
Y₃ is hydrogen, halogen or methoxyphenyl;
Y₄ is hydrogen, halogen, N-methylpyrazolyl or a C₁-C₃ linear branched or cyclic alkoxy optionally substituted with one or more fluorine atoms,
Y₅ is hydrogen halogen, cyano, or a C₁-C₃ linear branched or cyclic alkyl optionally substituted with one or more fluorine atoms;
with the proviso that at least one of Y₄ and Y₅ is not hydrogen;
Y₆ is halogen, C₁-C₃ linear branched or cyclic alkyl optionally substituted with one or more fluorine atoms, or a C₁-C₃ linear or cyclic alkoxy optionally substituted with one or more fluorine atoms;

enantiomers, enantiomerically enriched mixtures, and pharmaceutically acceptable salts thereof.

2. The compound of claim 1 wherein
X₁ is halogen;
X₂ is hydrogen, halogen or methyl;
X₃ is hydrogen, halogen or trifluoromethyl;
X₄ is hydrogen or methyl;
X₅ is hydrogen or halogen;
X₆ is halogen;
with the proviso that at least one of X₂, X₃, X₄, and X₅ is not hydrogen;
X₇ is t-butyl or trifluoromethyl;
X₈ is hydrogen, methyl or t-butyl;
X₉ is chlorine or bromine;
X₁₀ is t-butyl;
R₂ is n-propyl, 3-phenyl-n-propyl, i-propyl, n-butyl, cyclohexyl, (5-trifluoromethyl-furan-2yl)-methyl;
R₂' is hydrogen, F, methyl;
or R₂ and R₂' together with the carbon atom they are attached to form a cyclobutyl or cyclopentyl group;
Y₁ is halogen;
Y₁' is methyl;
Y₂ is methyl, n-propyl, cyano, trifluoromethyl or 4-methoxyphenyl;
Y₃ is hydrogen, halogen, or 4-methoxyphenyl;
Y₄ is hydrogen, halogen, methoxy or 1-methyl-pyrazol-4-yl;
Y₅ is hydrogen, halogen, cyano or methyl;
with the proviso that at least one of Y₄ and Y₅ is not hydrogen; and
Y₆ is halogen, methoxy or difluoromethoxy.

3. The compound of claim 1, wherein •-R₁ is selected from the group consisting of

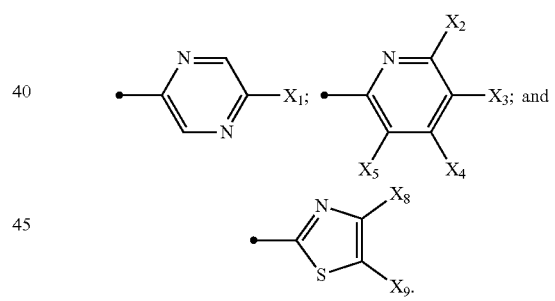

4. The compound of claim 3, which is selected from the group consisting of
1-(5-Chloro-pyridin-3-yl)-cyclobutanecarboxylic acid (5-chloro-pyridin-2-yl)-amide;
2-(6-Chloro-5-cyano-pyridin-3-yl)-pentanoic acid (5-chloro-pyrazin-2-yl)-amide;
2-(6-Chloro-5-fluoro-pyridin-3-yl)-pentanoic acid (5-bromo-pyrazin-2-yl)-amide;
2-(6-Bromo-pyridin-2-yl)-pentanoic acid (5-bromo-pyrazin-2-yl)-amide;
2-(2-Bromo-pyridin-4-yl)-pentanoic acid (5-bromo-pyridin-2-yl)-amide;
2-(2-Methoxy-pyridin-4-yl)-pentanoic acid (5-bromo-pyridin-2-yl)-amide;
2-(6-Methoxy-pyridin-3-yl)-pentanoic acid (5-bromo-pyridin-2-yl)-amide;
2-(4-Bromo-3-trifluoromethyl-pyrazol-1-yl)-pentanoic acid (5-bromo-pyrazin-2-yl)-amide;

2-(2-Difluoromethoxy-pyridin-4-yl)-pentanoic acid (5-bromo-pyridin-2-yl)-amide;
2-[6-(1-Methyl-1H-pyrazol-4-yl)-pyridin-3-yl]-pentanoic acid (5-chloro-thiazol-2-yl)-amide;
2-(5-Bromo-pyridin-3-yl)-pentanoic acid (5-bromo-pyrazin-2-yl)-amide;
2-(5-Bromo-pyridin-3-yl)-pentanoic acid (5-bromo-3-methyl-pyridin-2-yl)-amide;
2-(5-Bromo-pyridin-3-yl)-pentanoic acid (5-bromo-6-fluoro-pyridin-2-yl)-amide;
2-(5-Bromo-pyridin-3-yl)-pentanoic acid (5-chloro-pyrazin-2-yl)-amide;
2-(5-Bromo-pyridin-3-yl)-2-fluoro-pentanoic acid (5-chloro-pyridin-2-yl)-amide;
2-(2-Bromo-pyridin-4-yl)-pentanoic acid (5-bromo-pyrazin-2-yl)-amide;
2-(2-Bromo-pyridin-4-yl)-pentanoic acid (5-chloro-pyridin-2-yl)-amide;
2-(5-Bromo-pyridin-3-yl)-pentanoic acid (5-fluoro-pyridin-2-yl)-amide;
2-(2-Methoxy-pyridin-4-yl)-pentanoic acid (5-bromo-thiazol-2-yl)-amide;
2-(2-Methoxy-pyridin-4-yl)-pentanoic acid (5-bromo-pyrazin-2-yl)-amide;
2-(4-Bromo-3-trifluoromethyl-pyrazol-1-yl)-pentanoic acid (5-bromo-pyridin-2-yl)-amide;
2-(4-Bromo-3-cyano-pyrazol-1-yl)-pentanoic acid (5-bromo-pyridin-2-yl)-amide;
2-(5-Bromo-pyridin-3-yl)-hexanoic acid (5-bromo-pyrazin-2-yl)-amide;
2-(4-[4-methoxy-phenyl]-3-trifluoromethyl-pyrazol-1-yl)-pentanoic acid (5-bromo-pyrazin-2-yl)-amide;
2-(4-Bromo-3-methyl-pyrazol-1-yl)-pentanoic acid (5-bromo-pyrazin-2-yl)-amide;
2-(4-Bromo-imidazol-1-yl)-pentanoic acid (5-bromo-pyridin-2-yl)-amide;
2-[3-(4-Methoxy-phenyl)-pyrazol-1-yl]-pentanoic acid (5-bromo-pyrazin-2-yl)-amide;
2-(4-Bromo-3-cyano-pyrazol-1-yl)-pentanoic acid (5-bromo-pyrazin-2-yl)-amide;
2-[5-Fluoro-6-(1-methyl-1H-pyrazol-4-yl)-pyridin-3-yl]-pentanoic acid (5-chloro-pyrazin-2-yl)-amide;
2-[5-Cyano-6-(1-methyl-1H-pyrazol-4-yl)-pyridin-3-yl]-pentanoic acid (5-chloro-pyrazin-2-yl)-amide;
2-(5-Bromo-pyridin-3-yl)-N-(5-bromo-pyrazin-2-yl)3-methyl-butyramide;
N-(5-Bromo-3-fluoro-pyridin-2-yl)-2-(5-bromo-pyridin-3-yl)-3-methyl-butyramide;
N-(5-Bromo-pyrazin-2-yl)-2,2-dicyclohexyl-acetamide;
1-(5-Bromo-pyridin-3-yl)-cyclobutanecarboxylic acid (5-bromo-pyrazin-2-yl)-amide;
1-(5-Chloro-pyridin-3-yl)-cyclobutanecarboxylic acid (5-bromo-pyrazin-2-yl)-amide;
2-(6-Chloro-5-cyano-pyridin-3-yl)-pentanoic acid (5-bromo-pyrazin-2-yl)-amide;
2-(5-Chloro-pyridin-3-yl)-pentanoic acid (5-bromo-pyrazin-2-yl)amide;
2-(5-Chloro-pyridin-3-yl)-pentanoic acid (5-chloro-pyrazin-2-yl)-amide;
2-(6-Chloro-5-methyl-pyridin-3-yl)-pentanoic acid (5-chloro-pyrazin-2-yl)-amide;
and 2-(2-Chloro-pyridin-4-yl)-pentanoic acid (5-bromo-pyrazin-2-yl)-amide.

5. The compound of claim 1 wherein •-R$_1$ is

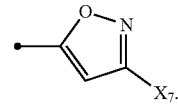

6. The compound of claim 5, which is selected from the group consisting of 2-(5-Bromo-pyridin-3-yl)-pentanoic acid (3-tert-butyl-isoxazol-5-yl)-amide and 2-(5-Bromo-pyridin-3-yl)-hexanoic acid (3-tert-butyl-isoxazol-5-yl)-amide.

7. The compound of claim 3, wherein •-R$_3$ is selected from the group consisting of

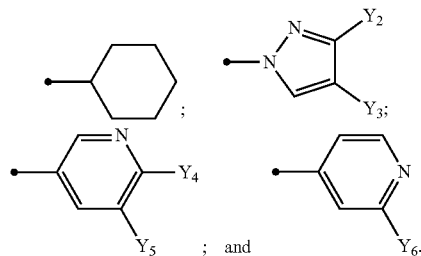

8. A pharmaceutical composition containing a compound according to claim 1.

9. A method of treating a disease selected from the group consisting of arthritis, fibrosis, inflammatory syndromes, atherosclerosis, vascular diseases, asthma, bradycardia, acute lung injury, lung inflammation, cancer, ocular hypertension, glaucoma, a neuroinflammatory disease, a neurodegenerative disease, Sandhoff's disease, kidney ischemia-reperfusion injury, pain, and diabetic heart disease in a subject in need thereof, said method comprising:
administering to said subject an effective amount of the pharmaceutical composition according to claim 8.

10. A process of synthesizing the compounds of claim 1 comprising the coupling of a compound of structure II

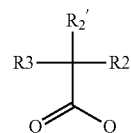

with a compound of structure III

R$_1$—N

under suitable conditions.

11. The method of claim 10, wherein the compound of structure II is synthesized by alkylation of a compound of general structure V wherein R2 and R2' are H

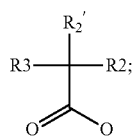

or alkylation of a compound of general structure VI wherein R2 is an alkyl and R2' is H

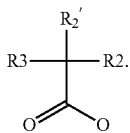

12. A compound of formula (A),

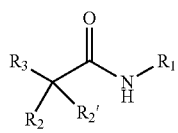

wherein
• -$R_1$ is

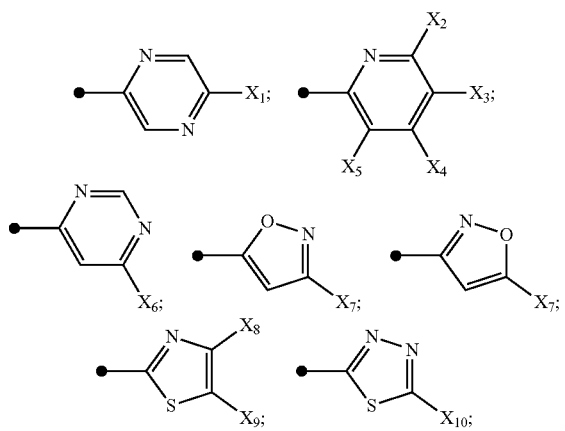

$X_4$, $X_6$, $X_7$, $X_9$ and $X_{10}$ are halogen, $C_1$-$C_4$ linear branched or cyclic alkyl optionally substituted with one or more fluorine atoms;
$X_2$, $X_3$, $X_4$, $X_5$ and $X_8$, are hydrogen, halogen, $C_1$-$C_4$ linear branched or cyclic alkyl optionally substituted with one or more fluorine atoms;
with the proviso that at least one of $X_2$, $X_3$, $X_4$, and $X_5$ is not hydrogen
$R_2$ is a $C_3$-$C_6$ linear branched or cyclic alkyl optionally substituted with phenyl, with one or more fluorine atoms or with trifluoromethyl-furanyl;
$R_2'$ is hydrogen, F, $C_1$-$C_3$ linear or branched alkyl optionally substituted with one or more fluorine atoms;
or $R_2$ and $R_2'$ together with the carbon atom they are attached to form a $C_3$-$C_6$ cycloalkyl ring;
• -$R_3$ is

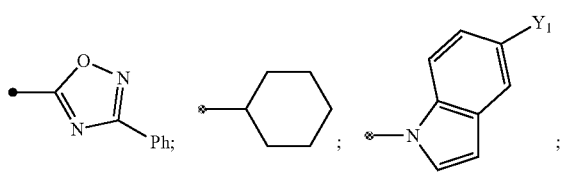

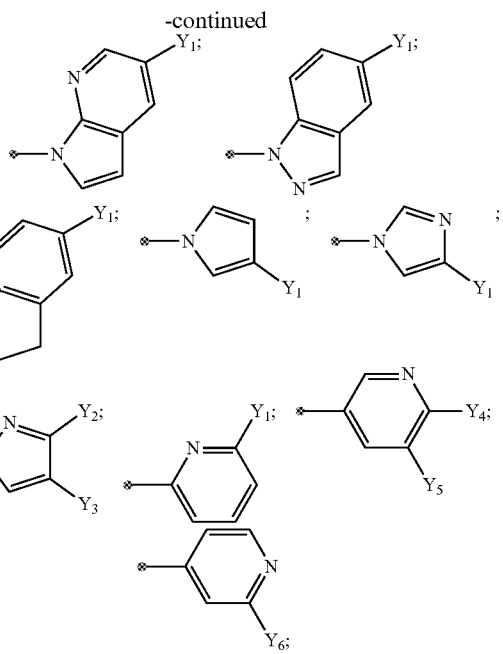

$Y_1$ is halogen;
$Y_1'$ is $C_1$-$C_3$ linear branched or cyclic alkyl optionally substituted with one or more fluorine atoms;
$Y_2$ is cyano or methoxyphenyl, $C_1$-$C_3$ linear branched or cyclic alkyl optionally substituted with one or more fluorine atoms;
$Y_3$ is hydrogen, halogen or methoxyphenyl;
$Y_4$ is hydrogen, halogen, N-methylpyrazolyl or a $C_1$-$C_3$ linear branched or cyclic alkoxy optionally substituted with one or more fluorine atoms,
$Y_5$ is hydrogen halogen, cyano, or a $C_1$-$C_3$ linear branched or cyclic alkyl optionally substituted with one or more fluorine atoms;
with the proviso that at least one of $Y_4$ and $Y_5$ is not hydrogen;
$Y_6$ is fluorine, bromine, $C_1$-$C_3$ linear branched or cyclic alkyl optionally substituted with one or more fluorine atoms, or a $C_1$-$C_3$ linear branched or cyclic alkoxy optionally substituted with one or more fluorine atoms;
enantiomers, enantiomerically enriched mixtures, and pharmaceutically acceptable salts thereof.

13. The compound of claim 12 wherein
$X_1$ is halogen;
$X_2$ is hydrogen, halogen or methyl;
$X_3$ is hydrogen, halogen or trifluoromethyl;
$X_4$ is hydrogen or methyl;
$X_5$ is hydrogen or halogen;
$X_6$ is halogen;
with the proviso that at least one of $X_2$, $X_3$, $X_4$, and $X_5$ is not hydrogen;
$X_7$ is t-butyl or trifluoromethyl;
$X_8$ is hydrogen, methyl or t-butyl;
$X_9$ is halogen;
$X_{10}$ is t-butyl;
$R_2$ is n-propyl, 3-phenyl-n-propyl, i-propyl, n-butyl, cyclohexyl, (5-trifluoromethyl-furan-2yl)-methyl;
$R_2'$ is hydrogen, F, methyl;
or $R_2$ and $R_2'$ together with the carbon atom they are attached to form a cyclobutyl or cyclopentyl group;
$Y_1$ is halogen;
$Y_1'$ is methyl;

Y$_2$ is methyl, n-propyl, cyano, trifluoromethyl or 4-methoxyphenyl;
Y$_3$ is hydrogen, halogen, or 4-methoxyphenyl;
Y$_4$ is hydrogen, halogen, methoxy or 1-methyl-pyrazol-4-yl;
Y$_5$ is hydrogen, halogen, cyano or methyl;
with the proviso that at least one of Y$_4$ and Y$_5$ is not hydrogen;
Y$_6$ is fluorine, bromine or difluoromethoxy.

14. The compound of claim 12, wherein •-R$_1$ is selected from the group consisting of

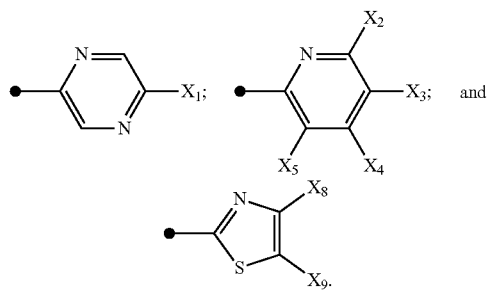

15. The compound of claim 12 wherein •-R$_1$ is

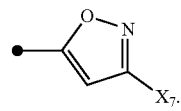

16. The compound of claim 14, wherein •-R$_3$ is selected from the group consisting of

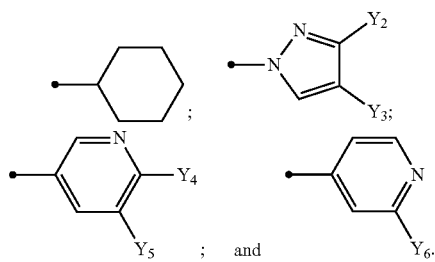

17. A pharmaceutical composition containing a compound according to claim 12.

18. A method of treating a disease selected from the group consisting of arthritis, fibrosis, inflammatory syndromes, atherosclerosis, vascular diseases, asthma, bradycardia, acute lung injury, lung inflammation, cancer, ocular hypertension, glaucoma, a neuroinflammatory disease, a neurodegenerative disease, Sandhoff's disease, kidney ischemia-reperfusion injury, pain, and diabetic heart disease in a subject in need thereof, said method comprising:
administering to said subject an effective amount of the pharmaceutical composition according to claim 17.

19. A process of synthesizing the compounds of claim 12 comprising the coupling of a compound of structure II

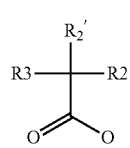

II with a compound of structure III

under suitable conditions.

20. The method of claim 19, wherein the compound of structure II is synthesized by alkylation of a compound of general structure V wherein R2 and R2' are H

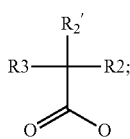

V or alkylation of a compound of general structure VI wherein R2 is an alkyl and R2' is H

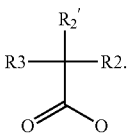

VI

* * * * *